(12) United States Patent
Davis et al.

(10) Patent No.: US 6,599,908 B1
(45) Date of Patent: Jul. 29, 2003

(54) FUSED POLYCYCLIC 2-AMINOPYRIMIDINE DERIVATIVES

(75) Inventors: Jeremy Martin Davis, Wokingham (GB); Peter David Davis, Aston Rowant (GB); David Festus Charles Moffat, Maidenhead (GB); Mark James Batchelor, Cumnor Hill (GB)

(73) Assignee: Celltech R & D Limited (GB)

(*) Notice: Subject to any disclaimer, the term of this patent is extended or adjusted under 35 U.S.C. 154(b) by 0 days.

(21) Appl. No.: 09/517,601

(22) Filed: Mar. 2, 2000

Related U.S. Application Data

(62) Division of application No. 08/997,174, filed on Dec. 22, 1997, now Pat. No. 6,057,329.

(30) Foreign Application Priority Data

Dec. 23, 1996 (GB) .............................. 9626742
Apr. 22, 1997 (GB) .............................. 9708115

(51) Int. Cl.⁷ .................... A61K 31/519; C07D 487/04; C07D 495/04
(52) U.S. Cl. ................. 514/267; 544/250; 544/246
(58) Field of Search .................. 544/250; 514/267

(56) References Cited

U.S. PATENT DOCUMENTS

| | | | |
|---|---|---|---|
| 3,947,467 A | 3/1976 | Verge et al. ............. 260/310 R |
| 4,012,495 A | 3/1977 | Schmiechen et al. ....... 514/424 |
| 4,015,017 A | 3/1977 | Gazave et al. ............. 514/687 |
| 4,153,713 A | 5/1979 | Huth et al. ................. 514/423 |
| 4,193,926 A | 3/1980 | Schmiechen et al. ....... 548/517 |
| 4,303,649 A | 12/1981 | Jones ............................ 514/8 |
| 4,659,363 A | 4/1987 | Hubele et al. ................. 71/92 |
| 4,694,009 A | 9/1987 | Hubele et al. ............. 514/269 |
| 4,788,195 A | 11/1988 | Torley et al. ............. 514/252 |
| 4,792,561 A | 12/1988 | Walker et al. ............. 514/312 |
| 4,876,252 A | 10/1989 | Torley et al. ............ 514/224.8 |
| 4,897,396 A | 1/1990 | Hubele ..................... 514/275 |
| 4,921,862 A | 5/1990 | Walker et al. ............. 514/312 |
| 4,966,622 A | 10/1990 | Rempfler et al. .............. 71/92 |
| 4,971,959 A | 11/1990 | Hawkins ..................... 514/150 |
| 4,987,132 A | 1/1991 | Mase et al. ................ 514/252 |
| 5,124,455 A | 6/1992 | Lombardo .................. 546/181 |
| 5,128,358 A | 7/1992 | Saccomano et al. ........ 514/392 |
| 5,159,078 A | 10/1992 | Rempfler et al. ........... 544/330 |
| 5,164,372 A | 11/1992 | Matsuo et al. ................ 514/19 |
| 5,175,167 A | 12/1992 | Zipperer et al. ............. 514/277 |
| 5,177,085 A | 1/1993 | Naef ............................ 514/307 |
| 5,236,918 A | 8/1993 | Amschler et al. ........... 514/247 |
| 5,274,002 A | 12/1993 | Hawkins ..................... 514/530 |
| 5,298,511 A | 3/1994 | Waterson .................... 514/311 |
| 5,326,898 A | 7/1994 | Chandraratna ................ 560/17 |
| 5,340,827 A | 8/1994 | Beeley et al. ............... 514/352 |
| 5,491,147 A | 2/1996 | Boyd et al. ................. 514/247 |
| 5,521,184 A | 5/1996 | Zimmermann ............. 514/252 |
| 5,550,137 A | 8/1996 | Beeley et al. ............... 514/354 |
| 5,580,888 A | 12/1996 | Warrellow et al. .......... 514/332 |

(List continued on next page.)

FOREIGN PATENT DOCUMENTS

| | | |
|---|---|---|
| DE | 250 1443 | 7/1975 |
| EP | 0 537 742 A2 | 4/1983 |
| EP | 0 233 461 A2 | 8/1987 |
| EP | 0 295 210 A1 | 12/1988 |
| EP | 0 337 943 A2 | 10/1989 |
| EP | 0 393 500 A1 | 10/1990 |
| EP | 0 490 823 A1 | 6/1991 |
| EP | 0 470 805 A1 | 2/1992 |
| EP | 0 497 564 A1 | 8/1992 |
| EP | 0 511 865 A1 | 11/1992 |
| EP | 0 564 409 A1 | 10/1993 |

(List continued on next page.)

OTHER PUBLICATIONS

El–Wakil et al., "Study of the proton magnetic resonance of methoxytamoxifen towards ortho–substitiution", *Chem. Abstr.*, 1992, 116, 255248t.

Geissler, J.F. et al., "Thiazolidine–Diones. Biochemical and Biological Activity of a Novel Class of Tyrosine Protein Kinase Inhibitors", *J. Of Biol. Chem.*, 1990, 265(36), 22255–22261.

Grammaticakis, "Contribution A L–3 Etude de L'Absortion Dans L'Ultraviolet Moyen Et Le Visible Des N–Aroly–Arylamines. IV. 2,3–, 3,4– et 2,4–, dimethoxybenzoylarylamines", *Bulletin DeLa Societa Chemique De France*, 1965, 848–858.

(List continued on next page.)

*Primary Examiner*—Emily Bernhardt
(74) *Attorney, Agent, or Firm*—Woodcock Washburn LLP

(57) ABSTRACT

Fused polycyclic 2-aminopyrimidines of formula (1):

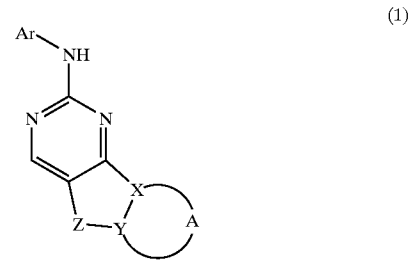

(1)

wherein
Ar is an optionally substituted aromatic or heteroaromatic group;
X is a carbon or nitrogen atom;
Y is a carbon or nitrogen atom;
Z is a linker group;
A together with X and Y forms an optionally substituted monocyclic or bicyclic aromatic or heteroaromatic group;

and the salts, solvates, hydrates and N-oxides thereof are described. The compounds are potent and selective inhibitors of the protein tyrosine kinases $p56^{lck}$ and $p59^{fyn}$ and are of use in the prophylaxis and treatment of immune diseases, hyperproliferative disorders and other diseases in which inappropriate $p56^{lck}$ and/or $p59^{fyn}$ activity is believed to have a role.

11 Claims, No Drawings

U.S. PATENT DOCUMENTS

| | | | |
|---|---|---|---|
| 5,593,997 A | 1/1997 | Dow et al. | 514/258 |
| 5,608,070 A | 3/1997 | Alexander et al. | 546/270 |
| 5,622,977 A | 4/1997 | Warrellow et al. | 514/336 |
| 5,633,257 A | 5/1997 | Warrellow et al. | 514/277 |
| 5,674,880 A | 10/1997 | Boyd et al. | 514/307 |
| 5,691,376 A | 11/1997 | Caggiano et al. | 514/532 |
| 5,693,659 A | 12/1997 | Head et al. | 514/357 |
| 5,698,711 A | 12/1997 | Palfreyman | 549/66 |
| 5,716,967 A | 2/1998 | Kleinman | 514/313 |
| 5,723,460 A | 3/1998 | Warrellow et al. | 514/247 |
| 5,728,708 A | 3/1998 | Zimmermann | 514/275 |
| 5,739,144 A | 4/1998 | Warrellow et al. | 514/277 |
| 5,753,663 A | 5/1998 | Flippin et al. | 514/257 |
| 5,776,958 A | 7/1998 | Warrellow et al. | 514/345 |
| 5,780,477 A | 7/1998 | Head et al. | 514/277 |
| 5,780,478 A | 7/1998 | Alexander et al. | 514/277 |
| 5,786,354 A | 7/1998 | Warrellow et al. | 514/277 |
| 5,798,373 A | 8/1998 | Warrellow | 514/357 |
| 5,849,770 A | 12/1998 | Head et al. | 514/277 |
| 5,851,784 A | 12/1998 | Owens et al. | 435/19 |
| 5,859,034 A | 1/1999 | Warrellow et al. | 514/357 |
| 5,866,593 A | 2/1999 | Warrellow et al. | 514/336 |
| 6,057,329 A | 5/2000 | Davis et al. | 514/267 |
| 6,080,790 A | 6/2000 | Boyd et al. | 514/650 |
| 6,093,716 A | 7/2000 | Davis et al. | 514/253 |
| 6,096,747 A | 8/2000 | Beeley et al. | 514/256 |

FOREIGN PATENT DOCUMENTS

| | | |
|---|---|---|
| FR | 2 313 422 | 12/1976 |
| FR | 2 545 356 A1 | 11/1984 |
| GB | 1 285 932 | 8/1972 |
| GB | 1588639 | 4/1981 |
| JP | 61-112059 | 5/1986 |
| JP | 3-77872 | 4/1991 |
| JP | 3-77923 | 4/1991 |
| WO | WO 87/06576 | 11/1987 |
| WO | WO 91/15451 | 10/1991 |
| WO | WO 91/16892 | 11/1991 |
| WO | WO 92/00968 | 1/1992 |
| WO | WO 92/06085 | 4/1992 |
| WO | WO 92/06963 | 4/1992 |
| WO | WO 92/07567 | 5/1992 |
| WO | WO 92/12961 | 8/1992 |
| WO | WO 92/19594 | 11/1992 |
| WO | WO 92/19602 | 11/1992 |
| WO | WO 93/10118 | 5/1993 |
| WO | WO 93/19748 | 10/1993 |
| WO | WO 94/02465 | 2/1994 |
| WO | WO 94/10118 | 5/1994 |
| WO | WO 94/12461 | 6/1994 |
| WO | WO 94/13661 | 6/1994 |
| WO | WO 94/14742 | 7/1994 |
| WO | WO 94/20446 | 9/1994 |
| WO | WO 94/20455 | 9/1994 |
| WO | WO 95/04046 | 2/1995 |
| WO | WO 95/09847 | 4/1995 |
| WO | WO 95/09851 | 4/1995 |
| WO | WO 95/09852 | 4/1995 |
| WO | WO 95/09853 | 4/1995 |
| WO | WO 95/17386 | 6/1995 |
| WO | WO 95/31451 | 11/1995 |
| WO | WO 95/33727 | 12/1995 |
| WO | WO 95/35281 | 12/1995 |
| WO | WO 95/35283 | 12/1995 |
| WO | WO 96/14843 | 5/1996 |
| WO | WO 97/09297 | 3/1997 |
| WO | WO 99/31073 | 6/1999 |
| WO | WO 00/27825 | 5/2000 |

OTHER PUBLICATIONS

Hanks, S.K. et al., "The eukaryotic protein kinase superfamily: kinase (catalytic) domain structure and classification", *FASEB J.*, 1995, 9, 576–596.

Heaslip et al., "Phosphodiesterase–IV Inhibition, Respiratory Muscle Relaxation and Bronchodilation by WAY–PDA–641", *J. Pharm. Exper. Ther.*, 1993, 268(2), 888–896.

Hirose et al., "Styrene Derivatives and Electrophotpgraphic Photoreceptor Containing Them", *Chem. Abstr.*, 1993, 118, 136183z.

Ishikura, M. et al., "An Efficient Sytnthesis of 3–Heteroarylpyridines via Diethyl–(3–pyridyl)–borane" *Synthesis*, 1984, 936–938.

Iwashita, S. et al., "Signal Transduction System for Growth Factor Receptors Associated with Tyrosine Kinase Activity: Epidermal Growth Factor Receptor Singalling and Its Regulation", *Cellular Signalling*, 1992, 4(2), 123–132.

Karlsson et al., "T–Lymphocyte and Inflammatory Cell Research in Asthma", Joller, G. et al. (eds.), Academic Press, 1993, 323–347.

Chatterjee, A. et al., "Total Synthesis of Ring–C Aromatic 18–Nor Steroid", *Tetrahedron*, 1980, 36, 2513–2519.

Clayton, S.E. et al., "Direct Aromatic tert–Butylation during the Synthesis of Thiochroman–4–ones", *Tetrahedron*, 1993, 49(4), 939–946.

Collins, R.F. et al., "The Chemotherapy of Schistosomiasis. Part IV. Some Ethers of 4–Amino–2–methoxyphenol", *J. Chem. Soc.*, 1961, 1863–1879.

Degani, I. et al., "Cationi etero–aromatici Nota VI—Sintesi di alcuni derivati del perclorato di tiacromilio", *Boll. Sci. Fac. Chim. Ind. Bologna*, 1966, 24(2–3), 75–91 (English Summary Only).

Geissler et al., "Biochemical and Biological Activity of a Novel Class of Tyrosine Protein Kinase Inhibitors", *J. Biol. Chem.*, 1990, 265(36), 22255–22261.

Griffin, R.W. et al., "1–Methyl–7–halo–2–naphthalenecarboxylic Acid Derivatives", *J. Organic Chem.*, 1964, 29(8), 2109–2116.

Gupta, A.S. et al., "Friedel–Crafts Condensation of Ethyl Allylmalonate with Anisole", *Tetrahedron*, 1967, 23, 2481–2490.

Hart et al., "Alkylation of Phenol with a Homoallylic Halide", *J. Am. Chem. Soc.*, 1963, 85, 3269–3273.

Johnson et al., "Identification of Retinoic Acid Receptor β Subtype Specific Agonists", *J. Med. Chem.*, 1996, 39(26), 5027–5030.

Lehmann, J. et al., "Lactones; XIII. Grignard Reaction Followed by Phase–Transfer Oxidation: A Convenient Synthesis of γ,γ–Distributed γ–Butyrolactones from γ–Butyrolactone", *Synthesis*, 1987, 1064–1067 (English abstract only).

Meyers, A.I. et al., "The Synthesis of 2–Pyridones from Cyclic Cyano Ketones. A New Aromatization Procedure for Dihydro–2–pyridones", *J. Org. Chem.*, 1964, 29, 1435–1438.

Sharp, M.J. et al., "Synthetic Connections to the Aromatic Directed Metalation Reaction. Functionalized Aryl Boronic Acids by Ipso Borodesilylation; General Synthesis of Unsymmetrical iphenyls and n–Terphenyls", *Tetrahedron Lett.*, 1987, 28(43), 5093–5096.

Shiori et al., "New Methods and Reagents in Organic Synthesis. 3. Diethyl Phosphorocyanidate: A New Reagent for C–Acylation", *J. Org. Chem.*, 1978, 43, 3631–3632.

Takeuchi, I. et al., "On the Antimocrobial Activity and Syntheses of Carbanilide and Salicylanilide Derivatives", *Chem. Abstr.*, 1983, 98, No. 125577y.

Thompson, W.J. and Gaudino, J., "A General Synthesis of 5–Arylnicotinates" *J. Org. Chem.*, 1984, 49, 5237–5243.

Tominaga et al., "Polarized Ethylenes. IV. Synthesis of Polarized Ethylenes Using Thioamides and Methyl Dithiocarboxylates and Their Application to Syntheses of Pyrazoles, Pyrimidines, Pyrazolo[3,4–d]pyrimidines, and 5–Aza [2.2.3]cyclazines", *J. Het. Chem.*, 1990, 27, 647–660.

Trost and Fleming (eds.), *Comprehensive Organic Synthesis*, Pergamon Press, New York, 1991, 3, 531–541.

Tsutsumi, K. et al., "Preparation of (Dialkoxyphosphinoylmethyl) benzamides and Antihyperlipidemics", *Chem. Abstr.*, 1990, 113, No. 6599a.

Vidal et al., "Electrophilic Amination: Preparation and Use of N–Boc–3–(4–cyanophenyl)oxaziridine, a New Reagent That Transfers a N–Boc Group to N– and C–Nucleophiles", *J. Org. Chem.*, 1993, 58, 4791–4793.

Yeadon et al., "Mechanisms Contributing to Ozone–Induced Bronchial Hyperreactivity in Guinea Pigs", *Pulmonary Pharm.*, 1992, 5, 39–50.

Yoneda et al., "The Antiproliferative Effects of Tyrosine Kinase Inhibitors Tyrphostins on a Human Squamous Cell Carcinoma in Vitro and in Nude Mice" *Cancer Research*, 1991, 51, 4430–4435.

O'Connor et al., "Voltammetry and Controlled Potential Oxidation of 3,4–dimethoxypropenylbenzene at a rotating platinum electrode in unbuffered acetonitrile and in acetonitrile–pyridine solution" *Chem. Abstr.*, 1964, 60(8) #10203.4.

Ohtani, Y. et al., "Studies on Pitch Problems Caused by Pulping and Bleaching of Tropical Woods. XIV. Chemistry of the Aurone Derivatives at the Conventional Bleaching Stages", *Acta Chem. Scand.*, 1982, 613–621.

Pines, J., "Cyclins and cyclin–dependent kinases: take your partners", *TIBS*, 1993, 18, 195–197.

Plé, N. et al., "Metalation of Diazines. XI. Directed Ortho–Lithiation of Fluoropyrimidines and Application to Synthesis of an Azacarboline", *J. Heterocylic Chem.*, 1994, 31, 1311–1315.

Porter et al., "Preparation of 6–phenyl–3–(5–tetrazolyl)pyridin–=(H)–one Derivatives as Cyclic AMP–dependent Protein Kinase Agonists" *Chem. Abstr.*, 1992, 117(9), 90296n.

Ramalingam, Deshmukh and Sattur, "Synthesis and Pharmacology of 2,5–Disubstituted 1,3,4–Zxadiazoles" *J. Indian Chem. Soc.*, 1981, 58(3), 269–271.

Reddy et al., "Inhibition of Breast Cancer Cell Growth in Vitro by a Tyrosine Kinase Inhibitor" *Cancer Research*, 1992, 52, 3636–3641.

Sakakibara, K. et al., "Preparation of N–pyridyl–4–(benzyloxy) benzamides and Cartiotonics", *Chem. Abstr.*, 1988, 108, No. 131583p.

Sánchez, H.I. et al., "Formal Total Synthesis of β–Pipitzol", *Tetrahedron*, 1985, 41(12), 2355–2359.

Schneider et al., "Catechol Estrogens of the 1,1,-2–Triphenylbut–1–ene Type: Relationship Between Structure, Estradiol Receptor Affinity, Estrogenic and Antiestrogenic Properties, and Mammary Tumor Inhibiting Activities" *J. Med. Chem.*, 1986, 29, 1355–1362.

Seitz et al., "Fluorotamoxifen. A Caveat on the Generality of Electrophilic Destannylation" *Chem. Abstr.*, 1989, 111, 57133k.

Kefalas, P. et al., "Signalling by the p60$^{c-src}$ Family of Protein–Tyrosine Kinases", *Int. J. Biochem. Cell Biol.*, 1995, 27(6), 551–563.

Lisle, H. et al., "IL–2–Induced Eosinophilia in the Rat Pleural Cavity: The Effect of Dexamethasone and Indomethacin", *Br. J. Pharmacol.* 1993, 108, 230.

Livi et al., "Cloning and Expression of cDNA for a Human Low–$K_m$3 Rolipram–sensitive Cyclic AMP Phosphodiesterase", *Molecular and Cellular Biol.* 1990, 10(6), 2678–2686.

Manhas et al., "heterocyclic Componds XII. Quinazoline Derivatives as Potential Antifertility Agents(1)" *J. Heterocyclic Chem.*, 1979, 16, 711–715.

Mathison et al., "Synthesis and Hypotensive Properties of Tetrahydroixoquinolines", *J. Med. Chem.*, 1973, 16(4), 332–336.

Meyers, A.J. et al., "Oxazolines. XI. Synthesis of Functionalized Aromatic and Aliphatic Acids. A Useful Protecting Group for Carboxylic Acids Against Grignard and Hydride Reagents", *J. Org. Chem.* 1974, 39(18), 2787–2793.

Mezheritskaya, "Synthesis and properties of carboxonium het=erocyclic systems. VII. Synthesis and properties of 2–benzyl–substituted 1,3–dioxolanium salts", *Chem. Abstr.*, 1980, 93, 95160j, 635.

Mitsunobu, O., "The Use of Diethyl Azodicarboxylate and Triphenylphosphine in Synthesis and Transformation of Natural Products" *Synthesis*, 1981, 1–28.

Miyaura, N. et al., "The Palladium–Catalyzed Cross–Coupling Reaction of Phenylboronic Acid with Haloarenes in the Presence of Bases", *Synth. Comm.*, 1981, 11, 513–519.

Newton A.C., "Protein Kinase C: Structure, Function, Regulation", *J. Biol. Chem.*, 1995, 270(48), 28495–28498.

Nicholson et al., "Differential Modulation of Tissue Function and Therapeutic Potential of Selective Inhibitors of Cyclic Nucleotide Phosphodiesterase Isoenzymes" *TIPS*, 1991, 12, 19–27.

Kroon, A.P., et al., "On the occurrence of an $S_N$(ANRORC) mechanism in the amination of 2–substituted 4–phenylpyrimidines with potassium amide in liquid ammonia," *J. Royal Netherlands Chem. Soc.*, 1974, 93/12, 325–328.

Abstract for Yamato, M. et al., "Chemical Structure and sweet taste of isocoumarin and related compounds. VI", *Chem. Pharm. Bull.*, 1975, 23(12), 3101–3105 (HCAPLUS 1976:99154, 2 pages).

Zimmermann, J. et al., "Phenylamino–Pyrimidine (PAP) Derivatives: A New Class of Potent and Selective Inhibitors of Protein Kinase C (PKC)", *Arch. Pharm.*, 1996, 329(7), 371–376.

Zimmermann, J. et al, "Phenylamino–Pyrimidine (PAP)—Derivatives: A New Class of Potent and Highly Selective PDGF–Receptor Autophosphorylation Inhibitors", *Bioorg. Med. Chem. Lett.*, 1996, 6(11), 1221–1226.

Zimmermann, J. et al., "Potent and Selective Inhibitors of the ABL–Kinase Phenylamino–Pyrimidine (PAP) Derivaties", *Bioorg. Med. Chem. Lett.*, 1997, 7(2), 187–192.

Amers, D.E. et al., "Some Dipyridylalkanes", *J. Chem. Soc.*, 1962, 1475–1481.

Barton, D. et al., "A useful synthesis of pyrroles from nitroolefins", *Tetrahedron*, 1990, 46(21), 7587–7598 (HCAPLUS 1991:163917, 2 pages).

Chemical Abstracts, Registry No. 2732–15–2, prior to 1967, 1 page.

Chemical Abstracts, Registry No. 4593–13–9, prior to 1967, 1 page.

Bortolus et al., "cis–trans Isomerization of azastilbenes photosensitized by biacetyl", *Mol. Photochem.,* 1970, 2(4), 311–321, CAPLUS accession No. 1971–434722, 2 pages.

Fitzgerald, J.J. et al., "Reaction of benzocyclobutene oxides with nitriles: synthesis of hypecumine and other 3–substituted isoquinolines", *Tetrahedron Lett.,* 1994, 35(49), 9191–9194 (HCAPLUS 1995:272292, 2 pages).

Hanna, M.M. et al., "Syntheis and antimicrobial activity of some substituted 3–aryl–5–benzylidene–2–phenyl–4–imidazolone derivatives", *Bull. Fac. Pharm.,* 1994, 32(3), 353–359 (HCAPLUS 1996:586501, 2 pages).

Kaiser et al., "Selective metalations of methylated pyridines and quinolines", *J. Org. Chem.,* 1973, 38(1), 71–75, CAPLUS accession No. 1973–71853, 2 pages.

Nanjo et al., "Preparation of 2–anilinopyrimidines as agricultural fungicides", *Chem. Abstr.,* 1992, 116(21), No. 116:209703q.

Pickett, W.C. et al., "Modulation of Eicosanoid Biosynthesis by Novel Pyridinylpyrimidines", *Ann. N.Y. Acad. Sci.,* 1994, 744, 299–305.

Spada, A.P. et al., "Small Molecule Inhibitors of Tyrosine Kinase Activity", *Exp. Opin. Ther. Patents,* 1995, 5(8), 805–817.

Tollari, S. et al., "Intramolecular amination of olefins. Synthesis of 2–substituted–4–quinolones from 2–nitrochalcones catalyzed by ruthenium", *J. Chem. Soc.,* 1994, 15, 1741–1742 (HCAPLUS 1994:605194, 2 pages).

Yamaguchi, H., "Guanidinobenzene derivatives as anticoagulants", *Chem. Absts.,* 1989, 110, 655 (Abstract No. 94706z).

Aiello, L.P., et al., "Suppression of retinal neovascularization in vivo by inhibition of vascular endothelial growth factor (VEGF) using soluble VEGF–receptor chimeric proteins," *Proc. Natl. Acad. Sci.,* 1995, 92, 10457–10461.

Boschelli, D.H., et al., "Synthesis and tyrosine kinase inhibitory activity of a series of 2–amino–8H–pyrido[2,3–d] pyrimidines: identification of potent, selective platelet–derived growth factor receptor tyrosine kinase inhibitors," *J. Med. Chem.,* 1998, 41, 4365–4377.

Parangi, S., et al., "Antiangiogenic therapy of transgenic mice impairs de novo tumor growth," *Proc. Natl. Acad. Sci.,* 1996, 93, 2002–2007.

Schmidt, H., et al., "A convenient synthesis of 2–substituted 4–amino–5–pyrimidinecarbonitries," *Inst. Of Organic Chemistry,* 1987, 1305–1307.

"The Condensed Chemical Dictionary," Library of Congress Cataloging in Publication Data, Cat. Card No. 76–19024, 1977, p. 25.

Ashton, "Selective Type IV Phosphodiesterase Inhibitors as Antiasthmatic Agents. The Syntheses and Biological Activities of 3–(Cyclopentyloxy)–4–methyoxybenzamides and Analogues", *J. Med. Chem.,* 1994, 37, 1696–1703.

Beavo & Reifsnyder, "Primary Sequence of Cyclic Nucleotide Phosphodiesterase Isozymes and the Design of Selective Inhibitors" *TIPS,* 1990, 11, 150–155.

Buu–Hoi, N.P. et al., "Bromination of Some 1,2,2–Triarylethylenes" *J. of Organic Chemistry,* 1958, 1261–1263.

Buu–Hoi et al., "New Method for the Synthesis of ω,ω–Diarylacetophenones Aminated in the Aromatic Nucleus. Plynitration of Triarylethylenes", *Chem. Abstr.,* 1964, 61(13), 16006h.

Chan, A.C. et al., "The Role of Protein Tyrosine Kinases and Protein Tyrosine Phosphatases in T Cell Antigen Receptor Signal Transduction", *Annu. Rev. Immunol.,* 1994, 12, 555–592.

Chemical Abstracts, "Hypoglycemic Pharmaceuticals Containing Manzammide Derivatives", *Chem. Abstr.,* 1983, 99(6), No. 43558Z.

Chemical Abstracts. Registry Handbook—Number Section. Printed Issues Columbus US *compounds with registry numbers 95992–21–5; 95971–60–1; 90053–37–5; 82668–6; 80395–25–1; 49610–49–3.

Daves, G.D. et al., "Pyrimidines. XIII. 2– and 6– Substituted 4–Pyrimidinecarboxylic Acids", *J. Of Hev. Chem.,* 1964, 1, 130–133.

Dietl, F. et al., "Chinone von Benzo–und Dibenzokronenethern", *Synthesis,* 1985, 626–631.

Dent et al., "Inhibition of eosinophil cyclic nucleotide PDE activity and opsonised zymosan–stimulated respiratory burst by 'type IV'–selective PDE inhibitors", *Br. J. Pharmacol.,* 1991, 103, 1339–1346.

FUSED POLYCYCLIC 2-AMINOPYRIMIDINE DERIVATIVES

This application is a divisional of U.S. application Ser. No. 08/997,174, filed Dec. 22, 1997, now U.S. Pat. No. 6,057,329.

This invention relates to a series of fused polycyclic 2-aminopyrimidines, to processes for their preparation, to pharmaceutical compositions containing them, and to their use in medicine.

Protein kinases participate in the signalling events which control the activation, growth and differentiation of cells in response to extracellular mediators and to changes in the environment. In general, these kinases fall into two groups; those which preferentially phosphorylate serine and/or threonine residues and those which preferentially phosphorylate tyrosine residues [Hanks, S K, Hunter T, FASEB. J. 9, 576–596 (1995)]. The serine/threonine kinases include for example, protein kinase C isoforms [Newton A C, J. Biol. Chem. 270, 28495–28498 (1995)] and a group of cyclin-dependent kinases such as cdc2 [Pines J, Trends in Biochemical Sciences 18, 195–197 (1995)]. The tyrosine kinases include membrane-spanning growth factor receptors such as the epidermal growth factor receptor [Iwashita S and Kobayashi M. Cellular Signalling 4, 123–132 (1992)], and cytosolic non-receptor kinases such as p56$^{lck}$ p59$^{fyn}$ ZAP-70 and csk kinases [Chan C et al Ann. Rev. Immunol. 12, 555–592 (1994)].

Inappropriately high protein kinase activity has been implicated in many diseases resulting from abnormal cellular function. This might arise either directly or indirectly, for example by failure of the proper control mechanisms for the kinase, related for example to mutation, overexpression or inappropriate activation of the enzyme; or by over- or underproduction of cytokines or growth factors also participating in the transduction of signal upstream or downstream of the kinase. In all of these instances, selective inhibition of the action of the kinase might be expected to have a beneficial effect.

We have now found a series of 2-aminopyrimidine derivatives which are potent and selective inhibitors of the protein tyrosine kinases p56$^{lck}$ and p59$^{fyn}$. The compounds are of use in the prophylaxis and treatment of immune diseases, hyperproliferative disorders and other diseases in which inappropriate p56$^{lck}$ and/or p59$^{fyn}$ activity is believed to have a role.

Thus according to one aspect of the invention, we provide a compound of formula (1):

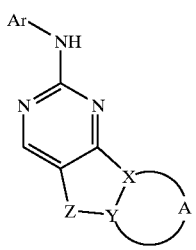

(1)

wherein
Ar is an optionally substituted aromatic or heteroaromatic group;
X is a carbon or nitrogen atom;
Y is a carbon or nitrogen atom;
Z is a linker group;
A together with X and Y forms an optionally substituted monocyclic or bicyclic aromatic or heteroaromatic group;
and the salts, solvates, hydrates and N-oxides thereof.

Aromatic groups represented by the group Ar in compounds of formula (1) include for example mono- or bicyclic $C_{6-12}$ optionally substituted aromatic groups, for example optionally substituted phenyl, 1- or 2-naphthyl, or indenyl groups.

Heteroaromatic groups represented by Ar include for example $C_{1-9}$ optionally substituted heteroaromatic groups containing for example one, two, three or four heteroatoms selected from oxygen, sulphur or nitrogen atoms. In general, the heteroaromatic groups may be for example monocyclic or bicyclic heteroaromatic groups. Monocyclic heteroaromatic groups include for example five- or six-membered heteroaromatic groups containing one, two, three or four heteroatoms selected from oxygen, sulphur or nitrogen atoms. Bicyclic heteroaromatic groups include for example nine- to thirteen-membered heteroaromatic groups containing one, two or more heteroatoms selected from oxygen, sulphur or nitrogen atoms.

Particular examples of heteroaromatic groups represented by Ar include optionally substituted pyrrolyl, furyl, thienyl, imidazolyl, N-methylimidazolyl, N-ethylimidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-thiadiazole, pyridyl, pyrimidinyl, pyridazinyl, pyrazinyl, 1,3,5-triazinyl, 1,2,4-triazinyl, 1,2,3-triazinyl, benzofuryl, isobenzofuryl, benzothienyl, benzotriazolyl, isobenzothienyl, indolyl, isoindolyl, benzimidazolyl, imidazo[1,2-a]pyridyl, benzothiazolyl, benzoxazolyl, quinazolinyl, naphthyridinyl, pyrido[3,4-b]pyridyl, pyrido[3,2-b]pyridyl, pyrido[4,3-b]pyridyl, quinolinyl, isoquinolinyl, tetrazolyl, 5,6,7,8-tetrahydroquinolinyl and 5,6,7,8-tetrahydroisoquinolinyl.

Optional substituents present on the aromatic or heteroaromatic groups represented by Ar include one, two, three or more groups, each represented by the group $R^1$. The substituent $R^1$ may be selected from an atom or group $R^2$ or -Alk($R^2$)$_m$, where $R^2$ is a halogen atom, or an amino (—NH$_2$), substituted amino, nitro, cyano, amidino, hydroxyl (—OH) substituted hydroxyl, formyl, carboxyl (—CO$_2$H), esterified carboxyl, thiol (—SH), substituted thiol, —COR$^3$ (where $R^3$ is an -Alk($R^2$)$_m$, aryl or heteroaryl group), —CSR$^3$, —SO$_3$H, —SO$_2$R$^3$, —SO$_2$NH$_2$, —SO$_2$NHR$^3$, SO$_2$N(R$^3$)$_2$, —CONH$_2$, —CSNH$_2$, —CONHR$^3$, —CSNHR$^3$, —CON(R$^3$)$_2$, —CSN(R$^3$)$_2$, —NHSO$_2$H, —NHSO$_2$R$^3$, —N(SO$_2$R$^3$)$_2$, —NHSO$_2$NH$_2$, —NHSO$_2$NHR$^3$, —NHSO$_2$N(R$^3$)$_2$, —NHCOR$^3$, —NHCSR$^3$, —NHC(O)OR$^3$, aryl or heteroaryl group; Alk is a straight or branched $C_{1-6}$alkylene, $C_{2-6}$alkenylene or $C_{2-6}$alkynylene chain, optionally interrupted by one, two or three —O— or —S— atoms or —S(O)$_n$ (where n is an integer 1 or 2) or —N(R$^4$)— groups (where $R^4$ is a hydrogen atom or $C_{1-6}$alkyl, e.g. methyl or ethyl group); and m is zero or an integer 1, 2 or 3.

When in the group -Alk($R^2$)$_m$ m is an integer 1, 2 or 3, it is to be understood that the substituent or substituents $R^2$ may be present on any suitable carbon atom in -Alk. Where more than one $R^2$ substituent is present these may be the same or different and may be present on the same or different atom in -Alk. Clearly, when m is zero and no substituent $R^2$ is present the alkylene, alkenylene or alkynylene chain represented by Alk becomes an alkyl, alkenyl or alkynyl group.

When $R^2$ is a substituted amino group it may be for example a group —$NHR^3$ [where $R^3$ is as defined above] or a group —$N[R^3]_2$ wherein each $R^3$ group is the same or different.

When $R^2$ is a halogen atom it may be for example a fluorine, chlorine, bromine, or iodine atom.

When $R^2$ is a substituted hydroxyl or substituted thiol group it may be for example a group —$OR^3$ or a —$SR^3$ or —$SC(NH_2+)NH_2$ group respectively.

Esterified carboxyl groups represented by the group $R^2$ include groups of formula —$CO_2Alk^1$ wherein $Alk^1$ is a straight or branched, optionally substituted $C_{1-8}$alkyl group such as a methyl, ethyl, n-propyl, i-propyl, n-butyl, i-butyl, s-butyl or t-butyl group; a $C_{6-12}$aryl$C_{1-8}$alkyl group such as an optionally substituted benzyl, phenylethyl, phenylpropyl, 1-naphthylmethyl or 2-naphthylmethyl group; a $C_{6-12}$aryl group such as an optionally substituted phenyl, 1-naphthyl or 2-naphthyl group; a $C_{6-12}$aryloxy$C_{1-8}$alkyl group such as an optionally substituted phenyloxymethyl, phenyloxyethyl, 1-naphthyl-oxymethyl, or 2-naphthyloxymethyl group; an optionally substituted $C_{1-8}$alkanoyloxy$C_{1-8}$alkyl group, such as a pivaloyloxymethyl, propionyloxyethyl or propionyloxypropyl group; or a $C_{6-12}$aroyloxy$C_{1-8}$alkyl group such as an optionally substituted benzoyloxyethyl or benzoyloxypropyl group. Optional substituents present on the $Alk^1$ group include $R^2$ substituents described above.

When Alk is present in or as a substituent $R^1$ it may be for example a methylene, ethylene, n-propylene, i-propylene, n-butylene, i-butylene, s-butylene, t-butylene, ethenylene, 2-propenylene, 2-butenylene, 3-butenylene, ethynylene, 2-propynylene, 2-butynylene or 3-butynylene chain, optionally interrupted by one, two, or three —O— or —S—, atoms or —S(O)—, —$S(O)_2$— or —$N(R^4)$— groups.

Aryl or heteroaryl groups represented by the groups $R^2$ or $R^3$ include mono- or bicyclic optionally substituted $C_{6-12}$ aromatic or $C_{1-9}$ heteroaromatic groups as described above for the group Ar. The aromatic and heteroaromatic groups may be attached to the remainder of the compound of formula (1) by any carbon or hetero e.g. nitrogen atom as appropriate.

Particularly useful atoms or groups represented by $R^1$ include fluorine, chlorine, bromine or iodine atoms, or $C_{1-6}$alkyl, e.g. methyl or ethyl, $C_{1-6}$alkylamino, e.g. methylamino or ethylamino, $C_{1-6}$hydroxyalkyl, e.g. hydroxymethyl or hydroxyethyl, $C_{1-6}$alkylenethiol e.g. methylenethiol or ethylenethiol, $C_{1-6}$alkoxy, e.g. methoxy or ethoxy, hydroxy$C_{1-6}$alkoxy, e.g. hydroxyethoxy, $C_{5-7}$cycloalkoxy, e.g. cyclopentyloxy, halo$C_{1-6}$alkyl, e.g. trifluoromethyl, $C_{1-6}$alkylamino, e.g. methylamino or ethylamino, amino (—$NH_2$), amino$C_{1-6}$alkyl, e.g. aminomethyl or aminoethyl, $C_{1-6}$dialkylamino, e.g. dimethylamino or diethylamino, $C_{1-6}$alkylamino$C_{1-6}$alkyl, e.g. ethylaminoethyl, $C_{1-6}$dialkylamino$C_{1-6}$alkyl, e.g. diethylaminoethyl, amino$C_{1-6}$alkoxy, e.g. aminoethoxy, $C_{1-6}$alkylamino$C_{1-6}$alkoxy, e.g. methylaminoethoxy, $C_{1-6}$dialkylamino$C_{1-6}$alkoxy, e.g. dimethylaminoethoxy, diethylaminoethoxy, isopropylaminoethoxy, or dimethylaminopropoxy, imido, such as phthalimido or naphthalimido, e.g. 1,8-naphthalimido, 1,1,3-trioxobenzo[d]thiazolidino, nitro, cyano, amidino, hydroxyl (—OH), formyl (HC(O)—), carboxyl (—$CO_2H$), —$CO_2Alk^1$ (where $Alk^1$ is as defined above), $C_{1-6}$alkanoyl e.g. acetyl, thiol (—SH), thio$C_{1-6}$alkyl, e.g. thiomethyl or thioethyl, —$SC(NH_2+)NH_2$, sulfo (—$SO_3H$), $C_{1-6}$alkylsulphonyl, e.g. methyl-sulphonyl, aminosulphonyl (—$SO_2NH_2$), $C_{1-6}$alkylaminosulphonyl, e.g. methylaninosulphonyl or ethylaminosulphonyl, $C_{1-6}$dialkylaminosulphonyl, e.g. dimethylaminosulphonyl or diethylaminosulphonyl, phenylaminosulphonyl, carboxamido (—$CONH_2$), $C_{1-6}$alkylaminocarbonyl, e.g. methylaminocarbonyl or ethylaminocarbonyl, $C_{1-6}$dialkylaminocarbonyl, e.g. dimethylaminocarbonyl or diethylaminocarbonyl, amino$C_{1-6}$alkylaminocarbonyl, e.g. aminoethylaminocarbonyl, $C_{1-6}$dialkylaminb$C_{1-6}$alkylamino-carbonyl, e.g. diethylaminoethylaminocarbonyl, —CONHC(=NH)$NH_2$ sulphonylamino (—$NHSO_2H$), $C_{1-6}$alkylsulphonyl-amino, e.g. methylsulphonylamino or ethylsulphonylamino, $C_{1-6}$dialkylsulphonylamino, e.g. dimethylsulphonylamino or diethylsulphonylamino, optionally substituted phenylsulphonylamino, e.g. 2-, 3- or 4-substituted phenylsulphonylamino such as 2-nitrophenylsulphonylamino, amino-sulphonylamino (—$NHSO_2NH_2$), $C_{1-6}$alkylaminosulphonylamino, e.g. methylaminosulphonylamino or ethylaminosulphonylamino, $C_{1-6}$dialkylaminosulphonylamnino, e.g. dimethylaminosulphonylamino or diethylaminosulphonylamino, phenylaminosulphonylamino, $C_{1-6}$alkanoylamino, e.g. acetylamino, amino$C_{1-6}$alkanoylamino e.g. aminoacetylamino, $C_{1-6}$dialkylamino$C_{1-6}$alkanoylamino, e.g. dimethylaminoacetylamino, $C_{1-6}$alkanoylamino$C_{1-6}$alkyl, e.g. acetylaminomethyl, $C_{1-6}$alkanoylamino$C_{1-6}$alkylamino, e.g. acetamidoethylamino, amino$C_{1-6}$alkoxycarbonylamino, e.g. methoxycarbonylamino, ethoxycarbonylamino or t-butoxycarbonylamino or optionally substituted benzyloxy, benzyloxycarbonylamino or benzyloxycarbonylamino$C_{1-6}$alkyl e.g. benzyloxycarbonylaminoethyl groups.

Where desired, two $R^1$ substituents may be linked together to form a cyclic group such as a cyclic ether, e.g. a $C_{1-6}$alkylenedioxy group such as methylenedioxy or ethylenedioxy.

It will be appreciated that where two or more $R^1$ substituents are present, these need not necessarily be the same atoms and/or groups. In general, the $R^1$ substituent(s) may be present at any available ring position in the aromatic or heteroaromatic group.

Linker groups represented by the group Z in compounds of formula (1) include groups of formula -$(Alk^2)_r(L^1)_s(L^2)_t(Alk^3)_u$— where $Alk^2$ and $Alk^3$ which may be the same or different is each an optionally substituted straight or branched $C_{1-6}$alkylene, $C_{2-6}$alkenylene or $C_{2-6}$alkynylene chain, $L^1$ and $L^2$ is each an —O— or —S— atom or a —S(O)—, —$S(O)_2$—, —$N(R^4)$—, —C(O)—, —C(S)—, —$C(NR^4)$—, —$CON(R^4)$—, —$CSN(R^4)$—, —$N(R^4)SO$—, —$N(R^4)SO_2$—, —$N(R^4)SO_2N(R^4)$—, —$N(R^4)SON(R^4)$, or —$N(R^4)CON(R^4)$ group and r, s, t and u which may the the same or different is each zero or the integer 1, provided that when one of r, s, t or u is zero at least one of the remainder is the integer 1. It will be appreciated that when two or more L atoms or groups are present, such atoms or groups are adjacent to one another and, for example form a chain —$N(R^4)C(NR^4)$—$N(R^4)$ or —$OCON(R^4)$—.

The heteroatoms which may interrupt the $Alk^2$ or $Alk^3$ chains include for example —O— or —S— atoms. Particular heteroatom-containing groups which may interrupt $Alk^2$ or $Alk^3$ include oxygen-, sulphur- or nitrogen-containing groups such as —S(O)—, —$S(O)_2$, —$N(R^4)$, Optional substituents which may be present on $Alk^2$ or $Alk^3$ chains include one, two or more halogen atoms such as chlorine, fluorine, bromine or iodine atoms and $C_{1-3}$alkyl groups such as methyl or ethyl groups.

Particular examples of linker groups Z include optionally substituted —$CH_2$—, —$(CH_2)_2$—, or —$(CH_2)_3$— chains, especially —$CH_2$—$CH(CH_3)$—, —$CH(CH_3)CH_2$—, —CH$_2$C(CH$_3$)$_2$— or —C(CH$_3$)$_2$CH$_2$— chains, —CH$_2$S—, —CH(CH$_3$)S—, —C(CH$_3$)$_2$S—, —SCH$_2$, —CH$_2$O—, —OCH$_2$— or —CH=CH— chains.

When A together with X and Y in compounds of formula (1) form an optionally substituted monocyclic or bicyclic aromatic group [i.e. when X and Y is each a carbon atom] the aromatic group may be an optionally substituted monocyclic or bicyclic C$_{6-12}$aromatic group such as an optionally substituted phenyl, 1- or 2- naphthyl or indenyl group.

In compounds of formula (1) when A together with X and Y from an optionally substituted monocyclic or bicyclic heteroaromatic group [i.e. X and Y is each a -carbon or nitrogen atom], the heteroaromatic group may be an optionally substituted monocyclic or bicyclic C$_{1-9}$heteroaromatic group containing for example one, two, three or four heteroatoms selected from oxygen, sulphur or nitrogen atoms. Monocyclic heteroaromatic groups include for example five- or six-membered heteroaromatic groups containing one, two, three or four heteroatoms selected from oxygen, sulphur or nitrogen atoms. Bicyclic heteroaromatic groups include for example nine- to thirteen-membered heteroaromatic groups containing one, two or more heteroatoms selected from oxygen, sulphur or nitrogen atoms.

Particular examples of heteroaromatic groups represented by A, X and Y together include optionally substituted pyrrolyl, furyl, thienyl, imidazolyl, N-methylimidazolyl, N-ethyl-imidazolyl, oxazolyl, isoxazolyl, thiazolyl, isothiazolyl, pyrazolyl, 1,2,3-triazolyl, 1,2,4-triazolyl, 1,2, 3-oxadiazolyl, 1,2,4-oxadiazolyl, 1,2,5-oxadiazolyl, 1,3,4-oxadiazolyl, 1,3,4-thiadiazole, pyridyl, pyrimidinyl, pyridazinyl, pyrazinyl, 1,3,5-triazinyl, 1,2,4-triazinyl, 1,2,3-triazinyl, benzofuryl, isobenzofuryl, benzothienyl, benzotriazolyl, isobenzothienyl, indolyl, isoindolyl, benzimidazolyl, imidazo[1,2-a]pyridyl, benzothiazolyl, benzoxazolyl, quinazolinyl, naphthyridinyl, pyrido[3,4-b]pyridyl, pyrido[3,2-b]pyridyl, pyrido[4,3-b]pyridyl, quinolinyl, isoquinolinyl, tetrazolyl, 5,6,7,8-tetrahydroquinolinyl and 5,6,7,8-tetrahydroisoquinolinyl.

Optional substitutents which may be present on aromatic or heteroaromatic groups represented by A, X and Y together include one, two, three or more substituents selected from fluorine, chlorine, bromine or iodine atoms, or C$_{1-6}$alkyl, e.g. methyl or ethyl, C$_{1-6}$alkylamino, e.g. methylamino or ethylamino, C$_{1-6}$hydroxyalkyl, e.g. hydroxymethyl or hydroxyethyl, C$_{1-6}$alkylenethiol e.g. methylenethiol or ethylenethiol, C$_{1-6}$alkoxy, e.g. methoxy or ethoxy, haloC$_{1-6}$alkyl, e.g. trifluoromethyl, C$_{1-6}$alkylamino, e.g. methylamino or ethylamino, amino (—NH$_2$), aminoC$_{1-6}$alkyl, e.g. aminomethyl or aminoethyl, C$_{1-6}$dialkylamino, e.g. dimethylamino or diethylamino, aminoC$_{1-6}$alkoxy, e.g. aminoethoxy, C$_{1-6}$alkylaminoC$_{1-6}$alkoxy, e.g. methylaminoethoxy, C$_{1-6}$dialkylaminoC$_{1-6}$alkoxy, e.g. dimethylaminoethoxy, diethylaminoethoxy or dimethylaminopropoxy, nitro, cyano, hydroxyl (—OH), formyl (HC(O)—), carboxyl (—CO$_2$H), —CO$_2$Alk$^1$ (where Alk$^1$ is as defined above), C$_{1-6}$alkanoyl e.g. acetyl, thiol (—SH), thioC$_{1-6}$alkyl, e.g. thiomethyl or thioethyl, —SC(NH$_2$+)NH$_2$, sulfo (—SO$_3$H), C$_{1-6}$alkylsulphonyl, e.g. methylsulphonyl, aminosulphonyl (—SO$_2$NH$_2$), C$_{1-6}$alkylaminosulphonyl, e.g. methylaminosulphonyl or ethylaminosulphonyl, C,dialkylaminosulphonyl, e.g. dimethylaminosulphonyl or diethylaminosulphonyl, phenylaminosulphonyl, carboxamido (—CONH$_2$), C$_{1-6}$alkylaminocarbonyl, e.g. methylaminocarbonyl or ethylaminocarbonyl, C$_{1-6}$ dialkylaminocarbonyl, e.g. dimethylaminocarbonyl or diethylaminocarbonyl, sulphonylamino (—NHSO$_2$H), C$_{1-6}$alkylsulphonylamino, e.g. methylsulphonylamino or ethylsulphonylamino, C$_{1-6}$dialkylsulphonylamino, e.g. dimethylsulphonylamino or diethylsulphonylamino, optionally substituted phenylsulphonylamino, e.g. 2-, 3- or 4-substituted phenylsulphonylamino such as 2-nitrophenylsulphonylamino, aminosulphonylamino (—NHSO$_2$NH$_2$), C$_{1-6}$alkylaminosulphonylamino, e.g. methylaminosulphonylamino or ethylaminosulphonylamino, C$_{1-6}$dialkylaminosulphonylamino, e.g. dimethylaminosulphonylamino or diethylaminosulphonylamino, phenylaminosulphonylamino, C$_{1-6}$alkanoylamino, e.g. acetylamino, C$_{1-6}$alkanoylaminoC$_{1-6}$alkyl, e.g. acetylaminomethyl, aminocarbonylamino (—NHCONH$_2$), C$_{1-6}$alkylaminocarbonylamino, e.g. methylaminocarbonylamino or ethylaminocarbonylamino, C$_{1-6}$dialkylaminocarbonylamino, e.g. dimethylaminoarbonylamino or diethylaminocarbonylamino, C$_{1-6}$alkoxycarbonylamino, e.g. methoxycarbonylamino, ethoxycarbonylamino or t-butoxycarbonylamino groups.

In general the substituent(s) may be present on any available ring atom in the aromatic or heteroaromatic group. Where desired, two of these substituents may be linked together to form a cyclic group such as a cyclic ether, e.g. a C$_{1-6}$alkylenedioxy group such as a methylenedioxy or ethylenedioxy group.

The presence of certain substituents in the compounds of formula (1) may enable salts of the compounds to be formed. Suitable salts include pharmaceutically acceptable salts, for example acid addition salts derived from inorganic or organic acids, and salts derived from inorganic and organic bases.

Acid addition salts include hydrochlorides, hydrobromides, hydroiodides, alkylsulphonates, e.g. methanesulphonates, ethanesulphonates, or isethionates, arylsulphonates, e.g. p-toluenesulphonates, besylates or napsylates, phosphates, sulphates, hydrogen sulphates, acetates, trifluoroacetates, propionates, citrates, maleates, fumarates, malonates, succinates, lactates, oxalates, tartrates and benzoates.

Salts derived from inorganic or organic bases include alkali metal salts such as sodium or potassium salts, alkaline earth metal salts such as magnesium or calcium salts, and organic amine salts such as morpholine, piperidine, dimethylamine or diethylamine salts.

Particularly useful salts of compounds according to the invention include pharmaceutically acceptable salts, especially acid addition pharmaceutically acceptable salts.

It will be appreciated that where compounds of formula (1) exist as geometrical isomers and/or enantiomers or diasteromers then the invention extends to all such isomers of the compounds of formula (1), and to mixtures thereof, including racemates.

One particularly useful group of compounds according to the invention is that wherein Ar is an optionally substituted aromatic group. Particularly useful compounds of this type are those wherein Ar is an optionally substituted phenyl group. In compounds of this type Ar may be in particular a phenyl group or a phenyl group substituted by one, two, three or more R$^1$ groups as defined herein. Especially useful Ar groups include phenyl or monosubstituted phenyl groups where the substituent is a R$^1$ group as defined herein and is particularly an alkylaminoethoxy or dialkylaminoethoxy group especially a methylaminoethoxy or dimethylaminoethoxy group.

In another preference, A together with X and Y is preferably an optionally substituted phenyl group, the optional substituents being those previously generally and particularly described above. In one preference, A together with X and Y is a phenyl or monosubstituted phenyl group. Particularly useful substituents include methoxy groups.

Z in compounds of formula (1) is preferably an optionally substituted —(CH$_2$)$_2$— group. Particular examples of groups of this type include —(CH$_2$)$_2$—, —CH$_2$CH(CH$_3$)— or —CH$_2$C(CH$_3$)$_2$— groups.

Particularly useful compounds according to the invention include those described in the Examples hereinafter and especially include:

N-[4-(2-Dimethylaminoethoxy)phenyl]-9-methoxy-benzo[h]-5,6-dihydroquinazoline-2-amine;
6,6-Dimethyl-N-(4-[2-dimethylaminoethoxy]phenyl)-benzo[h]-5,6-dihydroquinazoline-2-amine;
6,6-Dimethyl-N-(4-[2-dimethylaminoethoxy]phenyl)-9-methoxy-benzo[h]-5,6-dihydroquinazoline-2-amine;
N-[4-(2-Dimethylaminoethoxy)phenyl]-9-methoxy-6-methyl-benzo[h]-5,6-dihydroquinazoline-2-amine;

and the salts, solvates, hydrates and N-oxides thereof.

Compounds according to the invention are potent and selective inhibitors of the protein tyrosine kinases p56$^{lck}$ and p59$^{fyn}$. In particular, compounds of the invention inhibit these enzymes at concentrations at which they have little or no useful inhibitory action on other protein kinases, in particular ZAP-70, protein kinase C and Csk kinases. The ability of the compounds to act in this way may be simply determined by the tests described in the Examples hereinafter.

The compounds according to the invention are thus of particular use in the prophylaxis and treatment of autoimmune diseases such as rheumatoid arthritis, multiple sclerosis and systemic lupus erythematosus, in transplant rejection, in graft v host disease, in hyperproliferative disorders such as tumours and psoriasis, and in diseases such as asthma and inflammatory bowel disease.

For the prophylaxis or treatment of disease the compounds according to the invention may be administered as pharmaceutical compositions, and according to a further aspect of the invention we provide a pharmaceutical composition which comprises a compound of formula (1) together with one or more pharmaceutically acceptable carriers, excipients or diluents.

Pharmaceutical compositions according to the invention may take a form suitable for oral, buccal, parenteral, nasal, topical or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles and preservatives. The preparations may also contain buffer salts, flavouring, colouring and sweetening agents as appropriate.

Preparations for oral administration may be suitably formulated to give controlled release of the active compound.

For buccal administration the compositions may take the form of tablets or lozenges formulated in conventional manner.

The compounds for formula (1) may be formulated for parenteral administration by injection e.g. by bolus injection or infusion. Formulations for injection may be presented in unit dosage form, e.g. in glass ampoule or multi dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds of formula (1) may also be formulated as a depot preparation. Such long acting formulations may be administered by implantation or by intramuscular. injection.

For nasal administration or administration by inhalation, the compounds for use according to the present invention are conveniently delivered in the form of an aerosol spray presentation for pressurised packs or a nebuliser, with the use of suitable propellant, e.g. dichlorodifluoromethane, trichlorofluoromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

The quantity of a compound of the invention required for the prophylaxis or treatment of a particular condition will vary depending on the compound chosen, and the condition of the patient to be treated. In general, however, daily dosages may range from around 100 ng/kg to 100 mg/kg e:g. around 0.01 mg/kg to 40 mg/kg body weight for oral or buccal administration, from around 10 ng/kg to 50 mg/kg body weight for parenteral administration and around 0.05 mg to around 1000 mg e.g. around 0.5 mg to around 1000 mg for nasal administration or administration by inhalation or insufflation.

The compounds of the invention may be prepared by a number of processes as generally described below and more specifically in the Examples hereinafter. In the following process description, the symbols Ar, X, Y, Z and A when used in the formulae depicted are to be understood to represent those groups described above in relation to formula (1) unless otherwise indicated. In the reactions described below, it may be necessary to protect reactive functional groups, for example hydroxy, amino, thio or carboxy groups, where these are desired in the final product, to avoid their unwanted participation in the reactions. Conventional protecting groups may be used in accordance with standard practice [see, for example, Green, T. W. in "Protective Groups in Organic Synthesis", John Wiley and Sons, 1991]. In some instances, deprotection may be the final step in the synthesis of a compound of formula (1) and the processes according to the invention described hereinafter are to be understood to extend to such removal of protecting groups.

Thus according to a further aspect of the invention, a compound of formula (1) may be prepared by reaction of a guanidine of formula (2):

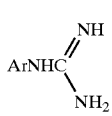

(2)

or a salt thereof
with an enaminone of formula (3):

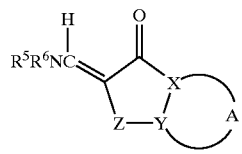

(3)

where $R^5$ and $R^6$, which may be the same or different is each a $C_{1-6}$ alkyl group.

The reaction may be performed in a solvent, for example a protic solvent such as an alcohol, e.g. ethanol, methoxyethanol, propanol or isopropanol, optionally in the presence of a base e.g. an alkali metal base, such as sodium hydroxide or potassium carbonate, at an elevated temperature, e.g. the reflux temperature.

Salts of the compounds of formula (2) include acid salts such as inorganic acid salts e.g. hydrochlorides, nitrates or carbonates.

Intermediate guanidines of formula (2) may be prepared by reaction of the corresponding amine $ArNH_2$ with cyanamide at an elevated temperature. The reaction may be performed in a solvent such as ethanol at an elevated temperature, e.g. up to the reflux temperature. Where it is desired to obtain a salt of a guanidine of formula (2), the reaction may be performed in the presence of a concentrated acid, e.g. hydrochloric or nitric acid.

The amines $ArNH_2$ are either known compounds or may be obtained by conventional procedures, for example by hydrogenation of the corresponding nitro derivatives using for example hydrogen in the presence of a metal catalyst in a suitable solvent, for example as more particularly described in the interconversion reactions discussed below. The nitrobenzenes for this particular reaction are either known compounds or may be prepared using similar methods to those used for the preparation of the known compounds.

Intermediate enaminones of formula (3) are either known compounds or may be prepared by reaction of a ketone of formula (4):

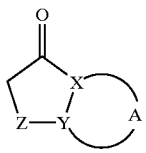

(4)

with an acetal $(R^5)(R^6)NCH(OCH_3)_2$ at an elevated temperature. The starting materials for this reaction are either known compounds of may be prepared by methods analogous to those used for the preparation of the known compounds using simple chemical manipulations, for example as described in the Examples hereinafter.

In another process according to the invention, compounds of formula (1) may be prepared by reaction of an amine $ArNH_2$ with a compound of formula (5):

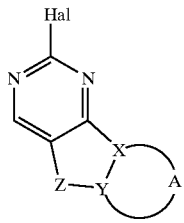

(5)

where Hal is a halogen atom such as a chlorine atom.

The reaction may be performed at an elevated temperature, for example the reflux temperature, where necessary in the presence of a solvent, for example a ketone such as acetone, an alcohol such as ethanol or 2-ethoxyethanol or an aromatic hydrocarbon such as toluene, optionally in the presence of a base, for example an organic amine such as triethylamine or pyridine, or an acid, for example an inorganic acid such as hydrochloric acid.

The intermediates of formula (5) may be prepared by heating the corresponding alcohols of formula (6):

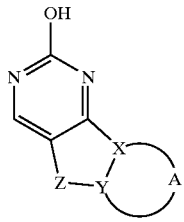

(6)

with a phosphorous oxyhalide in a solvent such as dimethylformamide at an elevated temperature such as the reflux temperature.

Alcohols of formula (6) may be obtained from the corresponding amines of formula (7):

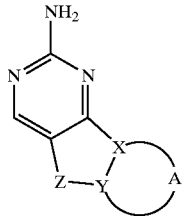

(7)

by reaction with a nitrite, e.g. sodium nitrite in an aqueous acidic solution followed by treatment with a base, for example an inorganic base such as sodium hydroxide or an ammonium base such as aqueous ammonia.

Amines of formula (7) may be prepared by reaction of an enaminone of formula (3) with guanidine or a salt thereof using the reaction conditions described above for the preparation of compounds of formula (1) from compounds of formula (3).

Compounds of formula (1) may also be prepared by interconversion of other compounds of formula (1) and it is to be understood that the invention extends to such interconversion processes. Thus, for example, standard substitution approaches employing for example alkylation, arylation, acylation, thioacylation, sulphonylation, formylation or coupling reactions may be used to add new substitutents to and/or extend existing substituents in compounds of formula (1). Alternatively existing substituents in compounds of formula (1) may be modified by for example oxidation, reduction or cleavage reactions to yield other compounds of formula (1).

The following describes in general terms a number of approaches which can be employed to modify existing Ar and aromatic or heteroaromatic groups represented by groups X, Y and A together in compounds of formula (1). It will be appreciated that each of these reactions will only be possible where one or more appropriate functional groups exist in the compound of formula (1).

Thus, for example alkylation or arylation of a compound of formula (1), for example to introduce a group $Alk(R^5)_m$ or $R^5$ where $R^5$ is an aryl group may be achieved by reaction of the compound with a reagent $(R^5)_mAlkL^2$ or $R^5L^2$, where $L^2$ is a leaving group.

Leaving groups represented by $L^2$ include halogen atoms such as iodine, chlorine or bromine atoms or sulphonyloxy groups such as alkyl- or arylsulphonyloxy groups, e.g. methylsulphonyloxy or p-toluenesulphonyloxy.

The alkylation or arylation reaction may be carried out in the presence of a base, e.g. an inorganic base such as a carbonate, e.g. caesium or potassium carbonate, an alkoxide, e.g. potassium t-butoxide, or a hydride, e.g. sodium hydride, in a dipolar aprotic solvent such as an amide, e.g. a substituted amide such as dimethylformamide or an ether, e.g. a cyclic ether such as tetrahydrofuran, at around 0° C. to around 120° C.

In another general example of an interconversion process, a compound of formula (1) may be acylated or thioacylated, for example to introduce a group $—C(O)R^3$ or $—C(S)R^3$. The reaction may be performed for example with an acyl or thioacyl halide or anhydride in the presence of a base, such as a tertiary amine e.g. triethylamine in a solvent such as a halogenated hydrocarbon, e.g. dichloromethane at for example ambient temperature, or by reaction with a thioester in an inert solvent such as tetrahydrofuran at a low temperature such as around 0° C.

Compounds of formula (1) may be prepared in another general iriterconversion reaction by sulphonylation, for example by reaction of the compound with a reagent $R^2S$ $(O)L^2$ or $R^2SO_2L^2$ where $L^2$ is a leaving group as described above in the presence of a base, for example an inorganic base such as sodium hydride in a solvent such as an amide, e.g. a substituted amide such as dimethylformamide at for example ambient temperature. The reaction may in particular be performed with compounds of formula (1) in which Ar and/or X, Y and A together possesses a primary or secondary amino group.

In further examples of interconversion reactions according to the invention compounds of formula (1) may be prepared from other compounds of formula (1) by modification of existing functional groups in the latter.

Thus in one example, ester groups $—CO_2Alk^1$ in compounds of formula (1) may be converted to the corresponding acid $[—CO_2H]$ by acid- or base-catalysed hydrolysis depending on the nature of the group $Alk^1$. Acid- or base-catalysed hydrolysis. may be achieved for example by treatment with an organic or inorganic acid, e.g. trifluoroacetic acid in an aqueous solvent or a mineral acid such as hydrochloric acid in a solvent such as dioxan or an alkali metal hydroxide, e.g. lithium hydroxide in an aqueous alcohol, e.g. aqueous methanol.

In a second example, $—OR^3$ [where $R^3$ represents an alkyl group such as methyl group] groups in compounds of formula (1) may be cleaved to the corresponding alcohol $—OH$ by reaction with boron tribromide in a solvent such as a halogenated hydrocarbon, e.g. dichloromethane at a low temperature, e.g. around −78° C.

Alcohol [—OH] groups may also be obtained by hydrogenation of a corresponding $—OCH_2Ar$ group using a metal catalyst, for example palladium on a support such as carbon in a solvent such as ethanol in the presence of ammonium formate, cyclohexadiene or hydrogen, from around ambient to the reflux temperature. In another example, —OH groups may be generated from the corresponding ester $[—CO_2Alk^1]$ or aldehyde [—CHO] by reduction, using for example a complex metal hydride such as lithium aluminium hydride or sodium borohydride in a solvent such as methanol.

In another example, alcohol —OH groups in compounds of formula (1) may be converted to a corresponding $—OR^3$ group by coupling with a reagent $R^3OH$ in a solvent such as tetrahydrofuran in the presence of a phosphine, e.g. triphenylphosphine and an activator such as diethyl-, diisopropyl-, or dimethylazodicarboxylate.

Aminosulphonylamino $[—NHSO_2NH_2]$ groups in compounds of formula (1) may be obtained, in another example, by reaction of a corresponding amine $[—NH_2]$ with sulphamide in, the presence of an organic base such as pyridine at an elevated temperature, e.g. the reflux temperature.

In another example of an interconversion reaction, amine ($—NH_2$) groups may be alkylated using a reductive alkylation process employing an aldehyde and a borohydride, for example sodium triacetoxyborohyride or sodium cyanoborohydride, in a solvent such as a halogenated hydrocarbon, e.g. dichloromethane, a ketone such as acetone, or an alcohol, e.g. ethanol, Where necessary in the presence of an acid such as acetic acid at around ambient temperature.

In a further example, amine $[—NH_2]$ groups in compounds of formula (1) may be obtained by hydrolysis from a corresponding imide by reaction with hydrazine in a solvent such as an alcohol, e.g. ethanol at ambient temperature.

In another example, a nitro $[—NO_2]$ group may be reduced to an amine $[—NH_2]$, for example by catalytic hydrogenation using for example hydrogen in the presence of a metal catalyst, for example palladium on a support such as carbon in a solvent such as an ether, e.g. tetrahydrofuran or an alcohol e.g. methanol, or by chemical reduction using for example a metal, e.g. tin or iron, in the presence of an acid such as hydrochloric acid.

In a further example, amide $[—CONHR^3]$ groups in compounds of formula (1) may be obtained by coupling a corresponding acid $[—CO_2H]$ or an active derivative thereof, e.g. an acid anhydride, ester, imide or halide, with an amine $R^3NH_2$. The coupling reaction may be performed using standard conditions for reactions of this type. Thus for example the reaction may be carried out in a solvent, for example an inert organic solvent such as an amide, e.g. a substituted amide such as dimethylformamide, at a low temperature, e.g. −30° C. to ambient temperature, optionally in the presence of a base, e.g. an organic base such as a cyclic amine, e.g. N-methylmorpholine, and where necessary in the presence of a condensing agent, for example a diimide such as 1-(3-dimethylaminopropyl)-3-ethylcarbodiimide.

Aromatic halogen substituents in compounds of the invention may be subjected to halogen-metal exchange with a base, for example a lithium base such as n-butyl or t-butyl lithium, optionally at a low temperature, e.g. around −78° C., in a solvent such as tetrahydrofuran and then quenched with an electrophile to introduce a desired substituent. Thus, for example, a formyl group may be introduced by using dimethylformamide as the electrophile; a thiomethyl group may be introduced by using dimethyidisulphide as the electrophile.

In another example, sulphur atoms in compounds of the invention, for example when present in the linker group Z, may be oxidised to the corresponding sulphoxide using an oxidising agent such as a peroxy acid, e.g. 3-chloroperoxybenzoic acid, in an inert solvent such as a halogenated hydrocarbon, e.g. dichloromethane, at around ambient temperature.

In a still further example, compounds of the invention may be prepared by aromatisation of a corresponding hydroaromatic compound. Thus, for example, a compound of formula (1) wherein the linker group Z is a —$CH_2$—$CH_2$— chain may be treated with a hydrogen acceptor, for example a quinone such as 2,3-dichloro-5,6-dicyano-1,4-benzoquinone in a solvent such as an ether, e.g. a cyclic ether such as dioxane, at an elevated temperature, e.g. the reflux temperature, to yield a corresponding compound in which Z is a —CH=CH— chain.

N'-oxides of compounds of formula (1) may be prepared for example by oxidation of the corresponding nitrogen base using an oxidising agent such as hydrogen peroxide in the presence of an acid such as acetic acid, at an elevated temperature, for example around 70° C. to 80° C., or alternatively by reaction with a peracid such as peracetic acid in a solvent, e.g. dichloromethane, at ambient temperature.

The following Examples illustrate the invention.

All temperatures are in °C. The following abbreviations are used:

THF—tetrahydrofuran; DMF—dimethylformamide; DMSO—dimethylsulphoxide; DMAP—dimethylaminopyridine.

EXAMPLE 1

N-(3,4,5-Trimethoxyphenyl)benzo[h]-5,6-dihydroquinazoline-2-amine

Powdered sodium hydroxide (153 mg, 3.8 mmol) was added to a solution of 3,4,5-trimethoxyphenylguanidinium nitrate (1.0 g, 3.5 mmol) and 3,4-dihydro-2-(dimethylaminomethylene)-1(2 H)-naphthalen one (1.07 g, 5.3 mmol) in propan-2-ol (20 ml) and the mixture refluxed for 3.5 h. On cooling to room temperature the resultant precipitate was collected by filtration, washed with propan-2-ol, water and diethyl ether to give the title compound as a pale green solid (341 mg) m.p. 214–215°. δH (d⁶ DMSO) 9.37 (1H, s), 8.38 (1H, s), 8.25 (1H, dd, J7.1, 1.9 Hz), 7.41 (1H, td, J 6.6, 2.1 Hz), 7.46–7.32 (2H, m), 7.31 (2H, s), 3.79 (6H, s), 3.62 (3H, s), 2.90 (2H, m) and 2.80 (2H, m). MS (ES⁺) 364 (MH⁺, 100%).

The guanidine starting material was prepared by heating a mixture of 3,4,5-trimethoxyaniline (5.49 g, 30.0 mmol), cyanamide [Aldrich, 50% solution in water w/v] (3.50 ml, 345.0 mmol) and concentrated nitric acid (2.10 ml, 300 mmol) in ethanol (30 ml). The solid which formed on cooling to room temperature was collected by filtration, washed with ethanol and dried in vacuo to give 3,4,5-trimethoxyphenylguanidinium nitrate as a grey solid (4.60 g) m.p.187°. δH (d⁶ DMSO) 9.46 (1H, s), 7.27 (4H, br s), 6.54 (2H, s), 3.77 (6H, s) and 3.65 (3H, s).

The 3,4-dihydro-2-(dimethylaminomethylene)-1(2H)-naphthalenone starting material was prepared by heating a mixture of α-tetralone (5.85 g, 40 mmol) and N,N-dimethylformamide dimethyl acetal (32 ml, 240 mmol) at 110° for 3 h. The reaction was allowed to cool to room temperature and excess reagent removed in vacuo to give a thick oil. This crude material was subjected to column chromatography (silica, 5% methanol in $CH_2Cl_2$) to afford the desired product as a thick orange oil (3.50 g). δH (CDCl₃) 8.02 (1 H, dd, J 7.7, 1.5 Hz), 7.72 (1 H, s), 7.36 (1 H, td, J 7.3, 1.6 Hz), 7.28 (1H, td, J 7.6, 1.5 Hz), 7.15 (1H, dm, J 7.3 Hz), 3.12 (6H, s) and 2.98–2.80 (4H, m). MS (ES⁺) 202 (MH⁺, 90%), 175 (MH⁺–HCN, 100%).

The following compounds of Examples 2–37 were prepared in a similar manner from the appropriate guanidine and naphthalenone/indanone starting materials. The starting materials are either known compounds or were prepared using methods analogous to to those described in Example 1.

EXAMPLE 2

7-Methoxy-N-(3,4,5-trimethoxyphenyl)-benzo[h]-5,6-dihydroquinazoline-2-amine

From 3,4,5-trimethoxyphenylguanidinium nitrate (2.14 g, 7.4 mmol), 3,4-dihydro-2-(dimethylaminomethylene)-5-methoxy-1(2H)-naphthalenone (2.60 g, 11.3 mmol) and sodium hydroxide (332 mg, 8.3 mmol) to give the title compound as an olive green solid (1.63 g) m.p. 226.5–227.5°. δH (d⁶ DMSO) 9.36 (1H, s), 8.37 (1H, s), 7.88 (1H, d, J 7.2 Hz), 7.36 (1H, t, J8.0 Hz), 7.31 (2H, s), 7.12 (1H, d, J 7.6 Hz), 3.83 (3H, s), 3.79 (6H, s), 3.62 (3H, s), 2.85 (2H, m) and 2.74 (2H, m). MS (ES⁺) 394 (MH⁺, 100%).

The 3,4-dihydro-2-(dimethylaminomethylene)-5-methoxy-1(2H)-naphthalenone starting material was prepared from 5-methoxy-1-tetralone (5.0 g, 28.4 mmol) and N,N-dimethylformamide diethyl acetal (25 g, 170.2 mmol) to give the desired product as brown needles (5.27 g). m.p. 108–110°. MS (ES⁺) 232 (MH⁺,100%).

EXAMPLE 3

8-Methoxy-N-(3,4,5-trimethoxyphenyl)-benzo[h]-5,6-dihydroquinazoline-2-amine

From 3,4,5-trimethoxyphenylguanidinium nitrate (2.14 g, 7.4 mmol), 3,4-dihydro-2-(dimethylaminomethylene)-6-methoxy-1(2H)-naphthalenone (2.60 g, 11.3 mmol) and sodium hydroxide (332 mg, 8.3 mmol) to give the title compound as a green solid (1.70 g) m.p. 192.5–193.5°. δH (d⁶ DMSO) 9.29 (1H, brs), 8.30 (1H, s), 8.17 (1H, d, J 8.6 Hz), 7.30 (2H, s), 6.96 (1H, dd, J 8.6, 2.6 Hz), 6.91 (1H, d, J 2.5 Hz), 3.82 (3H, s), 3.79 (6H, s), 3.62 (3H, s), 2.88 (2H, m) and 2.76 (2H, m). MS (ES⁺) 394 (MH⁺, 100%).

The 3,4-dihydro-2-(dimethylaminomethylene)-6-methoxy-1(2H)-naphthalenone starting material was prepared from 6-methoxy-1-tetralone (5.29 g, 30 mmol) and N,N-dimethylformamide dimethyl acetal (24 ml, 180 mmol) to give the desired product as a brown oil (2.67 g). δH (CDCl₃) 8.00 (1H, d, J 8.6 Hz), 7.67 (1H, s), 6.81 (1H, dd, J 8.6, 2.6 Hz), 6.65 (1H, d, J 2.6 Hz), 3.83 (3H, s), 3.11 (6H, s), 2.95–2.90 (2H, m) and 2.88–2.79 (2H, m).

EXAMPLE 4

9-Methoxy-N-(3,4,5-trimethoxyphenyl)-benzo[h]-5,6-dihydroquinazoline-2-amine

From 3,4,5-trimethoxyphenylguanidinium nitrate (1.13 g, 3.9 mmol), 3,4-dihydro-2-(dimethylaminomethylene)-7- methoxy-1(2H)-naphthalenone (1.0 g, 4.3 mmol) and sodium hydroxide (173 mg, 4.3 mmol) to give the title compound as a mustard brown solid (181 mg) m.p. 170.9°. δH (CDCl$_3$) 8.27 (1H, s), 7.86 (1H, d, J 2.7 Hz), 7.16 (2H, m), 7.04 (2H, s), 6.95 (1H, m), 3.90 (6H, s), 3.86 (3H, s), 3.83 (3H, s) and 2.84 (4H, m). MS (ES$^+$) 394 (MH$^+$,100%).

The 3,4-dihydro-2-(dimethylaminomethylene)-7-methoxy-1(2H)-naphthalenone starting material was prepared from 7-methoxy-1-tetralone (5.0 g, 28.4 mmol) and N,N-dimethylformamide diethyl acetal (10 ml, 58.3 mmol) ito give the desired product as a yellow solid (1.28 g). m.p. 95.1 °. MS (ES$^+$) 232 (MH$^+$, 100%).

EXAMPLE 5

6-Methyl-N-(3,4,5-trimethoxyphenyl)benzo[h]-5,6-dihydroquinazoline-2-amine

From 3,4,5-trimethoxyphenylguanidinium nitrate (1.43 g, 5.0 mmol), 3,4-dihydro-2-(dimethylaminomethylene)-4-methyl-1(2H)-naphthalenone (1.61 g, 7.5 mmol) and sodium hydroxide (220 mg, 5.5 mmol). The crude product was treated with decolourising charcoal in hot ethyl acetate, the solution filtered and allowed to cool to give the title compound as bright yellow crystals (205 mg), m.p. 163–164°. δH (d$^6$ DMSO) 9.38 (1H, s), 8.38 (1H, s), 8.26 (1H, d, J 7.7 Hz), 7.48–7.37 (3H, m), 7.32 (2H, s), 3.80 (6H, s) 3.62 (3H, s), 3.11 (1H, m), 2.94 (1H, dd, J 15.4, 6.3 Hz), 2.62 (1H, dd, J 15.5, 6.2 Hz) and 1.18 (3H, d, J 6.9 Hz). MS (ES$^+$) 378 (MH$^+$, 100%).

The 3,4-dihydro-2-(dimethylaminomethylene)-4-methyl-1(2H)-naphthalenone starting material was prepared from 4-methyl-1-tetralone (4.0 g, 25 mmol) and N,N-dimethylformamide diethyl acetal (17 ml, 100 mmol) to give the desired product as a thick yellow oil (4.53 g). δH (CDCl$_3$) 8.03 (1H, dd, J 7.7, 1.5 Hz), 7.77 (1H, s), 7.39 (1H, td, J 7.4, 1.5 Hz), 7.29 (1H, td, J 7.5, 1.3 Hz), 7.20 (1H, dm, J 7.5 Hz), 3.12 (6H, s), 3.10–2.90 (2H, m), 2.75 (1H, apparent q, 6.9 Hz) and 1.30 (3H, d, J 6.9 Hz). MS (ES$^+$) 216 (MH$^+$, 100%).

EXAMPLE 6

N-(3,4,5-Trimethoxyphenyl)-6,7-dihydro-5H-benzo[6,7]cyclohepta[d]pyrimidine-2-amine From 3,4,5-trimethoxyphenylguanidinium nitrate (1.14 g, 4.0 mmol), 2(dimethylaminomethylene)-2,3,4,5-tetrahydrobenzo[b]cyclohepten-1-one (1.29 g, 6.0 mmol) and sodium hydroxide (176 mg, 4.4 mmol) to give the title compound as a light pink solid (392 mg) m.p. 201–202°. δH (d$^6$ DMSO) 9.45 (1H, brs), 8.36 (1H, s), 7.77 (1H, m), 7.43 (1H, td, J 7.1, 3.1 Hz), 7.41 (1H, td, J 7.6, 3.4 Hz), 7.34 (1H, m), 7.33 (2H, s), 3.74 (6H, s), 3.60 (3H, s), 2.53 (2H, br t, J 7.0 Hz), 2.33 (2H, br t, J 7.3 Hz) and 2.15 (2H, br quintet, J 6.8 Hz). MS (ES$^+$) 378 (MH$^+$, 100%).

The 2-(dimethylaminomethylene)-2,3,4,5-tetrahydrobenzo[b]cyclo-hepten-1-one starting material was prepared from 1-benzosuberone (5.0 g, 31.3 mmol) and N,N-dimethylformamide diethyl acetal (25 ml, 197.7 mmol) to give the desired product after recrystallisation from diethyl ether as yellow crystals (3.95 g) m.p. 79–79.5°. MS (ES$^+$) 216 (MH$^+$, 100%).

EXAMPLE 7

N-(3,4,5-Trimethoxyphenyl)-5H-indeno[1,2d]pyrimidine-2-amine

From 3,4,5-trimethoxyphenylguanidinium nitrate (1.43 g, 5.0 mmol), 2-(dimethylaminomethylene)-indan-1-one (1.40 g, 7.5 mmol) and sodium hydroxide (220 mg, 5.5 mmol) to give the title compound as yellow crystals (105 mg), m.p. 214–215°, after recrystallisation from ethyl acetate. δH (CDCl$_3$) 8.54 (1H,s ), 8.03 (1H, d with fine splitting, J 6.8 Hz), 7.62 (1H, d with fine splitting, J 7.0 Hz), 7.53 (1H, td, J 7.3, 1.5 Hz), 7.47 (1H, td, J 7.0, 1.0 Hz), 7.24 (1H, br s), 7.10 (2H,s ), 3.92 (6H, s), 3.85 (3H, s) and 1.62 (2H, s). MS (ES$^+$) 350 (MH$^+$, 100%).

The 2-(dimethylaminomethylene)-indan-1-one starting material was prepared from 1-indanone (3.17 g, 24 mmol) and N,N-dimethylformamide diethyl acetal (21 ml, 120 mmol) to give the desired product as golden yellow crystals (2.61 g) m.p. 156–161°. MS (ES$^+$) 188 (MH$^+$, 100%).

EXAMPLE 8

N-(3,4,5-Trimethoxyphenyl)-benzo[h]-6-thia-5,6-dihydroquinazoline-2-amine

From 3,4,5-trimethoxyphenylguanidinium nitrate (1.43 g, 5.0 mmol), 3,4-dihydro-2-(dimethylaminomethylene)-4-thia-1(2h)-naphthalenone (1.31 g, 6.0 mmol) and sodium hydroxide (220 mg, 5.5 mmol). The crude product was treated with decolourising charcoal in hot ethyl acetate, the solution filtered and allowed to cool to give the title compound as bright yellow crystals (817 mg) m.p. 180–181° C. δH (d$^6$ DMSO) 9.54 (1H, br s), 8.46 (1H, s), 8.33 (1H, d with fine splitting, J 7.2 Hz), 7.43 (2H, m), 7.39–7.32 (1H, m), 7.29 (2H, s), 4.01 (2H, s), 3.79 (6H,s ) and 3.62 (3H, s). MS (ES$^+$) 382 (MH$^+$, 100%).

The 3,4-dihydro-2-(dimethylaminomethylene)-4-thia-1 (2H)-naphthalenone starting material was prepared from thiochroman-4-one (4.93 g, 26.8 mmol) and N,N-dimethylformamide diethyl acetal (23 ml, 133.8 mmol) to give the desired product as golden yellow crystals (5.15 g) m.p. 96–97°. MS (ES$^+$) 220 (MH$^+$, 100%).

EXAMPLE 9

9-Chloro-N-(3,4,5-trimethoxyphenyl)benzo[h]-thia-5,6-dihydroquinazoline-2-amine

From 3,4,5-trimethoxyphenylguanidinium nitrate (1.43 g, 5.0 mmol), 7-chloro-3,4-dihydro-2-(dimethylaminomethylene)-4-thia-1 (2H)-naphthalenone (1.39 g, 5.5 mmol) and sodium hydroxide (220 mg, 5.5 mmol). The crude product was treated with decolourising charcoal in hot ethyl acetate, the solution filtered and allowed to cool to give the title compound as yellow crystals (968 mg), m.p. 193–194°. δH (d$^6$ DMSO) 9.61 (1H, br s), 8.49 (1H, s), 8.29 (1H, m), 7.46 (2H, m), 7.27 (2H, s), 4.03 (2H, s), 3.82 (6H, s) and 3.63 (3H, s). MS (ES$^+$) 418 (MH$^{+37}$Cl, 43%), 416 (MH$^{+35}$Cl, 100%).

The 7-chloro-3,4-dihydro-2-(dimethylaminomethylene)-4-thia-1(2H)-naphthalenone starting material was prepared from 6-chloro-thiochroman-4-one (3.97 g, 20 mmol) and N,N-dimethylformamide diethyl acetal (20 ml, 80 mmol) to give the desired product as yellow crystals (4.38 g) m.p. 127–128°. MS (ES$^+$) 256 (MH$^+$, $^{37}$Cl, 33%), 254 (MH$^+$, $^{35}$Cl, 100%).

EXAMPLE 10

8,9-Dimethoxy-N-(3,4,5-trimethoxyphenyl)-benzo[h]-5,6-dihydroquinazoline-2-amine From 3,4,5-trimethoxyphenylguanidinium nitrate (1.14 g, 4.0 mmol), 3,4-dihydro-6,7-dimethoxy-2-(dimethylaminomethylene)-1(2H)-naphthalenone (1.04 g, 4.0 mmol) and sodium hydroxide (176 mg, 4.4 mmol). The crude product was purified by chromatography on silica (3% methanol in dichloromethane) and recrystallised from ethyl acetate-hexane to give the title compound as paleyellow crystals (354 mg) m.p. 179–182°. δH (CDCl$_3$) 8.22 (1H, s), 7.83 (1H, s), 7.12 (1H, brs), 6.99 (2H, s), 6.75 (1H, s), 3.96 (3H, s), 3.94 (3H, s), 3.88 (6H, s), 3.83 (3H, s) and 2.89–2.81 (4H, m). MS (ES$^+$) 424 (MH$^+$, 100%).

The 3,4-dihydro-6,7-dimethoxy-2-(dimethylaminomethylene)-1(2H)-naphthalenone starting material was prepared from 6,7-dimethoxy-1-tetralone (4.12 g, 20 mmol) and N,N-dimethyl formamide diethyl acetal (10.3 ml, 60 mmol) to give the product as red-brown crystals (3.26 g) m.p. 138–140°. MS (ES$^+$) 284 (MNa$^+$, 12%), 262 (MH$^+$, 100%), 189 (28%).

EXAMPLE 11

N-(3,4,5-Trimethoxyphenyl)-benzo[h]6oxa-5,6-dihydroquinazoline-2-amine

From 3,4,5-trimethoxyphenylguanidinium nitrate (1.44 g, 5.0 mmol), 3-(dimethylaminomethylene)-chroman-4-one (1.10 g, 5.5 mmol) and sodium hydroxide (220 mg, 5.5 mmol) to give the title compound as a dark green solid after recrystallisation from methanol (172 mg) m.p. 188.5–189.6°. δH (CDCl$_3$) 8.19 (1H, s), 8.15 (1H, s), 7.39 (1H, t, J 7.4 Hz), 7.20 (1H, s), 7.06 (4H, m), 5.16 (2H, s), 3.90 (6H, s) and 3.84 (3H, s). MS (ES$^+$) 366 MH$^+$, 100%).

The 3-(dimethylaminomethylene)-chroman-4-one starting material was prepared from 4-chromanone (5.0 g, 33.7 mmol) and N,N-dimethyl-formamide diethyl acetal (15 ml, 87.5 mmol) to give the desired product as orange crystals (4.3 g) m.p. 135.8°. MS (ES$^+$) 204 (100%).

EXAMPLE 12

N-(3,4,5-Trimethoxyphenyl)-thieno[2,3-h]-5,6-dihydroquinazoline-2-amine

From 3,4,5-trimethoxyphenylguanidinium nitrate (1.44 g, 5.0 mmol), 5-(dimethylaminomethylene)-4-oxo-4,5,6,7-tetrahydrobenzo[b]thiophene (1.13 g, 5.5 mmol) and sodium hydroxide (220 mg, 5.5 mmol) to give the title compound as a grey solid (443 mg) m.p. 229.1°. δH (d$^6$ DMSO) 9.29 (1H, s), 8.30 (1H, s), 7.52 (1H, d, J 5.2 Hz), 7.48 (1H, d, J 5.2 Hz), 7.26 (2H, s), 3.31 (9H, s), 2.92 (2H, m) and 2.90 (2H, m).

The 5-(dimethylaminomethylene)-4-oxo-4,5,6,7-tetrahydrobenzo[b]-thiophene starting material was prepared from 4-keto-4,5,6,7-tetrahydro-thianaphthene (5.0 g, 33 mmol) and N,N-dimethylformamide diethyl acetal (15 ml, 87.5 mmol) to give the desired product as large yellow crystals (2.3 g) after recrystallisation from ethyl acetate m.p. 106.9°. MS (ES$^+$) 208 (MH$^+$, 100%).

EXAMPLE 13

N-(3-Chlorophenyl)-9-methoxy-benzo[h]-5,6-dihydroquinazoline-2-amine

From 3-chrorophenylguanidinium nitrate (914 mg, 4.0 mmol), 3,4-dihydro-2-(dimethylaminomethylene)-7-methoxy-1(2H)-n aphthalenone (924 mg, 4.0 mmol; prepared as described in Example 4) and sodium hydroxide (176 mg, 4.4 mmol). The crude product was purified by chromatography on silica (25–30% ethyl acetate in hexane) and recrystallisation from ethyl acetate-hexane to afford the title compound as light yellow crystals (330 mg) m.p. 166.5–167.5. δH (CDCl$_3$) 8.29 (1H, s), 8.25 (1H, t, J 1.9 Hz), 7.89 (1H, d, J 2.8 Hz), 7.29 (1H, dt, J 8.4, 1.7 Hz), 7.23 (1H, d, J 8.1 Hz), 7.19 (1H, brs), 7.18 (1H, d, J 8.3 Hz), 7.01–6.97 (2H, m), 3.96 (3H, s) and 2.91–2.82 (4H, m). MS (ES$^+$) 340 (MH$^+$, $^{37}$Cl, 30%), 338 (MH$^+$, $^{35}$Cl, 100%).

The 3-chlorophenylguanidinium nitrate starting material was prepared by the method described for 3,4,5-trimethoxyphenylguanidinium nitrate in Example 1 from 3-chloroaniline (10.35 g, 81.2 mmol), cyanamide (10.2 ml of a 50% w/v solution in water) and concentrated nitric acid (6 ml, 85.3 mmol) to give the desired product as a pale brown solid (12.5 g) m.p. 172–174°. δH (d$^6$ DMSO) 9.75 (1H, br s), 7.52 (4H, br s), 7.45 (1H, t, J 7.8 Hz), 7.35–7.29 (2H, m) and 7.21 (1H, d, , 8.0 Hz).

EXAMPLE 14

N-(3-Benzyloxyphenyl)-9-methoxy-benzo[h]-5,6-dihydroquinazoline-2-amine

From 3-benzyloxyphenylguanidinium nitrate (6.5 g, 21.6 mmol), 3,4-dihydro-2-(dimethylaminomethylene)-7-methoxy-1(2H)-naphthalenone (5.0 g, 21.6 mmol; prepared as described in Example 4) and sodium hydroxide (952 mg, 23.8 mmol) to give the title compound as a grey solid (6.0 g) m.p. 163°. δH (d$^6$ DMSO) 9.54 (1H, s), 8.39 (1H, s), 7.86 (1H, s), 7.78 (1H, d, J 2.8 Hz), 7.30 (8H, m), 6.99 (1H, dd, J 8.3, 2.8 Hz), 6.60 (1H, dd, J 7.9; 2.4 Hz), 5.07 (2H, s), 3.69 (3H, s) and 2.79 (4H, m). MS (ES$^+$) 410 (MH$^+$, 100%).

3-Benzyloxyphenylguanidinium nitrate was prepared by the method described for 3,4,5-trimethoxyphenylguanidinium nitrate in Example 1 from 3-benzyloxyaniline (10.6 g, 53.0 mmol), cyanamide (3.35 g in 70 ml water, 79.8 mmol) and concentrated nitric acid (4 ml) to give the desired product as a light orange solid (9.5 g), m.p. 124.4°. MS (ES$^+$) 242 (MH$^+$, 100%).

EXAMPLE 15

N-[4-(2-Dimethylaminoethoxy)phenyl]-9-methoxy-benzo[h]-5,6-dihydroquinazoline-2-amine From 4-(2-dimethylaminoethoxy)phenylguanidinium dinitrate (350 mg, 1.0 mmol), 3,4-dihydro-2-(dimethylaminomethylene)-7-methoxy-1(2H)-naphthalenone (212 mg, 0.9 mmol; prepared as described in Example 4) and sodium hydroxide (80 mg, 2.0 mmol). The crude product was purified by chromatography on silica (ethyl acetate) to give the title compound as a dark yellow solid (120 mg) m.p. 131.5–132.5°. δH (CDCl$_3$) 8.23 (1H, s), 7.84 (1H, d, J 2.8 Hz), 7.58 (2H, m), 7.15 (1H, d, J 8.3 Hz), 6.94 (4H, m), 4.08 (2H, t, J 5.8 Hz), 3.90 (3H, s), 2.88 (2H, m), 2.79 (4H, m) and 2.36 (6H, s). MS (ES$^+$) 391 (MH$^+$, 100%).

4-(2-Dimethylaminoethoxy)phenylguanidinium dinitrate was prepared by the method described for 3,4,5-trimethoxyphenylguanidinium nitrate in Example 1 from 4-(2-dimethylaminoethoxy)aniline (5.0 g, 28 mmol), cyanamide (1.75 g, 41 mmol) in water (3.5 ml) and concentrated nitric acid (4 ml) to give the product as a light purple solid (6.8 g) m.p. 149–152°. MS (ES$^+$) 223 (MH$^+$, 100%).

EXAMPLE 16

6,6-Dimethyl-N-(3,4,5-trimethoxyphenyl)-benzo[h]-5,6-dihydroquinazoline-2-amine

From 3,4,5-trimethoxyphenylguanidinium nitrate (1.44 g, 5.0 mmol), 3,4-dihydro-4,4-dimethyl-2-(dimethylaminomethylene)-1-(2H)-naphthalenone (1.15 g, 5.0 mmol) and sodium hydroxide (220 mg, 5.5 mmol) to give the title compound as a bright yellow solid (1.15 g), m.p. 140–143°. δH (CDCl$_3$) 8.29 (1H, d, J 8.4 Hz), 8.24 (1H, s), 7.44 (2H, m), 7.34 (1H, ddd, J 7.8, 6.3 and 2.3 Hz), 7.10 (1H, br s), 7.08 (2H, s), 3.92 (6H, s), 3.84 (3H, s), 2.73 (2H, s) and 1.32 (9H, s).

The 3,4-dihydro-4,4-dimethyl-2-(dimethylaminomethylene)-1-(2H)-naphthalenone starting material was prepared from 4,4-dimethyl-1-tetralone (3.48 g, 20 mmol) and N,N-dimethylformamide diethyl acetal (10.5 ml, 60 mmol) to give the desired compund as bright yellkow crystals (3.53 g). δH (CDCl$_3$) 8.05 (1H, ddd, J 7.7, 1.5, 0.5 Hz), 7.78 (1H, s), 7.42 (1H, m), 7.33–7.25 (2H,m), 3.12 (6H, s), 2.80 (2H, s) and 1.33 (6H, s).

EXAMPLE 17

6,6-Dimethyl-N-(4-[2-dimethylaminoethoxy] phenyl)-benzo[h]-5,6-dihydroquinazoline-2-amine From 4-(2-dimethylaminoethoxy)phenylguanidium dinitrate (1.04 g, 3.0 mmol), 3,4-dihydro-4,4-dimethyl-2-(dimethylaminomethylene)-1-(2H)-naphthalenone (687 mg, 3.0 mmol; prepared as described in Example 16) and sodium hydroxide (240 mg, 6.0 mmol) to give the title compound as yellow crystals (550 mg), m.p. 114–115°. δH (CDCl$_3$) 8.32 (1H, d, J 8.6 Hz), 8.20 (1H, s), 7.58 (2H, dt, J 9.0, 2.2 Hz), 7.48–7.34 (3H, m), 6.97 (1H, br s), 6.94 (2H, dt, J 9.0, 2.2 Hz), 4.08 (2H, t, J 5.8 Hz), 2.74 (2H, t, J 5.8 Hz), 2.71 (2H, s), 2.35 (6H, s) and 1.31 (6H, s). MS(ES$^+$) 389 (MH$^+$, 100%).

EXAMPLE 18

6,6-Dimethyl-9-methoxy-N-(3,4,5-trimethoxyphenyl)-benzo[h]-5,6-dihydroquinazoline-2-amine From 3,4,5-trimethoxyphenylguanidinium nitrate (576 mg, 2.0 mmol), 3,4-dihydro-4,4-dimethyl-2-(dimethylaminomethylene)-7-methoxy-1 (2H)-naphthalenone (518 mg, 2.0 mmol) and sodium hydroxide (88 mg, 2.2 mmol) to give the title compound as a yellow solid (450 mg) m.p. 155–156°. δH (CDCl$_3$) 8.24 (1H, s,), 7.92 (1H, d, J 2.9 Hz), 7.35 (1H, d, J 8.6 Hz), 7.10 (1H, br s), 7.06 (2H, s), 7.00 (1H, dd, J 8.6, 2.9 Hz), 3.92 (6H, s), 3.86 (3H, s), 3.84 (3H, s), 2.70 (2H, s) and 1.29 (6H, s). MS (ES$^+$) 422 (MH$^+$, 100%).

The 3,4-dihydro-4,4-dimethyl-2-dimethylaminomethylene-7-methoxy- 1(2H)-naphthalenone used as starting material was prepared from 4,4-dimethyl-7-methoxytetralone [H. Hart et al J. Am. Chem. Soc. 85, 3269 (1963)] (37.57 g, 0.184 mmol) and N,N-dimethylformamide diethyl acetal (130 g) in a method analogous to that used in Example 1. This gave the desired product as a pale yellow solid (39.6 g). δH (CDCl$_3$) 7.77 (1H, s), 7.59 (1H, d, J 2.9 Hz), 7.23 (1H, d, J 8.6 Hz), 6.98 (1H, dd, J 8.6, 2.9 Hz), 3.84 (3H, s), 3.13 (6H, s), 2.77 (2H, s) and 1.30 (6H, s). MS (ES$^+$) 26–(MH$^+$, 100%).

EXAMPLE 19

6,6-Dimethyl-N-(4-[2-dimethylaminoethoxy] phenyl)-9-methoxy-benzo[h]-5,6-dihydroquinazoline-2-amine From 4-(2-dimethylaminoethoxy)phenylguanidinium dinitrate (693 mg, 2.0 mmol), 3,4-dihydro-4,4-dimethyl-2-(dimethylaminomethylene)-7-methoxy-1(2H)- naphthalenone (519 mg, 2.0 mmol; prepared as described in Example 18) and sodium hydroxide (160 mg, 4.09 mmol) to give the title compound as a yellow solid (565 mg) m.p. 75–78°. δH (CDCl$_3$) 8.20 (1H, s), 7.89 (1H, d, J 2.9 Hz), 7.59) (2H, dt, J 9.09, 2.2 Hz), 7.32 (1H, d, J 8.6 Hz), 7.01 (1H, dd, J 8.6, 2.9 Hz), 7.00 (1H, br s), 6.92 (2H, drm J 9.0, 2.2 Hz), 4.07 (2H, t, J 5.8 Hz), 3.89 (3H, s), 2.74 (2H, t, J 5.8 Hz), 2.69 (2H, s), 2.35 (6H, s) and 1.28 (6H, s). MS (ES$^+$) 419 (MH$^+$100%).

EXAMPLE 20

N-[4-(2-Dimethylaminoethoxy)phenyl]-9-methylbenzo[h]-5,6-dihydroquinazoline-2-amine From 4-(2-dimethylaminoethoxy)phenylguanidinium dinitrate (522 mg, 1.5 mmol), 3,4-dihydro-2-dimethylaminomethylene-7-methyl-1(2H) naphthalenone (322.5 mg, 1.5 mmol) and sodium hydroxide (120 mg, 3.0 mmol). The crude. product was purified by chromatography on silica (10% CH$_3$OH in CH$_2$Cl$_2$) to give the title compound as a yellow solid (110 mg) m.p. 139–140°. δH (CDCl$_3$) 8.22 (1H, s), 8.08 (1H, br s), 7.57 (2H, dt, J 9.0, 2.2 Hz) 7.19 (1H, dd, J 1.3, 7.7 Hz), 7.14–7.11 (2H, m), 6.93 (2H, dt, J 9.0, 2.2 Hz), 4.09 (2H, t, J 5.8 Hz), 2.92–2.87 (2H, m), 2.81–2.77 (2H, m), 2.76 (2H, t, J 5.8 Hz), 2.41 (3H, s) and 2.36 (6H, s). MS (ES$^+$) 375 (MH$^+$, 100%).

3,4-Dihydro-2-dimethylaminomethylene-7-methyl-1(2H) naphthalen one was prepared from 7-methyl-1-tetralone (4.8 g, 30 mmol) and N,N-dimethyl-formamide diethyl acetal (15.4 ml, 90 mmol). The crude product was recrystallised from diethyl ether-hexane to give yellow crystals (4.64 g) m.p. 79–82° MS (ES$^+$) 238 (MNa$^+$, 6%), 216 (MH$^+$, 100%).

EXAMPLE 21

10-Methoxy-N-(3,4,5-trimethoxyphenyl)benzo[h]-5, 6-dihydroquinazoline-2-amine

From 3,4-dihydro-2-dimethylaminomethylene-8-methoxy-1(2H)-naphthalenone (1 g, 4.32 mmol), 3,4,5-trimethoxyphenylguanidinium nitrate (1.25 g, 4.32 mmol) and sodium hydroxide (190 mg, 4.76 mmol) to give after recrystallisation from ethyl acetate the title compound as a yellow solid (268 mg) m.p. 164.1°. δH (CDCl$_3$) 8.26 (1H, s), 7.30 (2H, m), 7.03 (2H, s), 6.95 (1H, d, J 8.3 Hz),6.89 (1H, d, J 7.4 Hz), 3.91 (3H, s), 3.85 (6H, s), 3.81 (3H, s) and 2.75 (4H, m). MS (ES$^+$) 394 (MH$^+$, 100%).

3,4-Dihydro-2-dimethylaminomethylene-8-methoxy-1 (2H)naphthalenone was prepared from 8-methoxy-1-tetralone (2.0 g, 11.3 mmol) [Chatterjee, A et al, Tetrahedron (1980), 36, 2513], and N,N-dimethylformamide diethylacetal (6 ml, 34 mmol) to give the compound as orange crystals (1.9 g) m.p. 97.3°. MS (ES$^+$) 232 (MH$^+$, 40%), 205 (100%).

EXAMPLE 22

N-(5-Benzotriazolyl)-9-methoxybenzo[h]-5,6-dihydroquinazoline-2-amine

From 3,4-dihydro-2-dimethylaminomethylene-7-methoxy-1(2H)-naphthalenone (222 mg, 0.96 mmol), 5-guanidinobenzotriazole nitrate (230 mg, 0.96 mmol) and sodium hydroxide (422 mg, 1.06 mmol) to give the title compound as an orange solid (106 mg), m.p. 232–234°. δH (CDCl$_3$) 8.65 (1H, s), 8.31 (1H, s), 7.95–7.90 (1H, m), 7.87 (1H, s), 7.59 (1H, s), 7.35–7.31 (1H, m), 7.17 (1H, d, J 8.3 Hz), 6.98 (1H, d, J 8.3Hz), 3.88 (3H, s) and 2.90–2.83 (4H, m).

5-Guanidinobenzotriazole nitrate was prepared from 5-aminobenzotriazole (790 mg, 5.89 mmol), cyanamide (371 mg, in 0.75 ml $H_2O$, 8.83 mmol) and concentrated nitric acid (0.5 ml) following the method described for the guanidine of Example 1 to give the compound as a brown solid (248 mg). δH ($d^6$DMSO) 9.71 (1H, s), 8.0 (1H, d, J 6.5 Hz), 7.80 (1H, s), 7.41 (4H, s) and 7.26 (1H, d, J 6.7 Hz). MS ($ES^+$) 177 ($MH^+$, 100%).

EXAMPLE 23

N-(6-Benzothiazolyl)-9-methoxybenzo[h]-5,6-dihydroquinazoline-2-amine

From 3,4-dihydro-2-dimethylaminomethylene-7-methoxy-1(2H)-naphthalenone (50 mg, 2.16 mmol), 6-guanidinobenzothiazole nitrate (551 mg, 2.16 mmol) and sodium hydroxide (100 mg, 2.4 mmol) to give the title compound after recrystallisation from ethanol-toluene as an orange solid (240 mg) m.p. 81–83°. δH ($d^6$DMSO) 9.86 (1H, s), 9.17 (1H, s), 8.89 (1H, s), 8.43 (1H, s), 7.97 (1H, d, J 8.9 Hz), 7.89 (2H, m), 7.25 (1H, d, J 8.4 Hz), 7.02 (1H, d, J 8.3 Hz), 3.87 (3H, s) and 2.84–2.79 (4H, m).

6-Guanidinobenzothiazole nitrate was prepared from 6-aminobenzothiazole (1.50 g, 10.0 mmol), cyanamide (630 mg in 1.26 ml $H_2O$, 15.0 mmol) and concentrated nitric acid (1 ml) following the method described for the guanidine of Example 1 to give the compound as a peach solid (1.27 g) m.p. 202–204°. MS ($ES^+$) 192 ($MH^+$, 100%).

EXAMPLE 24

N-(4-Bromophenyl)-9-methoxybenzo[h]-5,6-dihydraquinazoline-2-amine

From 3,4-dihydro-2-dimethylaminomethylene-7-methoxy-1(2H)-naphthalenone (4.0 g, 17.4 mmol), 4-bromophenylguanidinium nitrate (4.82 g, 17.4 mmol) and sodium hydroxide (696 mg, 17.4 mmol) to give the title compound (4.74 g) as a colourless solid m.p. 144° δH ($CDCl_3$) 8.28 (1H, s), 7.82 (1H, d, J 2.8 Hz), 7.62 (2H, dd, J 2.1, 8.9 Hz), 7.44 (2H, dd, J 2.1, 8.9 Hz), 7.18 (1H, d, J 8.3 Hz), 7.17 (1H, s), 6.93 (1H, dd, J 2.8, 8.3 Hz), 3.91 (3H, s) and 2.91–2.80 (4H, m).

EXAMPLE 25

6,6-Diethyl-N-[4-(2-dimethylaminoethoxy)phenyl]-9-methoxybenzo[h]-5,6-dihydroquinazoline-2-amine From 4-(2-dimethylaminoethoxy)phenylguanidinium dinitrate (696 mg, 2.0 mmol), 4,4-diethyl-3,4-dihydro-2-dimethylaminomethylene-7-methoxy-1(2H) naphthalenone (570 mg, 2.0 mmol) and sodium hydroxide (176 mg, 4.4 mmol) to give the title compound after chromatography on silica (5–8% $CH_3OH$ in $CH_2Cl_2$) as a yellow solid (400 mg) m.p. 124–125°. δH ($CDCl_3$) 8.20 (1H, s), 7.93 (1H, d, J 8.6 Hz), 7.58 (2H, dt, J 9.09, 2.2 Hz), 6.99 (1H, dd, J, 2.9, 8.6 Hz), 6.98 (1H, br s), 6.92 (2H, dt, J 9.0, 2.2 Hz), 4.07 (2H, t, J 5.8 Hz), 3.90 (3H, s), 2.73 (2H, t, J 5.8 Hz), 2.71 (2H, s), 2.35 (6H, s), 1.63 (4H, q, J 7.4 Hz) and 0.78 (6H, t, J 7.4 Hz). MS ($ES^+$) 447 ($MH^+$, 100%).

4,4-Diethyl-3,4-dihydro-2-dimethylaminomethylene-7-methoxy-1(2H) naphthalenone was prepared from 4,4-diethyl-3,4-dihydro-7-methoxy-1(2H)naphthalenone (1.50 g, 6.5 mmol) and N,N-dimethylformamide diethyl acetal (3.3 ml, 19.5 mmol) to give the compound as a golden yellow oil (1.72 g) δH ($CDCl_3$) 7.76 (1H, s), 7.63 (1H, d, J 2.9 Hz), 7.11 (1H, d, J 8.6 Hz), 6.96 (1H, dd, J 2.9, 8.6 Hz), 3.84 (3H, s), 3.13 (6H, s), 2.78 (2H, s), 1.66 (4H, q, J 7.5 Hz) and 0.77 (6H, t, J 7.4 Hz). MS ($ES^+$) 288 ($MH^+$, 100%).

4,4-Diethyl-3,4-dihydro-7-methoxy-1(2H)naphthalenone was prepared as follows:

A solution of aluminium chloride (14.1 g, 105.6 mmol) in 1-nitropropane (25 ml) was added dropwise to a solution of anisole (4.19 g, 38.7 mmol) and γ, γ-diethylbutyrolactone [prepared as described by Lehmann, J et al, Synthesis, (1987), 1064–1067]; (5.0 g, 35.2 mmol) in 1-nitropropane (25 ml) at 0° and under $N_2$ and the reaction stirred in the cooling bath for 2.5 h. The reaction was poured onto crushed ice and 2M hydrochloric acid (150 ml) and the aqueous layer extracted with ethyl acetate (3×150 ml). The combined ethyl acetate layers were washed with brine, dried ($MgSO_4$) and concentrated in vacuo to a brown oil. Chromatography on silica (20–30% ethyl acetate in hexane) gave 4-ethyl-4-(4-methoxyphenyl)-1-hexanoic acid as a light brown oil (6.85 g) δH ($CDCl_3$) 7.19 (2H, dt, J 8.9, 2.2H z), 6.83 (2H, dt, J 8.9, 2.2 Hz), 3.78 (3H, s), 1.98 (4H, m), 1.65 (4H,m) and 0.68 (6H, t, J 7.4 Hz) which was used in the next step without further purification.

4-Ethyl-4-(4-methoxyphenyl)-1-hexanoic acid (6.50 g, 26.0 mmol) was added to hot polyphosphoric acid (18 g) and stirred at 90° for 20 mins before pouring onto crushed ice. The aqueous layer was extracted with diethyl ether (3×70 ml) and the ether extracts washed with 2M NaOH (2×70 ml), dried ($MgSO_4$) and concentrated in vacuo to a dark oil. Chromatography on silica (10–30% ethyl acetate in hexane) gave 4,4-diethyl-3,4-dihydro-7-methoxy-1(2H) naphthalenone as a light yellow oil (1.62 g). δH ($CDCl_3$) 7.53 (1H, d, J 2.9 Hz), 7.20 (1H, d, J 8.7 Hz), 7.08 (1H, dd, J 2.9, 8.7 Hz), 3.83 (3H, s), 2.70 (2H, apparent t, J 6.6 Hz), 2.00 (2H, apparent t, J 7.1 Hz), 1.72 (4H, m) and 0.81 (6H, t, J 7.5 Hz).

EXAMPLE 26

N-[4-(2-Dimethylaminoethoxy)phenyl]-9-methoxy-6-methyl-benzo[h]-5,6-dihydroquinazoline-2-amine From 3,4-dihydro-2-dimethylaminomethylene-7-methoxy-4-methyl-1(2H)-naphthalenone (857 mg, 3.5 mmol), 4-(2-dimethylaminoethoxy)phenyl guanidinium dinitrate (1.04 g, 3.0 mmol) and sodium hydroxide (240 mg, 6.0 mmol). The cude product was purified by chromatography on silica (10% $CH_3OH$ in $CH_2Cl_2$) and by recrystallisation from $CH_3OH$-isopropyl ether to give the title compound as yellow crystals (276 mg). δH ($CDCl_3$) 8.22 (1H, s), 7.86 (1H, d, J 2.8 Hz), 7.58 (2H, dt, J 9.0, 3.5, Hz), 7.35 (1H, br s), 7.18 (1H, d, J 8.4 Hz), 6.97 (1H, dd, J 2.8, 8.4 Hz), 6.91 (2H, dt, J 9.0, 3.5 Hz), 4.07 (2H, t, J 5.8 Hz), 3.87 (3H, s), 3.04 (1H, m), 2.93 (1H, dd, J 5.6, 15.2 Hz), 2.74 (2H, t, J 5.8 Hz), 2.57 (1H, dd, J 6.3, 15.1 Hz), 2.36 (6H, s) and 1.21 (3H, d, J 7.0 Hz). MS ($ES^+$) 405 ($MH^+$100%).

The 3,4-dihydro-2-dimethylaminomethylene-7-methoxy-4-methyl-1(2H)-naphthalenone starting material was prepared from 3,4-dihydro-7-methoxy-4-methyl-1-(2H) naphthalenone (950 mg, 5.0 mmol) [Gupta, A S; et al Tetrahedron (1967), 23, 2481], and N,N-dimethylformamide diethyl acetal (2.6 ml, 15.0 mmol). The product was purified by chromatography on silica (70% ethyl acetate in hexane—ethyl acetate) to give 3,4-dihydro-2-dimethylaminomethylene-7-methoxy-4-methyl-1(2H) naphthalenone as a yellow oil (920 mg). δH ($CDCl_3$) 7.77 (1H, s), 7.58 (1H, d, J 2.9 Hz), 7.12 (1H, d, J 8.4 Hz), 6.97 (1H, dd, J 2.9, 8.4 Hz), 3.85 (3H, s), 3.13 (6H, s), 3.01–2.90 (2H, m), 2.76–2.70 (1H, m) and 1.28 (3H, d, J 6.9 Hz). IR (liquid film) 1647 (s), 1547 (s) $cm^{-1}$.

EXAMPLE 27

N-[4-(2-Dimethylaminoethoxy)phenyl]-9-methoxy-6-thiabenzo[h]-5,6-dihydroquinazoline-2-amine The title compound was prepared from 4-(2-dimethylaminoethoxy)phenylguanidinium dinitrate (557 mg, 1.6 mmol), 3,4-dihydro-2-dimethylaminomethylene-7-methoxy-4-thia-1(2H)naphthalenone (400 mg, 1.6 mmol) and sodium hydroxide (129 mg, 3.2 mmol). The crude product was heated in ethyl acetate with decolourising charcoal, filtered hot and allowed to crystallise to give the title compound as yellow crystals (220 mg) $\delta H$ (CDCl$_3$) 8.26 (1H, s), 7.90 (1H, d, $J$ 2.9 Hz), 7.56 (2H, dt, $J$ 9.0, 2.2 Hz), 7.27 (1H, t, $J$ 8.5 Hz), 7.00 (1H, br s), 6,94 (1H, dd, $J$ 2.9, 8.5 Hz), 6.93 (2H, dt, $J$ 9.0, 2.2 Hz), 4.07 (2H, t, $J$ 5.8 Hz), 3.89 (3H, s), 3.83 (2H, s), 2.73 (2H, t, $J$ 5.8 HZ) and 2.34 (6H, s). MS (ES$^+$) 409 (MH$^+$, 100%).

The 3,4-dihydro-2-dimethylaminomethylene-7-methoxy-4-thia-1(2H)-naphthalenone starting material was prepared from 3,4-dihydro-7-methoxy-4-thia-1(2H)naphthalenone (1.0 g, 5.2 mmol [Degani, I. et al, Boll. Sci. Fac. Chim. Ind. Bologna (1966), 24(2–3) 75–91], and N,N-dimethyl-formamide diethyl acetal (2.7 ml, 15.6 mmol) to give the product as a mustard yellow solid (1.06 g). $\delta H$ (CDCl$_3$) 7.63 (1H, $J$ 2.9 Hz), 7.60 (1H, s), 7.17 (1H, d, $J$ 8. Hz), 6.90 (1H, dd, $J$ 2.9, 8.4 Hz), 3.98 (2H, s), 3.83 (3H, s) and 3.15 (6H, s). MS(EI$^+$) 249 (M$^+$, 66%), 205 (13%), 177 (59%), 82 (100%).

EXAMPLE 28

N-[4-(2-Dimethylaminoethoxy)phenyl]-5-thiabenzo [h]-5,6-dihydroquinazoline-2-amine From 3-dimethylaminomethylene-2-isothiochroman-4-one (350 mg, 1.71 mmol), 4-(2-dimethylaminoethoxy) phenylguanidinium dinitrate (569 mg, 1.71 mmol) and sodium hydroxide (150 mg, 3.76 mmol) to give the title compound as a yellow solid (180 mg) m.p. 148–150°. $\delta H$ (CDCl$_3$) 9.47 (1H, s), 8.44 (1H, s), 8.18 (1H, d, $J$ 6.8 Hz), 7.68 (2H, d, $J$ 8.8 Hz), 7.53 (2H, m), 7.38 (1H, d, $J$ 8.0 Hz), 6.90 (2H, d, $J$ 8.9 Hz), 4.02 (4H, m), 2.60 (2H, t, $J$ 5.8 Hz) and 2.22 (6H, s). MS (ES$^+$) 379 (MH$^+$, 100%).

3-Dimethylaminomethylene-2-isothiochroman-4-one was obtained from 2-isothiochroman-4-one (1.0 g, 6.1 mmol) and N,N-dimethylformamide diethyl acetal (4.0 ml, 13.6 mmol) to give the compound as orange crystals (735 mg). $\delta H$ (CDCl$_3$) 8.02 (1H, s), 7.86 (1H, d, $J$ 7.5 Hz), 7.42–7.31 (2H, m), 7.18 (1H, d, $J$ 7.2 Hz), 3.76 (2H, s) and 3.28 (6H, s).

EXAMPLE 29

5-Methyl-6-thia-N-(3,4,5-trimethoxyphenyl)benzo [h]-5,6-dihydroquinazoline-2-amine From 3,4-dihydro-2-dimethylaminomethylene-3-methyl-4-thia-1(2H)-naphthalenone (145 mg, 0.62 mmol), 3,4,5-trimethoxyphenylguanidinium nitrate (179 mg, 0.62 mmol) and sodium hydroxide (30 mg, 0.75 mmol) to give the title compound as a yellow solid (95 mg) m.p. 146–148°. $\delta H$ (CDCl$_3$) (1H, dd, $J$ 2.0, 7.8 Hz), 8.27 (1H, s), 7.53 (1H, s), 7.38 (2H, m), 7.30–7.25 (1H, m), 7.04 (2H, s), 4.12 (1H, q, $J$ 6.9 Hz), 3.91 (6H, s), 3.84 (3H, s) and 1.56 (3H, d, $J$ 7.0 Hz).

3,4-Dihydro-2-dimethylaminomethylene-3-methyl-4-thia-1(2H)-naphthalenone was prepared from 3,4-dihydro-3-methyl-4-thia-1(2H)naphthalenone (1.55 mg, 0.87 mmol), [Clayton, S E et al. Tetrahedron (1993) 49, 939], and N,N-dimethyl formamide diethylacetal (2 ml) to give the compound as yellow crystals (161 mg). $\delta H$ (CDCl$_3$) 8.12 (1H, dd, $J$ 1.5, 7.8 Hz), 7.50 (1H, s), 7.34–7.16 (3H, m), 4.36 (1H, q, $J$ 7.1 Hz), 3.16 (6H, s) and 1.57 (1H, d, $J$ 7.0 Hz). MS (ES$^+$) 234 (MH$^+$, 100%).

EXAMPLE 30

5,5-Dimethyl-6-thia-N-(3,4,5-trimethoxyphenyl) benzo[h]-5,6dihydroquinazoline-2-amine From 3,4-dihydro-2-dimethylaminomethylene-3,3-dimethyl-4-thia-1(2H)naphthalenone (103 mg, 0.44 mmol), 3,4,5-trimethoxyphenylguanidinium nitrate (126 mg, 0.44 mmol), and sodium hydroxide (20 mg, 0.48 mmol) to give the title compound after chromatography on silica (50% ethyl acetate in hexane) as yellow crystals (50 mg) m.p. 157–159° $\delta H$ (CDCl$_3$) 8.45 (1H, d, $J$ 7.7 Hz), 8.42 (1H, s), 7.37 (2H, m), 7.26 (1H, m), 7.14 (1H, s), 7.04 (2H, s), 3.90 (6H, s), 3.84 (3H, s) and 1.68 (6H, s). MS (ES$^+$) 410 (MH$^+$, 100%).

3,4-dihydro-2-dimethylaminomethylene-3,3-dimethyl-4-thia-1(2H)-naphthalenone was prepared from 3,4-dihydro-3,3-dimethyl-4-thia-1(2H)naphthalenone (426 mg, 1.72 mmol) [Clayton, S E et al, Tetrahedron (1993), 49, 939], and N,N-dimethylformamide diethyl-acetal (1 ml) to give the compound as a yellow solid (113 mg). $\delta H$ (CDCl$_3$) 8.22 (1H, dd, $J$ 1.6, 7.9 Hz), 7.32–7.14 (3H, m), 6.72 (1H, s), 2.89 (6H, s) and 1.63 (6H, s).

EXAMPLE 31

N-[4-(2-Dimethylaminoethoxy)phenyl]naphtho[2,1-h]-5,6-dihydro-6-thiaguinazoline-2-amine From 3-dimethylaminomethylenebenzo[f]thiochroman-4-one (400 mg, 1.26 mmol) and 4-(2-dimethylaminoethoxy) phenylguanidinium dinitrate (438 mg, 1.26 mmol) to afford the title compound (155 mg) as a canary yellow solid m.p. 165–167°. $\delta H$ (CDCl$_3$) 9.08 (1H, d, $J$ 8.3 Hz), 8.38 (1H, s), 7.77 (2H, m), 7.55–7.46 (5H, m), 7.05 (1H, br s), 6.88 (2H, m), 4.05 (2H, t, $J$ 5.8 Hz), 3.78 (2H, s), 2.73 (2H, t, $J$ 5.8 Hz) and 2.34 (6H, s). MS (ES$^+$) 429 (MH$^+$).

3-Dimethylaminomethylenebenzo[f]thiochroman-4-one was prepared from benzo[f]thiochroman-4-one (1.50 g, 7.01 mmol) and N,N-dimethyl-formamide diethylacetal to give the compound as a yellow solid (1.67 g) m.p. 163–1650. MS(EI) 269 (M$^+$, 49.8%), 82 (100%).

EXAMPLE 32

N-[4-(2-Dimethylaminoethoxy)phenyl]-9-ethylbenzo [h]-5,6-dihydroquinazoline-2-amine From 4-(2-dimethylaminoethoxy)phenylguanidinium dinitrate (5.3 g, 15.3 mmol), 3,4-dihydro-2-dimethylaminomethylene-7-ethyl-1(2H)-naphthalenone (3.5 g, 15.3 mmol) and sodium hydroxide (1.3 g, 33.6 mmol) to give the title compound as a yellow solid (2.0 g) m.p. 132–133°. $\delta H$ (CDCl$_3$) 8.21 (1H, s), 8.12 (1H,s), 7.58 (2H, d, $J$ 8.9 Hz), 7.20 (2H, m), 7.01 (1H, s), 6.93 (2H, d, $J$ 8.9 Hz), 4.07 (2H, t, $J$ 5.8 Hz), 2.89 (2H, m), 2.78 (2H, m), 2.73 (4H, m), 2.34 (6H, s) and 1.30 (3H, t, $J$ 7.6 Hz).

3,4-Dihydro-2-dimethylaminomethylene-7-ethyl-1(2H) naphthalenone was prepared from 7-ethyl-1-tetralone (5 g, 30.0 mmol) and N,N-dimethylformamide diethylacetal (15 ml) to give the compound as a yellow solid (4.6 g) m.p. 132–139°. $\delta H$ (CDCl$_3$) 7.87 (1H, d, $J$ 1.7 Hz), 7.71 (1H, s), 7.21 (1H, dd, J 2.0, 7.7 Hz), 7.08 (1H, d, J 7.7 Hz), 3.11 (6H, s), 2.85 (4H, m), 2.66 (2H, q, J 7.6 Hz) and 1.24 (3H, m).

EXAMPLE 33

9-Dimethylamino-N-[4-(2-dimethylaminoethoxy) phenyl]benzo[h]-5,6-dihydroquinazoline-2-amine From 3,4-dihydro-7-dimethylamino-2-(dimethylaminomethylene)-1(2H)-naphthalenone (360 mg, 1.38 mmol), 4-(2-dimethylaminoethoxy)phenyl guanidinium dinitrate (530 mg, 1.52 mmol) and sodium hydroxide (121 mg, 3.05 mmol) to give the title compound (223 mg) as a yellow solid m.p. 136°. δH (CDCl$_3$) 8.20 (1H, s), 7.73 (1H, d, J 2.8 Hz), 7.62 (2H, m), 7.11 (1H, d, J 8.3 Hz), 6.99 (1H, s), 6.91 (2H, m), 6.81 (1H, dd, J 2.8, 8.4 Hz), 4.06 (2H, t, J 5.8 Hz), 3.01 (6H, s), 2.77 (4H, m), 2.75 (2H, t, J 7.5 Hz) and 2.34 (6H, s).

The naphthalenone used as starting material was prepared in an analogous manner to the starting material of Example 1, from 7-dimethylaminotetralone (0.5 g, 2.64 mmol) and N,N-dimethylformamide diethylacetal (2.3 ml) to give the desired product as a yellow solid m.p. 114°. MS (ES$^+$) 245 (MH$^+$, 20%), 216 (100%).

7-Dimethylaminotetralone was prepared by treating 7-tert-butoxycarbonyl amino-1-tetralone (2.0 g, 7.6 mmol) with sodium hydride (337 mg of a 60% dispersion in oil) and iodomethane (0.48 ml, 7.6 mmol) in DMF (15 ml) at 100° for 3 h. The solvent was removed under reduced pressure to give an oil which was subjected to column chromatography (silica gel, 30% ethyl acetate/hexane) to give the desired product as a buff solid (137 mg) m.p. 107°. MS (ES$^+$) 190 (MH$^+$, 100%).

7-tert-Butoxycarbonylaminotetralone was prepared by heating a solution of 7-aminotetralone (1.0 g, 6.2 mmol) and di-tert-butyl dicarbonate (1.53 g, 7.0 mmol) in toluene at reflux for 1 h. The resulting solid was collected by filtration and dried to give the desired product (1.34 g) as a white solid m.p. 157.3°.

EXAMPLE 34

N-(5-Indolyl)-9-methoxybenzo[h]-5,6-dihydroquinazoline-2-amine

From 3,4-dihydro-2-dimethylaminomethylene-7-methoxy-1(2H)-naphthalenone (511, 2.21 mmol), 5-guanidinoindole nitrate (520 mg, 2.21 mmol) and sodium hydroxide (88 mg, 2.21 mmol) following the method used in Example 1 to give the title compound after recrystallisation from ethyl acetate as a yellow powder (167 mg) m.p. 255–257°. δH (d$^6$DMSO) 10.89 (1H, br s), 9.21 (1H, s), 8.32 (1H, s), 8.13 (1H, s), 7.80 (1H, s), 7.3 (1H, d, J 8.8 Hz), 7.31–7.22 (3H, m), 7.00 (1H, d, J 8.3 Hz), 6.33 (1H, s), 3.84 (3H, s) and 2.83–2.74 (4H, m).

5-Guanidinoindole nitrate was prepared as follows:

A freshly prepared solution of cyanamide (0.48 g, 11.43 mmol) in water (1 ml) was added to a solution of 5-aminoindole (1.00 g, 7.56 mmol) in ethanol (5 ml). The mixture was treated with concentrated nitric acid (69%, 0.51 ml, 7.90 mmol) and then refluxed for 18 h. A further quantity of cyanamide (0.24 g, 5.71 mmol) was added and then heating continued for 5 h. The reaction mixture was cooled to room temperature and evaporated in vacuo. The residue was triturated with ethyl acetate and the resulting precipitate collected and washed with ethyl acetate, then diethyl ether to give 5-guanidinoindole nitrate (1.67 g) as a brown solid m.p. 132–134°. δH (d$^6$DMSO) 6.46 (1H, s), 6.92 (1H, dd, J 1.8, 8.5 Hz), 7.07 (4H, s), 7.43 (3H, m), 9.35 (1H, s) and 11.25 (1H, br s).

EXAMPLE 35

9-Benzyloxy-N-(3,4,5-trimethoxyphenyl)benzo[h]-5,6-dihydroquinazoline-2-amine

From 7-benzyloxy-3,4-dihydro-2-dimethylaminomethylene-1(2H)-naphthalenone (3.07 g, 10 mmol), 3,4,5-trimethoxyphenylguanidinium nitrate (2.88, 10 mmol) and sodium hydroxide (400 mg, 10 mmol) to give the title compound as a pale green solid (2.30 g) m.p. 189–190°. δH (CDCl$_3$) 8.28 (1H, s), 8.00 (1H, d, J 2.7 Hz), 7.45–7.34 (5H, m), 7.18 (1H, d, J 8.3 Hz), 7.11 (1H, s), 7.08 (2H, s), 7.01 (1H, dd, J 2.7, 8.3 Hz), 5.11 (2H, s), 3.91 (6H, s), 3.83 (3H, s) and 2.90–2.82 (4H, m).

7-Benzyloxy-3,4-dihydro-2-dimethylaminomethylene-1 (2H)naphthalenone was prepared from 7-benzyloxy-3,4-dihydro-1(2H)naphthalenone (6.0 g, 23.8 mmol) and N,N-dimethylformamide diethylacetal (20 ml, 119.4 mmol) to give the desired compound as a pale yellow solid (4.56 g) m.p. 85–86°. MS(ES$^+$) 308 (MH$^+$, 100%).

7-Benzyloxy-3,4-dihydro-1(2H)naphthalenone was prepared by treating 7-hydroxy-1-tetralone (5.91 g, 36.4 mmol) and caesium carbonate (13 g, 40.0 mmol) in dry DMF (100 ml) and under N$_2$ with benzylbromide (6.22 g, 4.33 ml, 36.4 mmol). The reaction was stirred for 3 h and the mixture then filtered and the filtrate concentrated in vacuo. The oily residue was partitioned between ethyl acetate (200 ml) and brine (200 ml), the organic layer separated, dried (MgSO$_4$) and concentrated in vacuo. Trituration of the resultant solid with diethylether-hexane (1:1, 200 ml) gave the desired compound as a white solid (6.57 g) m.p. 86–87°0. MS (EI, 60V) 252 (M$^+$, 100%).

EXAMPLE 36

9-Bromo-N-(3,4,5-trimethoxyphenyl)benzo[h]-5,6-dihydroquinazoline-2-amine

From 3,4,5-trimethoxyphenylguanidinium nitrate (4.32 g, 15.0 mmol), 7-bromo-3,4-dihydro-2-dimethylaminomethylene-1(2H)naphthalenone (4.20 g, 15.0 mmol) and sodium hydroxide to give the title compound as a light green solid (3.96 g). δH (CDCl$_3$) 8.49 (1H, d, J 2.2 Hz), 8.28 (1H, s), 7.50 (1H, dd, J 2.2, 8.0 Hz), 7.15 (1H, d, J 8.1 Hz), 7.10 (1H, br s), 7.09 (2H, s), 3.96 (6H, s), 3.85 (3H, s) and 2.91–2.17 (4H, m). MS (ES$^+$) 444 (MH$^+$, $^{81}$Br, 100%), 442 (MH$^+$, $^{79}$Br, 100%).

The 7-bromo-3,4-dihydro-2-dimethylaminomethylene-1-(2H)naphthalenone starting material was prepared from 7-bromo-3,4-dihydro-1(2H)-naphthalenone (9.0 g, 40.0 mmol) [Griffin, R W et al, J.O.C. (1964), 29, 2109] and N,N-dimethylformamide diethyl acetal (20.6 ml, 120.0 mmol) to give the product as yellow crystals (8.01 g) after recrystallisation from tert.butylmethyl ether. δH (CDCl$_3$) 8.13 (1H, d, 2.2 Hz), 7.72 (1H, s), 7.45 (1H, dd, J 2.2, 8.0 Hz), 7.03 (1H, d, J 8.0 Hz), 3.13 (6H, s) and 2.92–2.74 (4H, m).

EXAMPLE 37

9-tert-Butoxycarbonylamino-N-[4-(2-dimethylaminoethoxy)phenyl]-benzo[h]-5,6dihydroquinazoline-2-amine From 7-tert-butoxycarbonylamino-3,4dihydro-2-(dimethylaminomethylene)-1(2H)-naphthalenone (5.0 g, 16.6 mmol), 4-(2-dimethylaminoethoxy)phenylguanidinium dinitrate (6.4 g, 18.2 mmol) and sodium hydroxide (1.46 g, 36.5 mmol) to give the title compound (5.0 g) as a yellow solid m.p. 190°. δH (CDCl$_3$) 8.2 (1H, s), 8.19 (1H, d, J 2.4 Hz), 7.57 (2H, m), 7.49 (1H, d, J 8.2 Hz), 7.17 (1H, d, J 8.2 Hz), 6.96 (3H, m), 6.59 (1H, s), 4.07 (2H, t, J 5.8 Hz), 2.83 (4H, m), 2.73 (2H, t, J 5.8 Hz), 2.34 (6H, s) and 1.54 (9H, s).

The naphthalenone used as starting material was prepared from 7-tert-butoxycarbonylamino-1-tetralone (5.0 g, 20.5 mmol) and N,N-dimethyl-formamide diethyl acetal (10 ml) to give the desired product as a yellow solid (5.2 g) m.p. 160°.

EXAMPLE 38

9-Amino-N-[4-(2-dimethylaminoethoxy)phenyl] benzo[h]-5,6-dihydroquinazoline-2-amine A suspension of the compound of Example 37 (4.5 g, 9.4 mmol) in ethanol (80 ml) was treated with 2N hydrochloric acid and heated at reflux for 4 h. On cooling a precipitate was collected, which was washed with ethanol and diethyl-ether to give the title compound (3.2 g) as a yellow solid m.p. 247°. δH (d$^6$DMSO) 10.72 (1H, br s), 9.75 (1H, br s), 8.41 (1H, s), 8.22 (1H, s), 7.75 (2H, d, J 9.0 Hz), 7.47 (2H, s), 7.05 (2H, d, J 9.1 Hz), 4.34 (2t, J 4.7 Hz), 3.49 (2H, m) and 2.85 (10H, m).

EXAMPLE 39

N-[4-(2-Dimethylaminoethoxy)phenyl]-9-methylsulphonamidobenzo[h]-5,6-dihydroquinazoline-2-amine To a solution of the compound of Example 38 i(500 mg, 1.3 mmol) n pyridine (4 ml) was added methane-sulphonyl chloride (0.1 ml, 1.3 mmol). The reaction mixture was stirred for 5 min. The resulting solid was collected by filtration to give the title compound (327 mg) as a pink solid m.p. 220°. δH (CDCl$_3$) 8.23 (1H, s), 8.06 (1H, d, J 2.4 Hz), 7.54 (2H, m), 7.32 (1H, dd, J 2.4, 8.1 Hz), 7.22 (1H, d, J 8.1 Hz), 7.15 (1H, s), 6.88 (2H, m), 4.04 (2H, t, J 5.7 Hz), 3.03 (3H, s), 2.83 (4H, m), 2.75 (2H, t, J 6.6 Hz) and 2.34 (6H, s).

EXAMPLE 40

N-[4-(2-Dimethylaminoethoxy)phenyl]-9-(N'-ethylureido)benzo[h]-5,6-dihydroquinazoline-2-amine To a solution of the compound of Example 38 (300 mg, 0.78 mmol) was added ethyl isocyanate (0.6 ml) and the reaction stirred at ambient temperature for 3 h. The resulting precipitate was collected and washed with diethyl ether to give the title compound (215 mg) as a yellow solid m.p. 228°. δH (d$^6$DMSO) 9.27 (1H, s), 8.54 (1H, s), 8.31 (2H, d, J 4.3 Hz), 7.76 (2H, d, J 8.8 Hz), 7.41 (1H, d, J 5.9 Hz), 7.16 (1H, d, J 8.3 Hz), 6.89 (2H, d, J 8.7 Hz), 6.12 (1H, m), 4.01 (2H, t, J 5.7 Hz), 3.13 (2H, m), 2.78 (4H, m), 2.63 (2H, t, J 5.7 Hz), 2.22 (6H, s) and 1.07 (3H, t, J 7.0 Hz).

EXAMPLE 41

9-Formyl-N-(3,4,5-trimethoxyphenyl)benzo[h]-5,6-dihydroquinazoline-2-amine

To a suspension of NaH (54 mg of a 60% dispersion in oil, 1.36 mmol) in dry THF (5 ml) under N$_2$ was added a solution of the compound of Example 36 (500 mg, 1.13 mmol) in THF (20 ml) and the mixture stirred for 30 min at room temperature. The reaction was cooled to −780. and tert-Butyl lithium (1.33 ml of 1.7M solution in pentanes, 2.26 mmol) added dropwise and the reaction stirred for 5 min before adding anhydrous dimethyl-formamide (0.5 ml, 6.50 mmol). The reaction was allowed to warm to room temperature, then stirred for 1.5 h and quenched with 2M hydrochloric acid (30 ml). The reaction mixture was extracted with ethyl acetate (3×30 ml) and the combined extracts washed with 2M hydrochloric acid (20 ml), saturated Na$_2$CO$_3$ (20 ml), dried (MgSO$_4$) and concentrated in vacuo. Chromatorgaphy on silica (50% ethyl acetate in hexane—neat ethyl acetate) and recrystallisation from ethyl acetate gave the title compound as yellow crystals (230 mg). δH (CDCl$_3$) 10.05 (1H, s), 8.83 (1H, d, J 1.7 Hz), 8.32 (1H, s), 7.89 (1H, dd, J 1.8, 7.7 Hz), 7.44 (1H, d, J 7.7 Hz), 7.13 (1H, br s), 7.08 (2H, s), 3.96 (6H, s), 3.85 (3H, s) and 3.07–2.86 (4H, m); MS (ES$^+$) 414 (MNa$^+$, 46%), 392 (MH$^+$, 100%).

EXAMPLE 42

9-Methylthio-N-(3,4,5-trimethoxyphenyl)benzo[h]-5,6-dihydroquinazoline-2-amine

The title compound was prepared from the compound of Example 36 (442 mg, 1.0 mmol), sodium hydride (48 mg of 60% dispersion in oil, 1.2 mmol) and tert-Butylithium (1.2 ml of 1.7M, 2.0 mmol) following the method used for Example 41. The resulting solution of 9-lithio-N-(3,4,5-trimethoxyphenyl)benzo[h]-5,6-dihydroquinazoline anion at −78° was quenched with dimethyldisulphide (282 mg, 3.0 mmol) and the reaction allowed to warm to room temperature and stirred for 1.5 h. The reaction mixture was partitioned between ethyl acetate (50 ml) and 2M hydrochloric acid (30 ml) and the aqueous layer re-extracted with ethyl acetate (2×30 ml). The combined ethyl acetate extracts were washed with saturated Na$_2$CO$_3$ (30 ml), dried (MgSO$_4$) and concentrated in vacuo. The crude material was purified by preparative hplc to give the title compound as a light yellow solid (42 mg). δH (CDCl$_3$) 8.29 (1H, d, J 2.0 Hz), 8.27 (1H, s), 7.30 (1H, dd, J 2.1, 7.9 Hz), 7.20 (1H, d, J 7.9 Hz), 7.08 (3H, s), 3.94 (6H, s), 3.84 (3H, s), 2.94–2.80 (4H, m) and 2.52 (3H, s). MS (ES$^+$) 410 (MH$^+$100%).

EXAMPLE 43

9-Hydroxymethyl-N-(3,4,5-trimethoxyphenyl)benzo[h]-5,6-dihydroquinazoline-2-amine To a solution of the compound of Example 41 (100 mg, 0.26 mmol) in methanol (5 ml) at room temperature was added sodium borohydride (19 mg, 0.51 mmol) and the reaction stirred for 30 min. The reaction mixture was partitioned between ethyl acetate (25 ml) and H$_2$O (20 ml). The organic layer was separated, dried (MgSO$_4$) and concentrated in vacuo to a light yellow solid. Recrystallisation from ethyl acetate gave the title compound as yellow crystals (68 mg). δH (CDCl$_3$) 8.33 (1H, s), 8.26 (1H,s), 7.40 (1H, dd, J 1.8, 7.7 Hz), 7.26 (1H, d, J 7.7 Hz), 7.09 (1H, br s), 7.05 (2H, s), 4.72 (2H, s), 3.92 (6H, s), 3.83 (3H, s) and 2.97–2.79 (4H, m). MS (ES$^+$) 394 (MH$^+$, 100%).

EXAMPLE 44

N-(3-Hydroxyphenyl)-9-methoxybenzo[h]-5,6-dihydroquinazoline-2-amine

A mixture of the compound of Example 14 (5.0 g, 12.2 mmol), ammonium formate (3.85 g, 61.1 mmol) and 10%Pd on carbon (50 mg) in ethanol (35 ml) and under $N_2$ was heated at reflux for 2.5 h. Ethanol was removed in vacuo and the residue dissolved in hot $CH_2Cl_2$ and filtered through Celite™. The Celite™ was washed thoroughly with ethyl acetate, ethanol and $CH_2Cl_2$ and the filtrate concentrated in vacuo to give the title compound as a light brown solid (1.2 g). m.p. 254.5°. δH (CDCl$_3$) 9.38 (1H, s), 9.21 (1H, s), 8.36 (1H, s), 7.78 (1H, d, J 2.8 Hz), 7.43 (1H, m), 7.23 (2H, m), 7.03 (2H, m), 6.35 (1H, d, J 7.5 Hz), 3.83 (3H, s) and 2.80 (4H, m).

EXAMPLE 45

9-Hydroxy-N-(3,4,5-trimethoxyphenyl)benzo[h]-5,6-dihydroquinazoline-2-amine 1,4-Cyclohexadiene (5 ml) was added to a de-gassed solution of the compound of Example 35 (2.19, 4.47 mmol) and 10% Pd on carbon (500 mg) in ethanol (100 ml) and the mixture heated to 60° under $N_2$ for 5 h. The reaction mixture was cooled and then filtered through Celite™ and the filter plug washed with ethanol. The ethanol filtrates were concentrated in vacuo and the resultant solid purified by chromatography on silica (CHCl$_3$) to give the title compound as a yellow solid (983 mg) m.p. 176–177°. δH (CDCl$_3$) 8.26 (1H, s), 7.82 (1H, d, J 2.7 Hz), 7.17–7.10 (2H, m), 7.02 (2H, s), 6.88 (1H, dd, J 2.7, 8.3 Hz), 3.90 (6H, s), 4.83 (3H, s) and 2.90–2.78 (4H, m).

EXAMPLE 46

9-Ethoxy-N-(3,4,5-trimethoxyphenyl)benzo[h]-5,6-dihydroquinazoline-2-amine

Caesium carbonate (195 mg, 0.6 mmol) was added to a solution of the compound of Example 45 (200 mg, 0.53 mmol) in dry DMF (7 ml) followed by ethyl iodide (86 mg, 45 μl, 0.55 mmol) and the reaction stirred at 55° for 3 h. The reaction was cooled to room temperature and treated with water (25 ml) to give the product as a precipitate which was washed with water and with diethyl ether (10 ml) to give the title compound as a yellow solid (125 mg). m.p. 161–162° δH (CDCl$_3$) 8.26 (1H, s), 7.87 (1H, d, J 2.7 Hz), 7:16–7.11 (2H, m), 7.06 (2H, s), 6.93 (1H, dd, J 2.7, 8.3 Hz), 4.08 (2H, q, J 7.0 Hz), 3.91 (6H, s), 3.84 (3H, s), 2.88–2.80 (4H, m) and 1.42 (3H, t, J 7.0 Hz).

EXAMPLE 47

6-Thia-N-(3,4,5-trimethoxyphenyl)-benzo[h]-5,6-dihydroquinazoline-2-amine-6-oxide m-Chloroperbenzoic acid (112 mg of 60% w/w, 0.39 mmol) was added to a solution of the compound of Example 8 (150 mg, 0.39 mmol) in $CH_2Cl_2$ (15 ml) and the reaction stirred at room temperature for 35 min. The reaction was diluted with $CH_2Cl_2$ (15 ml), washed with 2M NaOH (2×20 ml), dried (MgSO$_4$) and concentrated in vacuo. The crude product was purified by chromatography on silica (5% $CH_3OH$ in $CH_2Cl_2$) to give the title compound as a bright yellow solid (139 mg). δH (CDCl$_3$) 8.46 (1H, m), 8.41 (1H, s), 7.89 (1H,m), 7.69 (2H, m), 7.23 (1H, br s), 7.02 (2H, s), 4.39 (1H, d, J 14.5 Hz), 4.00 (1H, d, J 14.5 Hz), 3.90 (6H, s) and 3.85 (3H, s). MS (ES$^+$) 398 (MH$^+$, 100%).

EXAMPLE 48

N-(4-Carboxyphenyl)-6,6-dimethyl-9-methoxybenzo[h]-5,6-dihydroquinazoline-2-amine hydrochloride A mixture of 4-aminobenzoic acid (821 mg, 5.98 mmol) and 2-chloro-6,6-dimethyl-9-methoxybenzo[h]-5,6-dihydroquinazoline (1.50 g, 5.98 mmol) in 2-ethoxyethanol (8 ml) was heated at reflux for 3 h. The reaction mixture was allowed to cool to room temperature and the resultant precipitate collected by filtration and washed with ethanol (3×10 ml) and diethyl ether (2×10 ml) to give the title compound as a yellow powder (1.50 g) m.p. >300°. δH (d$^6$DMSO) 10.05 (1H, s), 8.43 (1H,s ), 7.96 (2H, d, J 9.0 Hz), 7.87 (2H, d, J 8.9 Hz), 7.80 (1H, d, J 2.9 Hz), 7.42 (1H, d, J 8.6 Hz), 7.09 (1H, dd, J 2.2, 8.6 Hz), 3.84 (3H, s), 2.72 (2H, s) and 1.22 (6H, s). MS (ES$^+$) 376 (MH$^+$, 100%).

2-Chloro-6,6-dimethyl-9-methoxybenzo[h]-5,6-dihydroquinazoline used as starting material was prepared as follows:

A suspension of guanidinium carbonate (10.05 g, 55.8 mmol) and sodium hydroxide (4.95 g, 124 mmol) in iso-propanol (350 ml) was stirred at 80° for 0.25 h and 3,4-dihydro-4,4-dimethyl-2-dimethylaminomethylene-7-methoxy-1(2H) naphthalenone (previously described in Example 18; 24.79 g, 95.7 mmol) added. The mixture was stirred under reflux for 20 h using a Soxhlet extractor filled with activated 4 Å mlolecular sieves to remove generated water. Solvent was removed in vacuo and the residue triturated with water. The crude product was filtered and washed well with water (3×) and diethyl ether (3×) to give 6,6-dimethyl-9-methoxybenzo[h]-5,6-dihydroquinazoline-2-amine as an off-white solid (18.0 g). Further product could be obtained by extraction of the aqueous filtrates with ethyl acetate (×2), drying the organic layers (Na$_2$SO$_4$) and concentration in vacuo to give a yellow solid. Recrystallisation of this solid from ethylacetate-isopropyl ether-hexane gave more of the benzo[h]-5,6-dihydroquinazoline-2-amine as an off white solid (4.17 g). δH (CDCl$_3$) 8.11 (1H, s), 7.71 (1H, d, J 2.8 Hz), 7.36 (1H, d, J 8.6 Hz), 7.02 (1H, dd, J 2.8, 8.6 Hz), 6.41 (2H, br s), 3.79 (3H, s), 2.59 (2H, s) and 1.20 (6H, s). MS (ES$^+$) 256 (MH$^+$, 100%), 226 (8%).

6,6-Dimethyl-9-methoxybenzo[h]-5,6-dihydroquinazoline-2-amine (18 g, 70.6 mmol) was treated with an ice-cold solution of concentrated sulphuric acid (180 ml) and water (260 ml) and the yellow suspension stirred for 15 min. The suspension was treated with sodium nitrite (13 g, 0.19 mmol) in water (200 ml) over 1 h and stirred at 200 for 4 h. The reaction was poured onto ice and neutralised with 25% aqueous ammonia to give a buff solid. This was filtered off, ground up under water, filtered and washed well with water (×2) and ether and dried under high vacuum to give 6,6-dimethyl-9-methoxybenzo[h]-5,6-dihydroquinazolin-2-one as a buff solid (16.2 g). δH (d$^6$DMSO) 7.84 (1H, s), 7.69 (1H, d, J 2.9 Hz), 7.40 (1H, d, J 8.6 Hz), 7.11 (1H, dd, J 2.9, 8.6 Hz), 3.81 (3H, s), 2.56 (2H, s), 1.21 (6H, s). MS (ES$^+$) 257 (MH$^+$, 100%), 227 (6%).

A solution of 6,6-dimethyl-9-methoxybenzo[h]-5,6-dihydro-quinazolin-2-one (16 g, 62.5 mmol) in N,N-dimethylformamide (10 ml) was treated with phosphorus oxychloride (210 ml) and heated under reflux for 6 h. The solvents were evaporated and then co-evaporated with $CH_2Cl_2$-toluene under reduced vacuum. The black residue was treated with ice-water and adjusted carefully to pH 7.5 with sodium hydrogen carbonate solution. The mixture was extracted with $CH_2Cl_2$ (×2) and then $CH_2Cl_2$-methanol (9:1,×2) and dried (MgSO$_4$). Removal of solvents in vacuo gave a black oil which was subjected to column chromatography (silica, ethyl acetate) to give the desired 2-chloro-6,6-dimethyl-9-methoxybenzo[h]-5,6-dihydro quinazoline as a yellow solid (13.8 g). δH (d$^6$DMSO) 8.62 (1H,s), 7.68 (1H, d, J 2.9 Hz), 7.45 (1H, d, J 8.7 Hz), 7.15 (1H, dd, J 8.6, 2.9 Hz), 3.83 (3H, s), 2.83 (2H, s) and 1.22 (6H,s ). MS (ES$^+$) 277 (MH$^+$, 36%), 275 (MH$^+$, 100%).

The following compounds of Examples 49–63 were prepared in a similar manner to the compound of Example 48 from the appropriate aniline or heteroaromatic amine and 2-chloro-6,6-dimethyl-9-methoxybenzo[h]-5,6-dihydroquinazoline.

EXAMPLE 49

N-(3-Carboxyphenyl)-6,6-dimethyl-9-methoxybenzo[h]-5,6-dihydroquinazoline-2-amine hydrochloride From 3-aminobenzoic acid (821 mg, 5.98 mmol) and 2-chloro-6,6-dimethyl-9-methoxybenzo[h]-5,6-dihydroquinazoline to give the title compound as a yellow powder (1.60 g) m.p. >300°. δH ($d^6$DMSO) 10.01 (1H, s), 8.60 (1H, t, J 1.8 Hz), 8.42 (1H,s ), 7.91 (1H, m), 7.82 (1H, d, J 2.8 Hz), 7.56 (1H, m), 7.42 (2H, m), 7.08 (1H, dd, J 2.9, 8.6 Hz), 3.82 (3H, s), 2.71 (2H, s) and 1.22 (6H, s). MS ($ES^+$) 376 ($MH^+$, 100%).

EXAMPLE 50

N-(3-Carboxamidophenyl)-6,6-dimethyl-9-methoxybenzo[h]-5,6-dihydroquinazoline-2-amine From 2-chloro-6,6-dimethyl-9-methoxybenzo[h]-5,6-dihydroquinazoline (0.5 g, 1.8 mmol) and 3-aminobenzamide (0.24 g, 1.8 mmol) to give the title compound (26 mg) as a white solid m.p. 251°. δH ($d^6$DMSO) 9.62 (1H, s), 8.96 (1H, s), 8.36 (1H, s), 7.81 (1H, d, J 1.9 Hz), 7.78 (1H, s), 7.43–7.28 (3H, m), 7.04 (1H, dd, J 1.1, 8.6 Hz), 3.87 (3H, s), 2.68 (2H, s) and 1.26 (6H, s).

EXAMPLE 51

N-[4-(Carboxymethyl)phenyl]-6,6-dimethyl-9-methoxybenzo[h]-5,6-dihydroquinazoline-2-amine From 2-chloro-6,6-dimethyl-9-methoxybenzo[h]-5,6-dihydroquinazoline (1.0 g, 3.64 mmol) and 4-aminophenylacetic acid (0.55 g, 3.64 mmol) to give the title compound (52 mg) as a yellow solid m.p. 118°. δH ($d^6$DMSO) 9.48 (1H, s), 8.35 (1H, s), 7.79 (1H, d, J 2.9 Hz), 7.76 (2H, d, J 8.5 Hz), 7.40 (1H, d, J 8.5 Hz), 7.17 (2H, d, J 8.5 Hz), 7.07 (1H, dd, J 2.9, 8.5 Hz), 3.83 (3H, s), 3.49 (2H, s), 2.69 (2H, s) and 1.23 (6H, s).

EXAMPLE 52

N-(3-Amidinophenyl)-6,6-dimethyl-9-methoxybenzo[h]-5,6-dihydroquinazoline-2-amine hydrochloride The title compound was prepared from 3-aminobenzamidine dihydrochloride (379 mg, 1.82 mmol) and 2-chloro-6,6-dimethyl-9-methoxybenzo[h]-5,6-dihydroquinazoline (500 mg, 1.82 mmol). The crude reaction mixture was partitioned between ethyl acetate and 2M NaOH and the organic layers washed with $H_2O$, dried ($MgSO_4$) and concentrated in vacuo to give a beige solid. The solid was dissolved in $CH_2Cl_2$ and $CH_3OH$ and treated with ethereal HCl (1.5 ml of 1.0M solution) and hexane to give the title compound as a pale yellow solid (50 mg) m.p. 206–208°. δH ($CDCl_3$) 8.29 (1H, s), 7.97 (2H, d, J 8.8 Hz), 7.91 (1H, d, J 2.9 Hz), 7.83 (2H, d, J 8.8 Hz), 7.40 (1H, s), 7.36 (1H, d, J 8.6 Hz), 7.03 (1H, dd, J 2.9, 8.6 Hz), 3.93 (3H, s), 2.74 (2H, s), 2.58 (3H, s) and 1.30 (6H, s). MS ($ES^+$) 374 ($MH^+$, 100%).

EXAMPLE 53

N-(4-Acetylphenyl)-6,6-dimethyl-9-methoxybenzo[h]-5,6-dihydroquinazoline-2-amine The title compound was prepared from 4-aminoacetophenone (740 mg, 5.46 mmol) and 2-chloro-6,6-dimethyl-9-methoxybenzo[h]-5,6-dihydroquinazoline (1.50 g, 5.46 mmol). The amide product was recrystallised from ethanol-$H_2O$ to give the title compound as yellow crystals (750 mg). δH ($CDCl_3$) 8.38 (1H, s), 8.25 (1H,s ), 8.02 (1H, d, J 8.0 Hz), 7.81 (1H, d, J 1.9 Hz), 7.70 (2H, m), 7.52 (1H, d, J 8.1 Hz), 7.21 (1H, dd, J 2.0, 8.0 Hz), 3.87 (3H, s), 2.89 (2H, s), 2.58 (3H, s) and 1.32 (6H, s). MS ($ES^+$) 374 ($MH^+$, 100%).

EXAMPLE 54

N-{4-[N'-(2-Diethylaminoethyl)carboxamido]phenyl}-6,6-dimethyl-9-methoxybenzo[h]-5,6-dihydroquinazoline-2-amine From 2-chloro-6,6-dimethyl-9-methoxybenzo[h]-5,6-dihydroquinazoline (500 mg, 1.82 mmol) and 4-amino-N-(2-diethylaminoethyl)benzamide hydrochloride (507 mg, 1.82 mmol) to give the title compound as a yellow solid (430 mg) m.p. 162–167°. δH (d6DMSO) 10.51 (1H, br s), 9.99 (1H, s), 8.84 (1H, br t), 8.43 (1H, s), 7.93 (3H, m), 7.80 (1H, d, J 2.8 Hz), 7.42 (1H, d, J 8.6 Hz), 7.10 (1H, dd, J 2.8, 8.6 Hz), 3.85 (3H, s), 3.64 (2H, d, J 5,6 Hz), 3.16 (6H, m), 2.72 (2H, s) and 1.23 (12H, m).

EXAMPLE 55

N-{4-[2-(Diethylaminoethoxy)carbonyl]phenyl}-6,6-dimethyl-9-methoxybenzo[h]-5,6-dihydroquinazoline-2-amine From 2-chloro-6,6-dimethyl-9-methoxybenzo[h]-5,6-dihydroquinazoline (500 mg, 1.82 mmol) and 2-(diethylamino)ethyl-4-aminobenzoate hydrochloride (496 mg, 1.82 mmol) to give the title compound after chromatography (silica, 10% $CH_3OH$ in $CH_2Cl_2$) as a light yellow solid (550 mg). δH ($CDCl_3$) 8.29 (1H, s), 8.03 (2H, d, J 6.9 Hz), 7.91 (1H, d, J 2.9 Hz), 7.82 (2H, d, J 8.8 Hz), 7.43 (1H, s), 7.35 (1H, d, J 8.6 Hz), 7.03 (1H, dd, J 2.9, 8.6 Hz), 4.39 (2H, t, J 6.2 Hz), 3.91 (3H, s), 2.87 (2H, t, J 6.2 Hz), 2.73 (2H, s), 2.66 (4H, q, J 7.2 Hz), 1.29 (6H, s) and 1.08 (6H, t, J 7.1 Hz). MS ($ES^+$) 476 ($MH^+$, 100%).

EXAMPLE 56

N-[4-Benzyloxycarbonyl-3-(2-diethylaminoethoxy)phenyl]-6,6-dimethyl-9-methoxybenzo[h]-5,6-dihydroquinazoline-2-amine dihydrochloride From benzyl-4-amino-2-(2-diethylaminoethoxy)benzoate (684 mg, 2.0 mmol), 2-chloro-6,6-dimethyl-9-methoxybenzo[h]-5,6-dihydroquinazoline (548 mg, 2.0 mmol) and ethereal HCl (2 ml of 1.0 M solution, 2.0 mmol) following the procedure described for Example 48 to give the title compound as a bright yellow solid (388 mg) m.p. 207–210°. δH ($d^6$DMSO) 10.12 (1H, br s), 10.05 (1H, s), 8.46 (1H, s), 7.92 (1H, s), 7.83 (1H, d, J 4.3 Hz), 7.81 (1H, d, J 1.5 Hz), 7.54 (1H, dd, J 1.1, 8.7 Hz), 7.48–7.33 (5H, m), 7.13 (1H, dd, J 2.9, 8.6 Hz), 5.28 (2H, s), 4.49 (2H,m), 3.84 (3H, s), 3.53 (2H,m), 3.39–3.16 (4H, m), 2.75 (2H, s), 1.24 (6H, s) and 1.22 (6H, t, J 7.2 Hz).

Benzyl 4-amino-2-(2-diethylaminoethoxy)benzoate was prepared as follows:

A solution of 2-fluoro-5-nitrobenzoic acid (1.0 g, 5.4 mmol) in dry DMF (10 ml) was added to a suspension of sodium hydride (4.15 mg of 60% dispersion in oil, 11.9 mmol) in DMF (20 ml) under $N_2$ and at room temperature. After 5 min. diethylaminoethanol (0.79 ml, 5.9 mmol) was added and the reaction mixture heated to 70° for 6 h. The reaction was cooled to room temperature, benzyl bromide (0.64 ml, 5.4 mmol) added and the reaction stirred for 18 h. The mixture was poured into brine (100 ml), extracted with ethyl acetate (3×75 ml) and the combined ethyl acetate extracts washed with brine (2×30 ml), dried (MgSO$_4$) and concentrated in vacuo. Chromatography on silica (3% methanol in CH$_2$Cl$_2$) gave benzyl 2-(2-diethylaminoethoxy)-4-nitrobenzoate as a yellow gum (962 mg). A solution of this compound in ethanol (25 ml) was treated with tin(II)chloride dihydrate (2.62 g, 11.6 mmol) and heated to reflux for 1.5 h. The reaction mixture was poured into H$_2$O (150 ml), treated with 2N NaOH (50 ml) and extracted with ethyl acetate (3×80 ml). The combined extracts were washed with Na$_2$CO$_3$ (80 ml), brine (80 ml), dried (MgSO$_4$) and concentrated in vacuo to give benzyl 4-amino-2-(2-diethylaminoethoxy)-benzoate as a yellow oil (692 mg). δH (CDCl$_3$) 7.76 (1H, d, $J$ 8.6 Hz), 7.46–7.29 (5H, m), 6.21 (1H, dd, $J$ 2.1, 8.2 Hz), 6.19 (1H, s), 5.28 (2H, s), 4.04 (2H, t, $J$ 6.8 Hz), 4.02 (2H, br s), 2.87 (2H, t, $J$ 6.8 Hz), 2.61 (4H, q, $J$ 7.2 Hz) and 1.04 (6H, t, $J$ 7.2 Hz). MS (ES$^+$) 343 (MH$^+$, 100%).

EXAMPLE 57

N-(4,5-Dimethoxy-3-hydroxyphenyl)-6,6-dimethyl-9-methoxybenzo[h]-5,6-dihydroquinazoline-2-amine hydrochloride The title compound was prepared from 5-amino-2,3-dimethoxyphenol (1.23 g, 7.3 mmol) and 2-chloro-6,6-dimethyl-9-methoxybenzo[h]-5,6-dihydroquinazoline (2.0 g, 7.3 mmol). The crude product was heated in ethanol with declolourising charcoal, filtered hot and allowed to crystalise to give the title compound as orange needles (1.11 g) m.p. 194–201° δH (CDCl$_3$) 10.68 (1H, br s), 8.05 (1H, br s), 7.95 (1H, br s), 7.40 (1H, d, $J$ 8.6 Hz), 7.38 (1H,s ), 7.18 (1H, dd, $J$ 2.9, 8.6 Hz), 6.63 (1H, d, $J$ 2.9 Hz), 5.88 (1H, s), 3.93 (3H, s), 3.90 (3H, s), 3.89 (3H, s), 2.77 (2H, s) and 1.32 (6H, s). MS (ES$^+$) 408 (MH$^+$, 100%).

EXAMPLE 58

6,6-Dimethyl-N-(3-hydroxy-4-methoxyphenyl)-9-methoxybenzo[h]-5,6-dihydroquinazoline-2-amine hydrochloride From 5-amino-2-methoxyphenol (862 mg, 6.19 mmol) and 2-chloro-6,6-dimethyl-9-methoxybenzo[h]-5,6-dihydroquinazoline (1.7 g, 6.19 mmol) to give the title compound as a yellow solid (1.0 g), m.p. 220.5°. δH (CDCl$_3$) 10.64 (1H, br s), 8.04.(1H, br s), 7.91 (1H, br s), 7.63 (1H, br s), 7.38 (1H, d, $J$ 8.7 Hz), 7.16 (1H, dd, $J$ 2.8, 8.6 Hz), 6.99 (1H, dd, $J$ 2.6, 8.7 Hz), 6.83 (1H, d, $J$ 8.7 Hz), 5.75 (1H, br s), 3.92 (3H, s), 3,90 (3H, s), 2.75 (2H, s) and 1.30 (6H,s). MS (ES$^+$) 378 (MH$^+$, 100%).

EXAMPLE 59

6,6-Dimethyl-N-(4-hydroxy-3-methoxyphenyl)-9-methoxybenzo[h]-5,6-dihydroquinazoline-2-amine hydrochloride From 4-amino-2-methoxyphenol (9.25 mg, 7.3 mmol) and 2-chloro-6,6-dimethyl-9-methoxybenzo[h]-5,6-dihydroquinazoline (2.0 g, 7.3 mmol) to give the title compound as a brown solid (2.1 g) m.p. 244.2°. δH (d$^6$DMSO) 9.98 (1H, br s), 8.32 (1H, s), 7.75 (1H, d, J 2.8 Hz), 7.45 (1H, d, $J$ 8.6 Hz), 7.38 (1H, s), 7.15 (1H, dd, $J$ 2.9, 8.6 Hz), 7.05 (1H, dd, $J$ 2.3, 8.5 Hz), 6.79 (1H, d, $J$ 8.5 Hz), 3.80 (3H, s), 3.78 (3H, s), 2.71 (2H, s) and 1.23 (6H, s). MS (ES$^+$) 378 (MH$^+$, 100%).

EXAMPLE 60

6,6-Dimethyl-N-[3-(2-hydroxyethyl)phenyl]-9-methoxybenzo[h]-5,6-dihydroquinazoline-2-amine hydrochloride From 3-aminophenethyl alcohol (986 mg, 7.2 mmol) and 2-chloro-6,6-dimethyl-9-methoxybenzo[h]-5,6-dihydroquinazoline (2.0 g, 7.2 mmol) to give the title compound as bright yellow crystals (1.97 g) m.p. 201.5°. δH (CDCl$_3$) 10.71 (1H, br s), 8.09 (1H, s), 7.90 (1H, s), 7.63 (1H, s), 7.59 (1H, d, $J$ 8.1 Hz), 7.40 (1H, d, $J$ 8.7 Hz), 7.32 (1H, t, $J$ 7.9 Hz), 7.16 (1H, dd, $J$ 2.8, 8.6 Hz), 7.09 (1H, d, $J$ 7.7 Hz), 3.92 (5H,m), 2.91 (2H, t, $J$ 6.5 Hz), 2.76 (2H, s) and 1.31 (6H, s). MS (ES$^+$) 376 (MH$^+$, 100%).

EXAMPLE 61

6,6-Dimethyl-N-(4-hydroxyphenyl)-9-methoxybenzo[h]-5,6-dihydroquinazoline-2-amine From 4-aminophenol (1.0 g, 9.12 mmol) and 2-chloro-6,6-dimethyl-9-methoxybenzo[h]-5,6-dihydroquinazoline-2-amine (2.0 g, 7.30 mmol) to give the title compound as a yellow solid (2.66 g). δH (d$^6$DMSO) 9.27 (2H, br s), 8.28 (1H, s), 7.77 (1H, d, $J$ 2.8 Hz), 7.56 (2H, d, $J$ 8.7 Hz), 7.40 (1H, d, $J$ 8.6 Hz), 7.07 (1H, dd, $J$ 2.8, 8.6 Hz), 6.73 (2H, d, $J$ 8.7 Hz), 3.83 (3H, s), 2.67 (2H, s) and 1.22 (6H, s). MS (ES$^+$) 348 (MH$^+$, 100%).

EXAMPLE 62

6,6-Dimethyl-N-(3-hydroxyphenyl)-9-methoxybenzo[h]-5,6-dihydroquinazoline-2-amine hydrochloride The title compound was prepared from 3-aminophenol (797 mg, 7.3 mmol) and 2-chloro-6,6-dimethyl-9-methoxybeno[h]-5,6-dihydroquinazoline (2.0 g, 7.3 mmol) to give the title compound as a yellow solid (1.65 g). m.p. 217–223°. δH (d$^6$DMSO) 9.73 (1H, br s), 8.38 (1H, s), 7.82 (1H, d, $J$ 2.9 Hz), 7.43 (1H, d, $J$ 8.6 Hz), 7.39 (1H, s with fine splitting), 7.18 (1H, d, $J$ 8.5 Hz), 7.13–7.06 (2H, m), 6.43 (1H, d, $J$ 7.8 Hz), 3.84 (3H, s), 2.72 (2H, s) and 1.24 (6H,s ). MS (ES$^+$) 348 (MH$^+$, 100%).

EXAMPLE 63

6,6-Dimethyl-N-(3-ethoxycarbonylphenyl)-9-methoxy benzo[h]-5,6-dihydroquinazoline-2-amine From 3-ethyl aminobenzoate (481 mg, 2.9 mmol) and 2-chloro-6,6-dimethyl-9-methoxybenxo[h]-5,6-dihydroquinazoline (800 mg, 2.9 mmol) to give the title compound after chromatography on silica (40% ethyl acetate in hexane) as a pale yellow solid (171 mg) m.p. 193–195°. δH (CDCl$_3$) 8.45 (1H, t, $J$ 2.9 Hz), 8.27 (1H, s), 7.95 (1H, d, $J$ 2.9 Hz), 7.93 (1H, m overlapping), 7.71 (1H, d, $J$ 8.2 Hz), 7.41 (1H, t, $J$ 8.2 Hz), 7.34 (1H, d, $J$ 8.3 Hz), 7.27 (1H,s ), 7.02 (1H, dd, $J$ 2.9, 8.6 Hz), 4.40 (2H, q, $J$ 7.0 Hz), 3.91 (3H, s), 2.72 (2H, s), 1.40 (3H, t, $J$ 7.0 Hz) and 1.29 (6H, s).

EXAMPLE 64

N-3-(N'-Amidinocarboxamido)phenyl-6,6dimethyl-9-methoxybenzo[h]-5,6-dihydroquinazoline-2-amine A solution of 6,6-dimethyl-N-(3-ethoxycarbonylphenyl)-9-methoxybenzo[h]-5,6-dihydroquinazoline-2-amine (150 mg, 0.37 mmol), guanidine hydrochloride (48 mg, 0.5 mmol) and sodium acetate (82 mg, 1.0 mmol) in ethyl alcohol was heated at reflux for 12 h. On cooling the reaction was concentrated under reduced pressure and the residue subjected to column chromatography (silica gel, 1:10:89 ammonium hydroxide/methanol/dichloromethane) to give the title compound (4.8 mg) as a yellow solid m.p. >150° (decomp). δH (CDCl$_3$) 9.52 (1H, s), 8.56 (1H, s), 8.36 (1H, s), 7.88 (1H, s), 7.78 (1H, d, J 7.8 Hz), 7.68 (1H, d, J 7.8 Hz), 7.39 (1H, d, J 8.6 Hz), 7.30–7.27 (1H,m), 7.07–7.04 (1H, m), 3.83 (3H, m), 2.69 (2H, s) and 1.23 (6H, s).

EXAMPLE 65

N-[4-Carboxy-3-(2-diethylaminoethoxy)phenyl]-6,6-dimethyl-9-methoxybenzo[h]-5,6-dihydroquinazoline-2-amine 10% Pd on carbon (100 mg) was added to a degassed solution of the compound of Example 56 (291 mg, 0.5 mmol) in ethanol (15 ml) and the mixture subjected to an atmosphere of hydrogen (balloon). After 8 h at room temperature the reaction was filtered through a plug of Celite™ and the filtrate concentrated invacuo to give a green solid. The solid was heated in methanol with decolourising charcoal, filtered and was recrystallised from CHCl$_3$ to give the title compound as a white solid (53 mg) m.p. 202–204°. δH (d$^6$DMSO) 10.00 (1H, s), 8.46 (1H, s), 7.91 (1H, s), 7.82 (1H, d, J 2.9 Hz), 7.76 (1H, d, J 8.7 Hz), 7.52 (1H, d, J 8.6 Hz), 7.45 (1H, d, J 8.6 Hz), 7.13 (1H, dd, J 2.9, 8.6 Hz), 4.48 (2H, br s), 3.85 (3H, s), 3.56 (2H, br s), 3.32 (4H, q, J 7.2 Hz), 2.74 (2H, s), 1.27 (6H, t, J 7.2 Hz) and 1.24 (6H, s).

EXAMPLE 66

N-[4-(2-N'-Benzyloxycarbonylaminoethyl)phenyl]-6,6-dimethyl-9-methoxybenzo[h]-5,6-dihydroquinazoline-2-amine From 2-chloro-6,6-dimethyl-9-methoxybenzo[h]-5,6-dihydroquinazoline (1.4 g, 5.18 mmol) and 4-(2-N-benzyloxycarbonylaminoethyl)aniline (1.4 g, 5.18 mmol) following the method used in Example 48 to give after column chromatography (silica, CH$_2$Cl$_2$) the title compound as an orange solid (1.45 g). δH (CDCl$_3$) 8.23 (1H, s), 7.91 (1H, d, J 2.9 Hz), 7.65 (1H, d, J 8.5 Hz), 7.34 (6H, m), 7.16 (3H, m), 7.01 (1H, dd, J 2.9,8.6 Hz), 5.1 (2H, s), 4.80 (1H, br s), 3.89 (3H, s), 3.48 (2H, m), 2.79 (2H, t, J 6.9 Hz), 2.70 (2H, s) and 1.28 (6H, s). MS (ES$^+$) 509 (MH$^+$, 100%).

EXAMPLE 67

N-[4-(2-Aminoethyl)phenyl]-6,6-dimethyl-9-methoxybenzo[h]-5,6-dihydroquinazoline-2-amine A suspension of the compound of Example 66 (1.40 g, 2.8 mmol) and 10% Pd on carbon (140 mg) in ethanol (25 ml) was stirred at room temperature under hydrogen (balloon) for 48 h. The reaction mixture was filtered through Celite™ and the filter plug washed with ethanol (3×25 ml). The ethanol filtrates were concentrated in vacuo to give the title compound as a light green solid (650 mg) m.p. 117.2°. δH (CDCl$_3$) 8.23 (1H, s), 7.91 (1H, d, J 2.9 Hz), 7.65 (2H, d, J 8.5 Hz), 7.33 (2H, m), 7.16 (2H, m), 7.01 (1H, dd, J 2.9, 8.6 Hz), 3.90 (3H, s), 2.96 (2H, t, J 6.4 Hz), 2.73 (2H, t, J 6.7 Hz), 2.70 (2H, s) and 1.28 (6H, s). MS (ES$^+$) 375 (MH$^+$, 100%).

EXAMPLE 68

6,6-Dimethyl-N-[4-(2-dimethylaminoethyl)phenyl]-9-methoxybenzo[h]-5,6-dihydroquinazoline-2-amine dihydrochloride Sodium triacetoxyborohydride (170 mg, 0.8 mmol) was added to a mixture of the compound of Example 67 (200 mg, 0.53 mmol) and formaldehyde (0.1 ml of 37% w/v solution in water) in 2,3-dichloroethane (3 ml) and the reaction stirred at room temperature for 5 h. The reaction was diluted with CH$_2$Cl$_2$ (25 ml) and washed with water (2×25 ml), brine (30 ml), the organic layer dried (MgSO$_4$) and then concentrated in vacuo to a yellow foam. This crude material was purified by column chromatography on silica (2% triethylamine-5% CH$_3$OH in CH$_2$Cl$_2$) to give a green oil which was dissolved in dry THF and treated with ethereal HCl to give the title compound as a yellow solid (63 mg) m.p.115.2° δH (d$^6$DMSO) 10.55 (1H, br s), 9.71 (1H, s), 8.37 (1H, s), 7.79 (3H, m), 7.42 (1H, d, J 8.6 Hz), 7.22 (2H, d, J 8.5 Hz), 7.10 (1H, dd, J 2.9, 8.5 Hz), 3.83 (3H, s), 3.23 (2H, m), 2.96 (2H, m), 2.79 (3H, s), 2.77 (3H, s), 2.70 (2H, s) and 1.22 (6H, s). MS (ES$^+$) 403 (MH$^+$, 100%).

EXAMPLE 69

9-Acetamido-6,6-dimethyl-N-[4-(2-dimethylaminoethoxy)phenyl]-benzo[h]-5,6-dihydroquinazoline-2-amine diacetate A solution of the compound of Example 70 (100 mg, 0.25 mmol) in toluene was treated with acetic anhydride (100 μl) and DMAP (2 mg), and heated at reflux for 0.5 h. The resulting yellow solid was collected and dried to give the title compound (106 mg) as a pale yellow solid m.p. 173°. δH (d$^6$DMSO) 10.02 (1H, s), 9.26 (1H, s), 8.58 (1H, s), 8.29 (1H, s), 7.77 (2H, d, J 8.7 Hz), 7.61 (1H, d, J 8.4 Hz), 7.43 (1H, d, J 8.4 Hz), 6.93 (2H, d, J 8.7 Hz), 4.01 (2H, t, J 5.8 Hz), 2.62 (2H, t, J 5.8 Hz), 2.24 (6H, s), 2.09 (3H, s), 1.93 (6H, s) and 1.27 (6H, s).

EXAMPLE 70

9-Amino-6,6-dimethyl-N-[4-(2-dimethylaminoethoxy)phenyl]benzo[h]-5,6-dihydroquinazoline-2-amine To a suspension of 10% Pd on carbon (60 mg) in ethanol was added the compound of Example 71 (270 mg, 0.62 mmol) and ammonium formate (300 mg) and the resulting mixture stirred at room temperature for 4 h. The catalyst was removed by filtration through a pad of Celite™. The solvent was evaporated under reduced pressure and the residue taken up in water and 2M NaOH added until a yellow solid precipitated, which was collected and dried to give the title compound (161 mg) m.p. >190° (decomp.) δH (CDCl$_3$) 8.18 (1H, s), 7.63 (1H, d, J 2.5 Hz), 7.54 (2H, d, J 8.9 Hz), 7.19 (1H, d, J 8.3 Hz), 7.03 (1H, s), 6.93 (2H, d, J 8.9 Hz), 6.77 (1H, dd, J 2.5, 8.3 Hz), 4.07 (2H, t, J 5.8 Hz), 3.72 (2H, br s), 2.73 (2H, t, J 5.8 Hz), 2.65 (2H, s), 2.34 (6H, s), and 1.25 (6H, s).

EXAMPLE 71

6,6-Dimethyl-N-[4-(2-dimethylaminoethoxy)phenyl]-9-nitrobenzo[h]-5,6-dihydroquinazoline-2-amine To a suspension of potassium carbonate (0.91 g, .6.6 mmol) in 2-ethoxyethanol (10 ml) was added 3,4-dihydro-2-dimethylaminomethylene-7-nitro-1(2H)-naphthalenone (0.9 g, 3.3 mmol) and 4-(2-dimethylaminoethoxy) phenylguanidinium dinitrate (1.15 g, 3.3 mmol) and the resulting mixture was then heated at 100° for 4 h. On cooling, the solvent was removed under reduced pressure. The residue was partitioned between CH$_2$Cl$_2$) and water, and the organic phase dried (MgSO$_4$) and evaporated. The residue was subjected to column chromatography (Silica gel, 10% methanol-CH$_2$Cl$_2$ to give the title compound (351 mg) as a yellow solid m.p. 181°. δH (CDCl$_3$) 9.15 (1H, d, J 2.4 Hz), 8.28–8.26 (2H, m), 7.58 (3H, d, J 8.8 Hz), 7.05 (1H, s), 6.97 (2H, d, J 8.8 Hz), 4.11 (2H, t, J 5.7 Hz), 2.80–2.78 (4H, m), 2.39 (6H, s) and 1.36 (6H, s).

The naphthalenone starting material used in the above process was prepared from 4,4-dimethyl-7-nitro-1-tetralone (Kleinm E. et al, International Patent Specification No. WO 97/09297. 1.0 g, 4.57 mmol) and N,N-dimethylformamide diethyl acetal (3.5 ml) using a method analogous to that used for the preparation of the naphthalenone starting material of Example 1 to give the desired product as a yellow solid m.p. 123–125°.

EXAMPLE 72

6,6-Dimethyl-N-[3-(2-dimethylaminoethoxy)-4-methoxyphenyl]-9-methoxybenzo[h]-5,6-dihydroquinazoline-2-amine A mixture of the compound of Example 58 (450 mg, 1.09 mmol), 2-dimethylaminoethyl chloride hydrochloride (235 mg, 1.63 mmol) and K$_2$CO$_3$ (601 mg, 4.35 mmol) in dry DMF (15 ml) under N$_2$ was heated to 850 for 18 h. Solvent was removed in vacuo and the residue partitioned between ethyl acetate (40 ml) and water (20 ml). The ethyl acetate layer was washed with water (2×25 ml), brine (25 ml) dried MgSO$_4$) and concentrated in vacuo. The crude product was purified by column chromatography (10% CH$_3$OH in CH$_2$Cl$_2$) to afford the title compound as a light brown solid (90 mg) m.p. 131.2°. δH (CDCl$_3$) 8.21 (1H, s), 7.89 (1H, d, J 2.9 Hz), 7.54 (1H, d, J 2.5 Hz), 7.34 (1H, d, J 8.76 Hz), 7.10 (1H, dd, J 2.5, 8.7 Hz), 6.99 (2H, m), 6.86 (1H, d, J 8.7 Hz), 4.22 (2H, t, J 5.9 Hz), 3.88 (3H, s), 3.85 (3H, s), 2.88 (2H, t, J 5.9 HZ), 2.69 (2H, s), 2.41 (6H, s) and 1.28 (6H, s). MS (ES$^+$) 475 (MH$^+$, 40%), 376 (30%), 258 (100%).

EXAMPLE 73

N-[3-(2-Diethylaminoethoxy)phenyl]-9-methoxy-6-thiabenzo[h]-5,6-dihydroquinazoline-2-amine From the compound of Example 74 (300 mg, 0.77 mmol), potassium carbonate (317 mg, 2.3 mmol) and 2-diethylaminoethylchloride hydrochloride (145 mg, 0.844 mmol) following the method described for Example 72 to give the title compound as a yellow powder (110 mg) m.p. 95–97°. δH (CDCl$_3$) 8.30 (1H,s), 7.96 (1H, d, J 2.9 Hz), 7.57 (1H,s), 7.30–7.20 (3H, m), 7.21 (1H, d, J 8.0 Hz), 6.96 (1H, dd, J 3.0, 8.6 Hz), 6.60 (1H, dd, J 2.5, 8.1 Hz), 4.19 (2H, t, J 5.9 Hz), 3.90 (3H, s), 3.85 (2H, s), 3.01 (2H, t, J 5.8 Hz), 2.77 (4H, q, J 7.1 Hz) and 1.15 (6H, t, J 7.1 Hz).

EXAMPLE 74

N-(3-hydroxyphenyl)-9-methoxy-6-thiabenzo[h]-5,6-dihydroquinazoline-2-amine

The title compound was prepared from 3,4-dihydro-2-dimethylaminomethylene-4-thia-1(2H)naphthalenone (600 mg, 2.41 mmol), 3-hydroxyphenylguanidinium nitrate (516 mg, 2.41 mmol) and sodium hydroxide (96 mg, 2.41 mmol) following the method described for the compound of Example 1.

EXAMPLE 75

N-[3-(2-Diethylaminoethoxy)-4,5-dimethoxyphenyl]-6,6-dimethyl-9-methoxybenzo[h]-5,6-dihydroquinazoline-2-amine dihydrochloride To the compound of Example 57 (460 mg, 1.04 mmol) and caesium carbonate (1.36 g, 4.16 mmol) in dry DMF (15 ml) was added 2-diethylaminoethylchloride hydrochloride (213 mg, 1.56 mmol) and the mixture heated to 110° under N$_2$ for 18 h. At this time more caesium carbonate (340 mg, 1.04 mmol) and 2-diethylaminoethylchloride hydrochloride (142 mg, 10.4 mmol) was added and the reaction heated for a further 5 h. DMF was removed in vacuo and the residue partitioned between CH$_2$Cl$_2$ (60 ml) and H$_2$O (60 ml). The organic layer was washed with H$_2$O (50 ml), dried (MgSO$_4$) and concentrated in vacuo to a dark oil. Chromatography on silica (10% CH$_3$OH in CH$_2$Cl$_2$) gave the product as an orange gum which was dissolved in anhydrous THF and treated with ethereal HCl (2 ml of 1.0M solution) to give the title compound as a bright orange powder m.p. 192–194° δH (d$^6$DMSO) 10.60 (1H, br s), 9.59 (1H, br s), 8.38 (1H, s), 7.81 (1H, d, J 2.7 Hz), 7.44 (1H, d, J 8.6 Hz), 7.36 (1H, s, with fine splitting), 7.28 (1H, s), 7.12 (1H, dd, J 2.5, 8.4 Hz), 4.39 (2H, m), 3.82 (6H, s), 3.68 (3H, s), 3.54 (2H, m), 3.27 (4H, m), 2.71 (2H, s), 1.29 (6H, t, J 7.1 Hz) and 1.24 (6H, s). MS (ES$^+$) 507 (MH$^+$, 100%).

EXAMPLE 76

N-[3-(3-Dimethylaminopropoxy)phenyl]-9-methoxybenzo[h]-5,6-dihydroquinazoline-2-amine From the compound of Example 62 (500 mg, 1.56 mmol) 3-dimethylaminopropylchloride hydrochloride (247 mg, 1.56 mmol) and caesium carbonate (1.1 g, 3.4 mmol) following the method described for the compound of Example 75 to give the title compound as a light brown solid (367 mg) m.p. 132.5°. δH (CDCl$_3$) 8.27 (1H, s), 7.89 (1H, d, J 2.7 Hz), 7.64 (1H, s), 7.18 (4H, m), 6.96 (1H, dd, J 2.8, 8.3 Hz), 6.57 (1H, d, J 8.1 Hz), 4.10 (2H, t, J 6.3 Hz), 3.91 (3H, s), 2.85 (4H, m), 2.61 (2H, t, J 7.2 Hz), 2.37 (6H, s) and 2.04 (2H, quintet, J 6.5 Hz).

EXAMPLE 77

N-[4-(2-Diethylaminoethoxy)-3-methoxyphenyl]-6,6-dimethyl-9-methoxybenzo[h]-5,6-dihydroquinazoline-2-amine dihydrochloride From the compound of Example 59 (600 mg, 1.45 mmol), 2-diethylaminoethylchloride hydrochloride (380 mg, 2.2 mmol) and sodium hydride (232 mg of 60% dispersion in oil, 5.8 mmol) following the method used in Example 75. The product was obtained as a yellow oil after column chromatography and was dissolved in ethyl acetate and treated with ethereal HCl (2 ml of 1.0M solution) to give the title compound as an orange solid (283 mg) m.p. 247.2°. δH (d$^6$DMSO) 10.59 (1H, br s), 9.75 (1H, br s), 8.36 (1H, s), 7.78 (1H, d, J 2.7 Hz), 7.61 (1H, s), 7.43 (1H, d, J 8.6 Hz), 7.30 (1H, d, J 8.6 Hz), 7.12 (1H, dd, J 2.8, 8.7 Hz), 7.03 (1H, d, J 8.6 Hz), 4.32 (2H, m), 3.81 (6H, s), 3.45 (3H, m), 3.24 (5H, m), 2.70 (2H, s) and 1.26 (10H, m). MS (ES$^+$) 477 (100%).

EXAMPLE 78

N-[4-(2-Diethylaminoethoxy)-3,5-dimethoxyphenyl]-6,6-dimethyl-9-methoxybenzo[h]-5,6-dihydroquinazoline-2-amine From 4-(2-diethylaminoethoxy)-3,5-dimethoxyaniline (200 mg, 0.75 mmol), 2-chloro-6,6-dimethyl-9-methoxybenzo[h]-5,6-dihydroquinazoline (205 mg, 0.75 mmol) and ethereal HCl (0.75 ml of 1.0M solution, 0.75 mmol) following the method described for Example 48. After column chromatography (silica, 1% aqueous NH$_3$ (aq).—10% CH₃OH in CH₂Cl₂) the title compound was obtained as an orange solid (120 mg) m.p. 92–94° δH (CDCl₃) 8.72 (1H, s), 7.91 (1H, d, $J$ 2.6 Hz), 7.35 (1H, d, $J$ 9.1 Hz), 7.06 (3H, s), 7.00 (1H, dd, $J$ 2.8, 9.0 Hz), 4.05 (2H, t, $J$ 4.5 Hz), 3.90 (6Hs), 3.88 (3H, s), 2.91 (2H, t, $J$ 5.0 Hz), 2.70 (2H, s), 2.62 (4H, q, $J$ 5.0 Hz), 1.30 (6H, s) and 1.05 (6H, t, $J$ 5.2 Hz). MS (ES⁺) 507 (MH⁺, 100%).

4-(2-Diethylaminoethoxy)-3,5-dimethoxyaniline was prepared as follows: Potassium 2,6-dimethoxy-4-nitrophenolate [Collins, R F and Davis, M. J. Chem. Soc. (1961), 1863] was treated with 2M hydrochloric acid and ethyl acetate and the organic layer separated and dried (MgSO₄) to give the free phenol. This compound (280 mg, 1.41 mmol) was treated with caesium carbonate (687 mg, 2.11 mmol) and diethylaminoethylchloride hydrochloride (363 mg, 2.11 mmol) following the procedure described in Example75 to give 4-(2-diethylaminoethoxy)-3,5-dimethoxynitrobenzene as a yellow solid which was used without further purification.

To a solution of the nitro compound (440 mg, 1.48 mmol) in ethanol (15 ml) was added ammonium formate (600 mg, 9.45 mmol) and 10% Pd on carbon (100 mg) and the reaction stirred at room temperature for 18 h. The mixture was filtered through Celite™, the filtrate concentrated in vacuo and partitioned between ethyl acetate and water. The ethyl acetate layers were dried (MgSO₄) and concentrated in vacuo to give 4-(2-diethylaminoethoxyl)-3,5-dimethoxy aniline as an orange powder (360 mg) δH (CDCl₃) 5.92 (2H, s), 4.02 (2H, t, $J$ 5.9 Hz), 3.77 (6H, s), 2.99 (2H, t, $J$ 5.9 Hz), 2.80 (6H, m) and 1.11 (4H, t, $J$ 6.9 Hz). MS (ES⁺) 269 (MH⁺, 100%).

EXAMPLE 79

N-[3,4-Dimethoxy-5-hydroxyphenyl]-9-methoxy-6-thiabenzo[h]-5,6-dihydroquinazoline-2-amine From 3,4-dihydro-2-dimethylaminomethylene-6-methoxy-4-thioa-1(2H)-naphthalenone (820 mg, 3.28 mmol) and 3,4-dimethoxy-5-hydroxyphenylguanidinium nitrate (900 mg, 3.28 mmol) following the method of Example 1 to afford the title compound (344 mg) as a pale yellow solid m.p. 199–201°. MS (ES⁺) 398 (MH⁺)

3,5-Dimethoxy-5-hydroxyphenylguanidinium nitrate was prepared from 3-amino-5,6-dimethoxyphenol (1.0 g, 5.92 mmol) and cyanamide following the method described in Example 1 to give the compound as a grey solid (925 mg) m.p. 180–183°. MS (ES⁺) 212 (MH⁺).

EXAMPLE 80

N-[3,4-Dimethoxy-5-(2-dimethylaminoethoxy) phenyl]-9-methoxy-6-thiabenzo[h]-5,6-dihydro-quinazoline-2-amine From the compound of Example 79 (303 mg, 0.76 mmol) and 2-dimethylaminoethyl chloride hydrochloride (142 mg, 1.0 mmol) following the method of Example 75 to afford the title compound (227 mg) as a yellow solid m.p. 113–115°. δH (CDCl₃) 8.28 (1H, s), 7.92 (1H, d, $J$ 2.9 Hz), 7.28 (1H, d, $J$ 8.5 Hz), 7.24 (1H, s), 7.05 (1H, d, $J$ 2.4 Hz), 6.98 (1H, d, $J$ 2.4 Hz), 6.93 (1H, dd, $J$ 2.9, 8.5 Hz), 4.18 (2H, t, $J$ 6.0 Hz), 3.88 (3H, s), 3.85 (3H, s), 3.83 (2H, s), 3.82 (3H, s), 2.82 (2H, t, $J$ 6.0 Hz) and 2.38 (6H, s). MS (ES⁺) 469 (MH⁺).

EXAMPLE 81

6,6-Dimethyl-N-[3-(2-hydroxyethoxy)phenyl]-9-methoxybenzo[h]-5,6-dihydroquinazoline-2-amine To the compound of Example 62 (1.32 g, 3.44 mmol) and K₂CO₃ (1.90 g, 13.76 mmol) in anhydrous DMF (25 ml) and under N₂ was added ethylene carbonate (450 mg, 5.16 mmol) and the mixture heated to 100° for 18 h. DMF was removed in vacuo and the residue partitioned between CH₂Cl₂ (100 ml) and H₂O (80 ml). The aqueous layer was re-extracted with CH₂Cl₂ (2×50 ml) and the combined CH₂Cl₂ extracts washed with H₂O (2×80 ml), brine (80 ml), dried (MgSO₄) and concentrated in vacuo. Chromatography on silica (40–60% ethyl acetate in hexane) gave the title compound as a light yellow solid (1.15 g) m.p. 130–131°. δH (CDCl₃) 8.25 (1H, s), 7.95 (1H, d, $J$ 2.9 Hz), 7.81 (1H, t, $J$ 2.3 Hz), 7.34 (1H, d, $J$ 8.5 Hz), 7.23 (1H, apparent t, $J$ 8.1 Hz), 7.19 (1H, br s), 7.06 (1H, ddd, $J$ 0.9, 2.1, 8.1 Hz), 7.01 (1H, dd, $J$ 2.9, 8.6 Hz), 6.59 (1H, ddd, $J$ 0.9, 2.5, 8.2 Hz), 4.18 (2H, apparent t, $J$ 4.3 Hz), 4.00 (2H, m), 3.91 (3H, s), 2.71 (2H, s), 2.21 (1H, br s, OH) and 1.29 (6H, s). MS(ES⁺) 392 (MH⁺, 100%).

EXAMPLE 82

6,6-Dimethyl-N-[3-(2-isopropylaminoethoxy) phenyl]-9-methoxybenzo[h]-5,6-dihydroquinazoline-2-amine To a solution of 6,6-dimethyl-9-methoxy-N-[3-(2-p-toluenesulphonyloxyethoxy)phenyl]benzo[h]-5,6-dihydroquinazoline-2-amine (366 mg, 0.67 mmol) in dry DMF (10 ml) and under N₂ was added isopropylamine (0.57 ml, 6.70 mmol) and the mixture heated to 60° for 6 h. DMF was removed in vacuo, the residue dissolved in CH₂Cl₂ (80 ml) and washed with aqueous saturated Na₂CO₃ (2×20 ml), H₂O (20 ml), brine (20 ml), dried (MgSO₄) and concentrated in vacuo. Chromatography on silica (8% CH₃OH in CH₂Cl₂) gave the title compound as a pale yellow solid (175 mg) after trituration with ether-hexane m.p. 122–124°. δH (CDCl₃) 8.24 (1H, s), 7.93 (1H, d, $J$ 2.9 Hz), 7.62 (1H, t, $J$ 2.1 Hz), 7.33 (1H, d, $J$ 8 Hz), 7.28–7.14 (3H, m), 7.00 (1H, dd, $J$ 2.9, 8.6 Hz), 6.58 (1H, d, $J$ 7.5 Hz), 4.19 (2H, t, $J$ 5.2 Hz), 3.90 (3H, s), 3.16 (1H, br s), 3.07 (2H, t, $J$ 5.3 Hz), 3.00 (1H, quintet, $J$ 6.3 Hz), 2.70 (2H, s), 1.28 (6H, s) and 1.16 (6H, d, $J$ 6.3 Hz). MS (ES⁺) 433 (MH⁺, 62%) 391 (12%), 348 (100%).

The tosylate starting material used above was prepared as follows. To a solution of the compound of Example 81 (930 mg, 2.38 mmol) in anhydrous pyridine (20 ml) was added tosyl chloride (1.81 g, 9.51 mmol) and the mixture stirred at room temperature under N₂ for 3 h. The reaction was poured onto H₂O (100 ml) and ethyl acetate (100 ml) and acidified to pH1 with 2M hydrochloric acid. The ethyl acetate layer was separated and the aqueous layer re-extracted with ethyl acetate (2×100 ml). The combined ethyl acetate extracts were washed with 2M HCl (100 ml), H₂O (100 ml), dried (MgSO₄) and concentrated in vacuo to give amine as a white solid (1.10 g). δH (CDCl₃) 8.25 (1H, s), 7.91 (1H, d, $J$ 9.1 Hz), 7.81 (2H, dt, $J$ 8.4, 1.8 Hz), 7.69 (1H, t, $J$ 2.2 Hz), 7.34 (1H, d, $J$ 8.6 Hz), 7.30 (2H, d, $J$ 8.0 Hz), 7.22 (1H, br s), 7.18 (1H, t, $J$ 8.2 Hz), 7.04 (1H, m), 7.01 (1H, dd, $J$ 2.9, 5.7 Hz), 6.44 (1H, dd, $J$ 1.7, 7.3 Hz), 4.40 (2H, m), 4.23 (2H, m), 3.88 (3H, s), 2.71 (2H, s), 2.40 (3H, s) and 1.29 (6H, s). MS (ES⁺) 546 (MH⁺, 100%).

EXAMPLE 83

N-[3-(2-Diethylaminoethoxy)phenyl]-6,6dimethyl-9-methoybenzo[h]-5,6-dihydroquinazoline-2-amine dihydrochloride The title compound was prepared from 6,6-dimethyl-9-methoxy-N-[3-(2-p-toluenesulphonyloxyethoxy)phenyl]

benzo[h]-5,6-dihydroquinazoline-2-amine (366 mg, 0.67 mmol; see Example 82) and diethylamine (1.4 ml, 13.2 mmol) following the method described for Example 82. The product was purified by chromatography on silica (8% CH$_3$OH in CH$_2$Cl$_2$) and then dissolved in anyhydrous THF (5 ml) and treated with ethereal HCl (2 ml of 1.0M solution.) This gave the title compound as a bright yellow solid (210 mg). δH (d$^6$DMSO) 10.48 (1H, br s), 9.67 (1H, s), 8.40 (1H, s), 7.82 (1H, d, J 2.9 Hz), 7.69 (1H, t, J 1.7 Hz), 7.43 (1H, d, J 8.6 Hz), 7.42 (1H, d, J 8.1 Hz), 7.25 (1H, t, J 8.2 Hz), 7.11 (1H, dd, J 2.9, 8.6 Hz), 6.61 (1H, dd, J 2.3, 8.2 Hz), 4.39 (2H, t, J 4.9 Hz), 3.85 (3H, s), 3.50 (2H, q, J 4.9 Hz), 3.23 (4H, m), 2.72 (2H, s), 1.26 (6H, t, J 7.2 Hz) and 1.24 (6H, s). MS (ES$^+$) 447 (100%).

EXAMPLE 84

6,6-Dimethyl-N-[4-(2-isopropylaminoethoxy)phenyl]-9-methoxybenzo[h]-5,6-dihydrouinazoline-2-amine The title compound was prepared from 6,6-dimethyl-9-methoxy-N-[4-(2-p-toluenesulphonyioxyethoxy)phenyl]benzo[h]-5,6-dihydroquinazoline-2-amine (440 mg, 0.81 mmol) and isopropylamine (0.7 ml, 8.10 mmol) following the procedure used in Example 82. After chromatography on silica (8% CH$_3$OH in CH$_2$Cl$_2$) the title compound was obtained as a yellow solid (294 mg), m.p. 86–87° δH (CDCl$_3$) 8.20 (1H, s), 7.89 (1H, d, J 2.6 Hz), 7.59 (2H, d, J 8.8 Hz), 7.32 (1H, d, J 8.6 Hz), 7.11 (1H, br s), 6.99 (1H, dd, J 2.6, 8.7 Hz), 6.91 (2H, d, J 8.6 Hz), 4.11 (2H, t, J 5.1 Hz), 3.89 (3H, s), 3.03 (2H, t, J 5.1 Hz), 2.96 (1H, quintet, J 6.2 Hz), 2.80 (1H, br s), 2.68 (2H, s), 1.28 (6H, s) and 1.15 (6H, d, J 6.2 Hz).

The starting tosylate Was prepared from 6,6-dimethyl-N-[4-(2-hydroxyethoxy)phenyl]-9-methoxybenzo[h]-5,6-dihydroquinazoline-2-amine and tosylchloride following the analogous method described in Example 82. This gave the desired compound as a pale yellow solid. δH (CDCl$_3$) 8.21 (1H, s), 7.87 (1H, d, J 2.9 Hz), 7.83 (1H, d, J 8.3 Hz), 7.58 (2H, d, J 9.0 Hz), 7.32 (2H, d, J 8.6 Hz), 7.29 (1H, br s), 7.01 (1H, dd, 2.9, 5.0 Hz), 6.79 (2H, d, J 9.0 Hz), 4.39 (2H, t, J 4.8 Hz), 4.15 (2H, t, J 5.0 Hz), 3.89 (3H, s), 2.69 (2H, s), 2.44 (3H, s) and 1.28 (6H, s). MS (ES$^+$) 546 (MH$^+$, 100%).

6,6-Dimethyl-N-[4-(2-hydroxyethoxy)phenyl]-9-methoxybenzo[h]-5,6-dihydro-quinazoline-2-amine was prepared from the compound of Example 61 (600 mg, 1.73 mmol) following the procedure described for Example 81 to give the desired product as a pale yellow solid (636 mg) m.p. 164–166° MS (ES$^+$) 394 (MH$^+$, 100).

EXAMPLE 85

N-{4-[2-(Amidinothio)ethoxy]phenyl}-6,6-dimethyl-9-methoxybenzo[h]-5,6-dihydroquinazoline-2-amine 4-toluenesulphonate 6,6-Dimethyl-9-methoxy-N-[4-(2-p-toluenesulphonyloxyethoxy)phenyl]-benzo[h]-5,6-dihydroquinazoline-2-amine (440 mg, 0.81 mmol; see Example 84) and thiourea (92 mg, 1.21 mmol) were heated at reflux in ethanol (25 ml) for 18 h. Water (5 ml) was added to the reaction and the mixture cooled to give the product as a yellow precipitate. Trituration of the precipitate with hot ethyl acetate gave the title compound as a yellow solid (205 mg) m.p. 214–216°. δH (d$^6$DMSO) 9.38 (1H, s), 9.10 (4H, br m), 8.33 (1H, s), 7.78 (3H, m), 7.48 (2H, d, J 8.0 Hz), 7.40 (1H, d, J 8.6 Hz), 7.10 (3H, m), 6.92 (2H, d, J 9.0 Hz), 4.23 (2H, t, J 5.4 Hz), 3.84 (3H, s), 3.58 (2H, t, J 5.7 Hz), 2.69 (2H, s), 2.69 (3H, s) and 1.23 (6H, s).

EXAMPLE 86

6,6-Dimethyl-N-[3-(2-dimethylaminoethyl)phenyl]-9-methoxybenzo[h]-5,6-dihydroquinazoline-2-amine A solution of 6,6-dimethyl-9-methoxy-N-[3-(2-p-toluenesulphonyloxyethyl)phenyl]-benzo[h]-5,6-dihydroquinazoline-2-amine (400 mg, 0.76 mmol) in DMF (8 ml) in a thick walled Schlenk tube was cooled to –20° and dimethylamine (approximately 5 ml) condensed into the tube. The reaction was allowed to warm to room temperature, the Schlenk tube was sealed and heated to 50° (CARE! blast screen) for 3 h. The reaction was allowed to cool to room temperature, diluted with ethyl acetate (25 ml) and washed with brine (25 ml×2). The ethyl acetate layer was dried (MgSO$_4$) and concentrated in vacuo to give the title compound as a yellow solid (187 mg) m.p. 103.2°. δH (CDCl$_3$) 8.24 (1H, s), 7.91 (1H, d, J 2.9 Hz), 7.59 (1H, s), 7.57 (1H, s), 7.33 (1H, d, J 8.6 Hz), 7.25 (1H, m), 7.16 (1H, br, s), 7.01 (1H, dd, J 2.9, 8.5 Hz), 6.88 (1H, d, J 7.5 Hz), 3.89 (3H, s), 2.84 (2H, m), 2.70 (4H, m), 2.37 (6H, s) and 1.28 (6H, s).

The tosylate starting material was prepared from the compound of Example 60 (1.7 g, 4.5 mmol) and tosyl chloride (3.5 g, 18.1 mmol) following the method described in Example 82 to give the starting material as a yellow solid (2.30 g) which was used in the above reaction without purification.

EXAMPLE 87

N-[3-Chloro-4-(2-isopropylaminoethoxy)-5-methylphenyl]-6,6-dimethyl-9-methoxybenzo[h]-5,6-dihydroquinazoline-2-amine dihydrochloride A solution of the compound of Example 88 (361 mg, 0.82 mmol) and 4-toluenesulphonyl chloride (468 mg, 2.46 mmol) in dry pyridine (5 ml) under a N$_2$ atmosphere was stirred at ambient temperature for 12 h. The reaction was partitioned between ethyl acetate and 2M hydrochloric acid, the organic phase was washed with saturated NaHCO$_3$, dried (MgSO$_4$) and then evaporated under reduced pressure. The crude compound was taken up in dry DMF (15 ml), isopropylamine (1.0 ml) was added and the reaction heated at 70° for 12 h. On cooling the solvent was removed under reduced pressure and the residue partitioned between ethyl acetate and saturated brine, then the organic phase was dried (MgSO$_4$) and evaporated. The residue was redissolved in ethyl acetate and a stream of dry HCl gas was bubbled into the solution. The resulting solid was collected and dried to give the title compound (38 mg) as a yellow solid m.p. >78° (decomp). δH (d$^6$DMSO) 9.69 (1H, s), 9.06 (2H, br s), 8.39 (1H, s), 8.06 (1H, s), 7.79 (1H, d, J 2.6 Hz), 7.56 (1H, s), 7.42 (1H, d, 8.6 Hz), 7.11 (1H, dd, 2.6, 8.6 Hz), 4.15 (2H, m), 3.87 (3H, s), 3.48–3.36 (3H, m), 2.71 (2H, s), 2.33 (3H, s), 1.30 (3H, d, J 6.5 Hz) and 1.23 (6H, s).

EXAMPLE 88

N-[3-chloro-4-(2-hydroxyethoxy)-5-methylphenyl]-6,6-dimethyl-9-methoxybenzo[h]-5,6-dihydroquinazoline-2-amine The title compound was prepared as a clear oil from the compound of Example 89 (320 mg, 0.7 mmol), ethylene carbonate (152 mg, 1.1 mmol) and potassium carbonate (185 mg, 2.1 mmol) following the method of Example 81.

EXAMPLE 89

N-[3-Chloro-4-hydroxy-5-methylphenyl]-6,6-dimethyl-9-methoxy-benzo[h]-5,6-dihydroquinazoline-2-amine The title compound was prepared as a gold solid from 2-chloro-6,6-dimethyl-9-methoxybenzo[h]-5,6-dihydroquinazoline (0.75 g, 2.73 mmol) and 4-amino-2-chloro-6-methylphenol (0.43 g, 2.73 mmol) following the method of Example 48 m.p. >230° dec.

EXAMPLE 90

9-Carboxy-6,6-dimethyl-N-[4-(2-dimethylaminoethoxy)phenyl]-benzo[h]-5,6-dihydroquinazoline-2-amine dihydrochloride Powdered sodium hydroxide (1.01 g, 25.2 mmol) was added to 4-(2-dimethylaminoethoxy)phenylguanidinium dinitrate (4.18 g, 12.0 mmol) in isopropanol (30 ml) and stirred for 5 min. 3,4-Dihydro-6,6-dimethyl-2-dimethylaminomethylene-7-methoxycarbonyl-1(2H)naphthalenone (3.30 g, 12.0 mmol) was added and the mixture heated to reflux for 3 h. Removal of solvent and purification by column chromatography (5–10% $CH_3OH$ in $CH_2Cl_2$) gave the title compound as a mixture of methyl and isopropyl esters (2.88 g). This mixture was dissolved in ethanol (60 ml), treated with 4M aqueous NaOH (15.3 ml, 61.0 mmol) and heated to reflux for 1.5 h. Ethanol was removed in vacuo and the residue treated with 2M hydrochloric acid with stirring. The resultant finely divided bright yellow solid was filtered off, washed with more 2M hydrochloric acid (2×15 ml), water (2×15 ml) and dried in a vacuum oven to give the title compound as a yellow solid (2.69 g). δH (d⁶DMSO) 10.83 (1H, br s), 9.72 (1H, br s), 8.88 (1H, d, J 1.9 Hz), 8.38 (1H, s), 8.06 (1H, dd, J 1.9, 8.1 Hz), 7.72 (2H, d, J 8.9 Hz), 7.64 (1H, d, J 8.1 Hz), 6.98 (2H, d, J 8.9 Hz), 4.36 (2H, t, J 4.9 Hz), 3.48 (2H, m), 2.83 (6H, d, J 5.0 Hz), 2.77 (2H, s) and 1.29 (6H, s). MS (ES+) 433 (MH+, 100%).

The naphthalenone used as starting material was prepared from 3,4-dihydro-6,6-dimethyl-7-methoxycarbonyl-1-(2H)naphthalenone [4.20 g, 18.1 mmol; Johnson et al J. Med. Chem. (1996) 39, 26, 5027–5030], and N,N-dimethylformamide dimethyl acetal (25 ml) following the method used for the compound of Example 1 to give the desired material as a yellow solid (4.02 g) m.p. 111–140° MS(ES+) 288 (MH+, 10%).

EXAMPLE 91

6,6-Dimethyl-N-[4-(2-dimethylaminoethoxy)phenyl]-9-methoxycarbonylbenzo[h]-5,6-dihydroquinazoline-2-amine Chlorotrimethylsilane (0.38 ml, 3.0 mmol) was added dropwise to a solution of the compound of Example 90 (500 mg, 1.0 mmol) in methanol (10 ml) and the mixture heated under a gentle reflux for 2 h. The reaction was allowed to cool to room temperature, methanol was removed in vacuo and the residue partitioned between $CH_2Cl_2$ (50 ml) and saturated aqueous $NaHCO_3$ (50 ml). The aqueous layer was re-extracted with $CH_2Cl_2$ (3×50 ml) and the combined $CH_2Cl_2$ layers washed with 2M NaOH (2×20 ml), dried ($MgSO_4$) and concentrated in vacuo. Chromatography on silica (6% $CH_3OH$ in $CH_2Cl_2$) gave the title compound as a yellow solid (418 mg) m.p. 60–64°. δH ($CDCl_3$) 8.98 (1H, d, J 2.0 Hz), 8.23 (1H, s), 8.10 (1H, dd, J 2.0, 8.2 Hz), 7.59 (2H, dt, J 9.0, 2.3 Hz), 7.49 (1H, d, J 8.2 Hz), 7.03 (1H, br s), 6.95 (2H, dt, J 9.0, 2.3 Hz), 4.12 (2H, t, J 5.7 Hz), 3.97 (3H, s), 2.80 (2H, t, J 5.7 Hz), 2.73 (2H, s), 2.40 (6H, s) and 1.32 (6H, s). MS (ES+) 447 (MH+, 100%).

EXAMPLE 92

6,6-Dimethyl-N-[4-(2-dimethylaminoethoxy)phenyl]-9-(N',N'-dimethylcarboxamido)benzo[h]-5,6-dihydroquinazoline-2-amine To a mixture of the compound of Example 90 (250 mg, 0.5 mmol), dimethylamine hydrochloride (81 mg, 0.99 mmol), 1-(3-dimethylaminopropyl)-3-ethylcarbodiimide hydrochloride (105 mg, 0.54 mmol) and 1-hydroxy-7-azabenzotriazole (75 mg, 0.54 mmol) in dry DMF (10 ml) was added N-methylmorpholine (0.27 ml, 2.5 mmol). The reaction was stirred at room temperature for 3 h, solvent was removed in vacuo and the residue partitioned between ethyl acetate (50 ml) and water (50 ml). The ethyl acetate layer was washed with 2MNaOH (50 ml), water (50 ml), dried ($MgSO_4$) and concentrated in vacuo to a yellow oil. Trituration of the oil with ether-hexane gave the title compound as a yellow solid (122 mg) m.p. 118.6°. δH ($CDCl_3$) 8.37 (1H, d, J 1.7 Hz), 8.21 (1H, s), 7.54 (3H, m), 7.45 (1H, d, J 7.9 Hz), 6.97 (1H, s), 6.92 (2H,m), 4.07 (2H, t, J 5.8 Hz), 3.10 (6H, br d), 2.73 (2H, t, J 5.8 Hz), 2.34 (6H, s) and 1.31 (6H, s). MS (ES+) 460 (MH+, 50%), 232 (70%).

EXAMPLE 93

6,6-Dimethyl-N-[4-(2-dimethylaminoethoxy)phenyl]-9-(N'-methylcarboxamido)benzo[h]-5,6-dihydroquinazoline-2-amine The title compound was prepared following the procedure used for Example 92 substituting methylamine hydrochloride (67.5 mg, 1.00 mmol) for dimethylamine hydrochloride. The crude product was purified by chromatography on silica (10% $CH_3OH$ in $CH_2Cl_2$) to give the title compound as a yellow solid (150 mg) m.p. 99–101° δH ($CDCl_3$) 8.60 (1H, d, J 2.0 Hz), 8.22 (1H, s), 7.94 (1H, dd, J 2.0, 8.0 Hz), 7.54 (2H, d, J 8.9 Hz), 7.48 (1H, d, J 8.1 Hz), 7.04 (1H, br s), 6.93 (2H, d, J 8.9 Hz), 6.36 (1H, br s), 4.07 (2H, t, J 5.7 Hz), 3.04 (3H, d, J 4.8 Hz), 2.74 (2H, t, J 5.7 Hz), 2.71 (2H, s), 2.35 (6H, s) and 1.31 (6H, s). MS (ES+) 446 (MH+, 100%), 224 (86%).

EXAMPLE 94

9-Carboxamido-6,6-dimethyl-N-[4-(2-dimethylaminoethoxy)phenyl]-benzo[h]-5,6-dihydroquinazoline-2-amine Isobutyl chloroformate (83 mg, 0.61 mmol) was added to a mixture of the compound of Example 90 (280 mg, 0.55 mmol) and triethylamine (0.31 ml, 2.20 mmol) in dry THF (10 ml) and the reaction stirred under $N_2$ for 30 min. Ammonium hydroxide solution 28% w/w (5 ml) was added and the reaction stirred for a further 4 h at room temperature. The mixture was diluted with $CH_2Cl_2$ (50 ml) and washed with $H_2O$ (20 ml). The aqueous layer was re-extracted with $CH_2Cl_2$ (20 ml) and the combined $CH_2Cl_2$ layers washed with brine (20 ml), dried ($MgSO_4$) and concentrated in vacuo. The crude product was purified by chromatography on silica (10–15% $CH_3OH$ in $CH_2Cl_2$) to give the title compound as a yellow solid (150 mg) δH ($CDCl_3$) 9.39 (1H, s), 8.77 (1H, d, J 1.9 Hz), 8.34 (1H, s), 8.02 (1H, br s), 7.95 (1H, dd, J 2.0, 8.1 Hz), 7.72 (2H, dm, J 9.0 Hz), 7.56 (1H, d, J 8.1 Hz), 7.36 (1H, br s), 6.88 (2H, dm, J 9.0 Hz), 4.02 (2H, t, J 5.8 Hz), 2.73 (2H, s), 2.65 (2H, t, J 5.8 Hz), 2.25 (6H, s) and 1.28 (6H, s). MS (ES$^+$) 432 (MH$^+$ 100%).

EXAMPLE 95

N-(4-Carboxyphenyl)-9-methoxybenzo[h]-5,6-dihydroquinazoline-2-amine hydrochloride A mixture of 2-chloro-9-methoxybenzo[h]-5,6-dihydroquinazoline (986 mg, 4.0 mmol) and 4-aminobenzoic acid (553 mg, 4.0 mmol) in 2-ethoxyethanol (10 ml) was heated to reflux for 18 h. The reaction mixture was cooled to room temperature and the resultant precipitate collected by filtration and was washed with ethanol (3×15 ml) to give the title compound as a light yellow powder (1.10 g, 72%). m.p. >300°. δH (d$^6$DMSO) 9.98 (1H, s), 8.46 (1H, s), 7.97 (2H, d, J 8.9 Hz), 7.88 (2H, d, J 8.9 Hz), 7.78 (1H, d, J 2:8 Hz), 7.28 (1H, d, J 8.3 Hz), 7.04 (1H, dd, J 2.8, 8.3 Hz), 3.85 (3H, s) and 2.83 (4H,m).

2-Chloro-9-methoxybenzo[h]-5,6-dihydroquinazoline was prepared using the synthetic route described for 2-chloro-6,6-dimethyl-9-methoxy-benzo[h]-5,6-dihydroquinazoline in Example 48 to give the compound as a yellow solid m.p. 138°. The data for the intermediates in the synthesis is as follows:

9-Methoxybenzo[h]-5,6-dihydroquinazolin-2-one: buff solid, m.p. >300° (decomp). δH (d$^6$DMSO) 8.58 (1H, s), 7.56 (1H, d, J 2.6 Hz), 7.15 (1H, d, J 8.2 Hz), 6.87 (1H, dd, 2.6, 8.2 Hz), 6.72 (1H, br s), 3.81 (3H, s) and 2.85–2.78 (4H, m).

9-Methoxybenzo[h]-5,6-dihydroquinazoline-2-amine: beige solid m.p. 188° δH (CDCl$_3$) 8.14 (1H, s), 8.05 (1H, s), 7.18 (1H, dd, J 1.3, 7.6 Hz), 7.12 (1H, d, J 7.6 Hz), 4.98 (2H, br s), 2.89–2.85 (2H, m), 2.78–2.73 (2H, m) and 2.40 (3H, s).

The preparation of 3,4-dihydro-2-dimethylaminomethylene-7-methoxy-1(2H)naphthalenone was previously described in Example 4.

EXAMPLE 96

N-{4[N'-(2-aminoethyl)carboxamido]phenyl}-9-methoxybenzo[h]-5,6-dihydroquinazoline-2-amine Trifluoroacetic acid (15 ml) was added to a suspension of N-{4-[N'-(2-tertbutoxycarbonylaminoethyl)carboxamido] phenyl}-9-methoxybenzo[h]-5,6-dihydroquinazoline-2-amine (300 mg, 0.61 mmol) in CH$_2$Cl$_2$ (15 ml) and the reaction stirred at room temperature for 1 h. Excess trifluoroacetic acid and solvent was removed in vacuo and the residue dissolved in CH$_2$Cl$_2$ (50 ml) and washed with 2MNaOH (2×20 ml), dried (MgSO$_4$) and concentrated in vacuo to a white solid. Recrystallisation from ethyl acetate gave the title compound as a white solid (200 mg) m.p. 180–186° δH (CDCl$_3$) 8.28 (1H, s), 8.08 (1H, s), 7.67 (2H, d, J 9.0 Hz), 7.62 (2H, d, J 9.0 Hz), 7.615 (1H, m), 7.36 (1H, br t, J 5.3 Hz), 6.96 (1H, d, J 8.4 Hz), 6.73 (1H, dd, J 2.8, 8.4 Hz), 3.67 (3H, s), 3.26 (2H, q, J 5.6 Hz), 2.70 (2H, t, J 5.7 Hz) and 2.67–2.58 (4H, m). MS (ES$^+$) 390 (MH$^+$, 100%).

The amine starting material used in the reaction was prepared from the compound of Example 95 (480 mg, 1.25 mmol) and N-tertbutoxycarbonyl ethylenediamine (221 mg, 1.38 mmol) using the carbodiimide coupling protocol described for the compound of Example 92. The product which precipitated from the reaction mixture was collected and washed with CH$_2$Cl$_2$ (2×20 ml), CH$_3$OH (2×20 ml) and ether (20 ml) to give the desired amine as a white solid (505 mg) δH (CDCl$_3$) 9.82 (1H, s), 8.44 (1H, s), 8.26 (1H, m), 7.93 (2H, d, J 9.0 Hz), 7.78 (2H, d, J 9.0 Hz), 7.76 (1H, s), 7.30 (1H, d, J 8.4 Hz), 7.06 (1H, dd, J 2.8. 8.4 Hz), 6.89 (1H, m), 3.86 (3H, s), 3.36–3.24 (2H, m), 3.11 (2H, m), 2.81 (4H, m) and 1.39 (9H, s). MS (ES$^+$ 490 (MH$^+$, 100%).

EXAMPLE 97

N-{4-[N'-(2-Dimethylaminoethyl)carboxamido] phenyl}-9-methoxy-benzo[h]-5,6-dihydroquinazoline-2-amine Isobutylchloroformate (0.21 ml, 1.6 mmol) was added to a mixture of the conmpound of Example 95 (0.64 ml, 4.5 mmol) in dry THF (25 ml) under N$_2$ and at 0°. The reaction was stirred for 10 min before adding N,N-dimethylethylene diamine (0.2 ml, 1.8 mmol) and was then stirred at room temperature for 1.5 h. THF was removed in vacuo and the residue partitioned between CH$_2$Cl$_2$ and water. The organic layer was separated, dried (MgSO$_4$), concentrated in vacuo and the resultant solid purified by chromatography (silica, 2% Et$_3$N, 10% CH$_3$OH in CH$_2$Cl$_2$) to give the title compound as a white solid (300 mg) m.p. 168–175°. δH (CDCl$_3$) 8.37 (1H, br t, J 5.0 Hz), 8.28 (1H, s), 8.07 (2H, d, J 8.8 Hz), 7.86 (1H, d, J 2.8 Hz), 7.84 (2H, d, J 8.8 Hz), 7.38 (1H, br s), 7.16 (1H, d, J 8.3 Hz), 6.96 (1H, dd, J 2.8, 8.3 Hz), 3.93 (3H, s), 3.89 (2H, q, J 5.0 Hz), 3.26 (2H, t, J 5.4 Hz), 2.86 (6H, s) and 2.84 (4H, m). MS (ES$^+$) 418 (MH$^+$, 100%).

EXAMPLE 98

6,6-Dimethyl-N-[4-(N,'N'-dimethylglycyl) aminophenyl]-9-methoxy-benzo[h]-5,6-dihydroquinazoline2-amine The title compound was prepared from N-[4-aminophenyl]-6,6-dimethyl-9-methoxybenzo[h]-5,6-dihydroquinazoline-2-amine (400 mg, 1.16 mmol) and N,N-dimethylglycine (131 mg, 1.27 mmol) following the carbodiimide coupling procedure described for Example 92. After chromatography on silica (ethyl acetate—1-% CH$_3$OH in CH$_2$Cl$_2$) this afforded the title compound as a yellow powder (180 mg) δH (CDCl$_3$) 9.01 (1H, s), 8.22 (1H, s), 7.91 (1H, d, J 2.8 Hz), 7.70 (2H, d, J 9.0 Hz), 7.59 (2H, d, J 9.0 Hz), 7.35 (1H, d, J 8.7 Hz), 7.19 (1H, s), 7.00 (1H, dd, J 2.8, 8.6 Hz), 3.90 (3H, s), 3.09 (2H, s), 2.70 (2H, s), 2.40 (6H, s), 1.29 (6H, s). MS (ES$^+$) 432 (MH$^+$, 100%).

N-[4-Aminophenyl]-6,6-dimethyl-9-methoxybenzo[h]-5,6-dihydroquinazoline-2-amine was prepared from 1,4 phenylene diamine (472 mg, 4.36 mmol) and 2-chloro-6,6-dimethyl-9-methoxybenzo[h]-5,6-dihydroquinazoline (800 mg, 2.91 mmol) following the method described for Example 48 to give the product as a yellow powder (734 mg) m.p. >250° decomp.

EXAMPLE 99

N3-Glycylaminophenyl)-9-methoxybenzo[h]-5,6-dihydroqinazoline-2-amine

N-(9-Fluorenylmethoxycarbonyl)glycyl chloride (909 mg, 2.88 mmol) was added to a solution of the compound of Example 100 (610 mg, 1.92 mmol) in CH$_2$Cl$_2$ (20 ml) and 5% Na$_2$CO$_3$ (aq) (20 ml) and the mixture stirred vigorously at room temperature for 2 h. The reaction was partitioned between CH$_2$Cl$_2$ (100 ml) and H$_2$O (100 ml), the layers separated and aqueous re-extracted with CH$_2$Cl$_2$ (3×100 ml). The combined CH$_2$Cl$_2$ layers were dried (MgSO$_4$) and concentrated in vacuo to an orange solid which was purified by column chromatography (10% CH₃OH in CH₂Cl₂) to give the FMOC protected title compound as an orange solid (505 mg). This solid was dissolved in DMF (10 ml), a solution of piperidine (0.81 ml) in DMF (3.2 μl) added and the mixture stirred for 2 h at room temperature. Solvent was removed in vacuo and the residue purified by column chromatography (silica, 10% CH₃OH in CH₂Cl₂) to give the title compound as a white solid (110 mg) >126° sublimes. δH (d⁶DMSO) 9.53 (1H, s), 8.39 (1H, s), 8.12 (1H, s), 7.80 (1H, d, $J$ 2.6 Hz), 7.50 (1H, d, J 7.1 Hz), 7.25 (3H, m), 7.03 (1H, dd, $J$ 2.7, 8.3 Hz), 3.83 (3H, s), 3.40 (2H, s) and 2.75 (4H, m). MS (ES⁺) 376 (MH⁺, 100%).

EXAMPLE 100

N-(3-Aminophenyl)-9-methoxybenzo[h]-5,6-dihydroquinazoline-2-amine

The title compound was prepared by transfer hydrogenation of the compound of Example 101 (1.25 g, 3.59 mmol) following the ammonium formate method described in Example 78. This gave the desired compound as a yellow powder (1.04 g) m.p. 162–164°. δH (d⁶DMSO) 9.18 (1H, s), 8.41 (2H, s), 8.34 (1H, s), 7.77 (1H, d, $J$ 2.8 Hz), 7.25 (1H, d, $J$ 8.3 Hz), 7.09 (1H, t, $J$ 2.0 Hz), 7.00 (1H, dd, $J$ 2.8, 8.3 Hz), 6.92 (1H, t, $J$ 7.9 Hz), 6.20 (2H, m), 3.84 (3H, s) and 2.75 (4H, m).

EXAMPLE 101

9-Methoxy-N-(3-nitrophenyl)benzo[h]-5,6-dihydroquinazoline-2-amine

The title compound was prepared from 3-nitroaniline (620 mg, 4.47 mmol), 2-chloro-9-methoxy-5,6-dihydroquinazoline (1.0 g, 4.06 mmol) and ethereal HCl (4 ml of 1.0M solution) following the method of Example 95 to give the desired compound as a yellow solid (1.27 g) m.p. >300°

EXAMPLE 102

N-[2-(2-Acetamidoethylamino)pyrid-5-yl]-6,6-dimethyl-9-methoxy-benzo[h]-5,6-dihydroquinazoline-2-amine From 2-chloro-6,6-dimethyl-9-methoxybenzo[h]-5,6-dihydroquinazoline (50 mg, 1.82 mmol), 2-(2-acetamidoethylamino)-5-aminopyridine (389 mg, 2.09 mmol) and ethereal HCl (2 ml of 1.0M solution) following the method of Example 48 to afford the title compound (139 mg) as a yellow solid m.p. 146–149°. MS (ES⁺) 433 (MH⁺), δH (CDCl₃) 8.52 (1H, s), 8.21 (1H, s), 7.89 (1H, dd, $J$ 2.7, 9.3 Hz), 7.80 (1H, d, $J$ 2.9 Hz), 7.73 (1H, d, $J$ 8.6 Hz), 7.01 (2H,m), 6.77 (2H, m), 3.90 (3H, s), 3.52 (4H, m), 2.70 (2H, s), 2.01 (3H, s) and 1.28 (6H,s).

2-(2-Acetamidoethylamino)-5-aminopyridine

A suspension of 2-(2-acetamidoethylamino)-5-nitropyridine (4.0 g, 17.86 mmol) in ethanol-water (3:1, 160 ml) was shaken with 10% palladium on charcoal (400 mg) under an atmosphere of hydrogen for 5 h then filtered through Celite™ and the filtrate concentrated. The residue was subjected to column chromatography (silica, 3–10% methanol-CH₂Cl₂) to afford the title compound (1.52 g) as an air-sensitive deep mauve gum. MS (ES⁺) 195 (MH⁺). δH (d⁶DMSO) 7.89 (1H, br s), 7.45 (1H, d, $J$ 2.5 Hz), 6.82 (1H, dd, $J$ 2.5, 8.7 Hz), 6.28 (1H, d, $J$ 8.7 Hz), 5.60 (1H, br s), 4.34 (2H, br s), 3.16 (4H, m) and 1.79 (3H, s).

2-(2-Acetamidoethylamino)-5-nitropyridine

A suspension of 2-(2-aminoethylamino)-5-nitropyridine (5.0 g, 27.47 mmol) in carbon tetrachloride (60 ml) was treated with acetic anhydride (5.6 g, 54.9 mmol) and methanol (0.5 ml) and the resulting mixture was refluxed for 2 h then allowed to cool to room temperature. The mixture was filtered and the residue partitioned between 1M sodium hydroxide and CH₂Cl₂. The organic phase was dried (MgSO₄) and concentrated to afford the title compound (5.03 g) as a buff solid m.p. 177–180°. MS(ES⁺) 225 (MH⁺).

EXAMPLE 103

N-[2-(2-Aminoethylamino)pyrid-5-yl]-6,6-dimethyl-9-methoxy-benzo[h]-5,6-dihydroquinazoline-2-amine A solution of the compound of Example 102 (620 mg, 1.43 mmol) in ethanol (5 ml) was treated with 4M sodium hydroxide (10 ml) and the resulting mixture refluxed for 18 h. After cooling to room temperature the mixture was partitioned between water and CH₂Cl₂. The organic phase was dried (MgSO₄), concentrated then triturated with diethyl ether to afford the title compound (398 mg) as a yellow solid m.p. 167–170°. MS (ES⁺) 391 (MH⁺), δH (CDCl₃) 8.22 (1H, s), 8.17 (1H, s), 7.90–7.83 (2H, m), 7.40 (1H, br s), 7.31 (1H, m), 6.99 (1H, m), 6.47 (1H, d, $J$ 8.9 Hz), 4.73 (1H, br s), 3.87 (3H, s), 3.37 (2H,m), 2.96 (2H, m), 2.67 (2H, m), 1.64 (2H, br s) and 1.27 (6H, s).

EXAMPLE 104

6,6-Dimethyl-N-[2-(2-isopropylaminoethylamino) pyrid-5-yl]-9-methoxybenzo[h]-5,6-dihydroquinazoline-2-amine hydrochloride A solution of the compound of Example 103 (350 mg, 0.90 mmol) and acetone (63 mg, 1.08 mmol) in methanol (4 ml) was treated with sodium cyanoborohydride (68 mg, 1.08 mmol) and the resulting mixture stirred for 5 h at room temperature. The mixture was concentrated and the residue subjected to column chromatography (silica, 5% methanol-CH₂Cl₂), then stirred with 2M hydrochloric acid for 2 h, neutralised with sodium bicarbonate and extracted twice with ethyl acetate. The combined organic phase was dried (MgSO₄) and concentrated to afford the title compound (96 mg) as a pale yellow solid m.p. 40–50°. MS (ES⁺) 433 (MH⁺). δH (CDCl₃) 8.22 (1H, d, $J$ 2.5 Hz), 8.17 (1H, s), 7.89–7.82 (2H, m), 7.31 (1H, d, $J$ 8.6 Hz), 6.98 (2H, m), 6.51 (1H, d, $J$ 8.9 Hz), 5.10 (1H, br s), 3.86 (3H, s), 3.48 (2H, m), 2.90 (6H, m), 2.66 (2H, s), 1.26 (6H, s) and 1.15 (6H, d, $J$ 6.4 Hz).

The compounds of Examples 105–108 were prepared using a similar method to that described in Example 1.

EXAMPLE 105

N-[4-(2-Dimethylaminoethoxy)phenyl]-pyrido[3,4-h]-5,6-dihydroquinazoline-2-amine From 6-dimethylaminomethylene-7,8-dihydro-5(6H)-quinolinone (500 mg, 2.48 mmol) and 4-(2-dimethylaminoethoxy)phenylguanidinium dinitrate (863 mg, 2.48 mmol) to afford the title compound (716 mg) as a yellow solid m.p. 136–138°. MS (ES⁺) 362 (MH⁺), δH (CDCl₃) 8.64 (1H, d, $J$ 5.0 Hz), 8.55 (1H, s), 8.31 (1H, s), 8.04 (1H, d, $J$ 5.0 Hz), 7.57 (2H, d, $J$ 8.9 Hz), 7.07 (1H, s), 6.94 (2H, d, $J$ 8.9 Hz), 4.11 (2H, t, $J$ 5.7 Hz), 2.90 (4H, m), 2.76 (2H, t, $J$ 5.7 Hz) and 2.36 (6H, s).

EXAMPLE 106

N-[4-(2-Hydroxyethyl)phenyl]-9-methoxypyrido[3,4-h]-5,6-dihydroquinazoline-2-amine From 6-dimethylaminomethylene-3-methoxy-7,8-dihydro-5(6H)-isoquinolinone (420 mg, 1.81 mmol) and 4-(2-hydroxyethyl)phenyl guanidinium nitrate (440 mg, 1.81 mmol) to afford the title compound (381 mg) as a yellow-brown solid m.p. 174–176°. MS (ES$^+$) 349 (MH$^+$), δH (d$^6$DMSO) 9.53 (1H, s), 8.48 (1H, s), 8.18 (1H, s), 7.69 (2H, d, J 7.5 Hz), 7.41 (1H, s), 7.15 (2H, d, J 7.5 Hz), 4.58 (1H, m), 3.90 (3H, s), 3.58 (2H, m), 2.82 (4H, m) and 2.68 (2H, t, J 7.1 Hz).

The guanidine starting material was prepared from 4-(2-hydroxyethyl)aniline (4.00 g, 29.2 mmol) and cyanamide following the method described in Example 1 to give the desired product as a beige solid (4.60 g) m.p. 130–132°. MS (ES$^+$) 180 (MH$^+$).

EXAMPLE 107

N-[3,5-Dimethoxy-4-(2-hydroxyethoxy)phenyl]-9-methoxypyrido[3,4-h]-5,6-dihydroquinazoline-2-amine From 6-dimethylaminomethylene-3-methoxy-7,8-dihydro-5(6H)-isoquinolinone (410 mg, 1.77 mmol) and 3,5-dimethoxy-4-(2-hydroxyethoxy)phenylguanidinium nitrate (560 mg, 1.77 mmol) to afford the title compound (148 mg) as a pale brown solid m.p. 179–181°. MS (ES$^+$) 425 (MH$^+$), δH (CDCl$_3$) 8.35 (1H, s), 8.10 (1H, s), 7.57 (1H, s), 7.17 (1H, s), 7.08 (2H, s), 4.13 (2H, m), 3.96 (3H, s), 3.93 (6H, s), 3.75 (2H, m), 3.52 (1H br s) and 2.86 (4H, m).

The 3,5-dimethoxy-4-(2-hydroxyethoxy)phenylguanidinium nitrate starting material was prepared as follows:

A slurry of potassium 2,6-dimethoxy-4-nitrophenolate [Collins, R. P. and Davis, M. J. Chem. Soc. (1961), 1986] (38 g, 160 mmol) in DMF (600 ml) was treated with 2-bromoethanol (25 ml, 353 mmol) and hexamethylphosphorus triamide (31 ml, 176 mmol) and the reaction heated at 115° for 6 h. After cooling, the reaction was poured onto 1M hydrochloric acid (1.5 l) and extracted with ethyl acetate (5×500 ml). The organics were washed with 1M sodium hydroxide (4×700 ml), brine (200 ml) and drfied (MgSO$_4$). Concentration in vacuo gave 3,5-dimethoxy-4-(2-hydroxyethoxy)nitrobenzene as an off white solid (31 g) δH (CDCl$_3$) 7.52 (2H, s), 4.21 (2H, t, J 2.9 Hz), 3.94 (3H, s), 3.76 (2H, m) and 2.94 (1H, br s). MS (ES$^+$) 266 (MNa$^+$, 50%), 244 (MH$^+$, 100%). A mixture of this nitrobenzene (750 mg, 3.16 mmol) and 10% palladium on carbon (75 mg) in ethanol (50 ml) was degassed and then subjected to an atmosphere of hydrogen (balloon) for 16 h. at 200. Dichloromethane was added and the solution filtered and solvent removed in vacuo to give 3,5-dimethoxy-4-(2-hydroxyethoxy)aniline as a grey solid (620 mg) after trituration with diethyl ether. δH (CDCl$_3$+DMSO) 5.84 (2H, s), 3.87–3.84 (2H, m), 3.64 (6H, s) and 3.52–3.49 (2H, m). MS (ES$^+$) 214 (MH$^+$, 100%.

3,5-Dimethoxy-4-(2-hydroxyethoxy)phenylguanidinium nitrate was prepared from 3,5-dimethoxy-4-(2-hydroxyethoxy)aniline (1.2 g, 5.63 mmol) and cyanamide (0.38 g, 9.01 mmol) following the method described in Example 1 to give the desired compound as a black, gummy solid (1.80 g). δH (d$^6$DMSO) 9.43 (1H, s), 8.40 (1H, br s), 7.26 (4H, s), 6.55 (2H, s), 3.86 (2H, t, J 5.8 Hz), 3.77 (6H, s) and 3.61 (2H, t, J 5.8 Hz).

EXAMPLE 108

N-[3,5-Dimethoxy-4-(2-hydroxyethoxy)phenyl]-9-methoxypyrido[2,3-h]-5,6-dihydroquinazoline-2-amine From 7-dimethylaminomethylene-2-methoxy-5,6-dihydro-8(5H)-quinolinone (1.20 g, 5.15 mmol) and 3,5-dimethoxy-4-(2-hydroxyethoxy)phenylguanidinium nitrate (1.80 g, 5.67 mmol) to afford the title compound (1.09 g) as a green solid m.p. 132–134°. MS (ES$^+$) 425 (MH$^+$).

The quinolinone starting materials for Examples 105–108 were prepared as follows:

2-Methoxy-5,6,7,8-tetrahydroquinoline

A mixture of 5,6,7,8-tetrahydro-2-quinolone [Meyers, A. I. and Garcia-Munoz, G., J. Org. Chem. (1964) 29, 1435] (7.20 g, 48.32 mmol) and silver carbonate (9.33 g, 33.82 mmol) in THF (100 ml)-benzene (20 ml) was treated with methyl iodide (4.67 ml, 10.28 g, 72.48 mmol) and then heated at reflux for 18 h. On cooling to room temperature the mixture was filtered and the filtrate concentrated to give a brown oil which was subjected to column chromatography (silica, hexane-ethyl acetate, 2:1) to afford the title compound (4.40 g) as yellow oil MS (ES$^+$) 164 (MH$^+$). δH (CDCl$_3$) 7,23 (1H, d, J 8.3 Hz), 6.47 (1H, d, J 8.3 Hz), 3.88 (3H, s), 2.78 (2H, t, J 5.9 Hz), 2.65 (2H, t, J 5.9 Hz) and 1.88–1.71 (4H, m).

3-Methoxy-5,6,7,8-tetrahydroisoquinoline

A mixture of 3-methoxyisoquinoline (800 mg, 5.03 mmol) and platinum dioxide (100 mg) in concentrated hydrochloric acid (10 ml) was shaken under an atmosphere of hydrogen at 40 psi for 5 h. The mixture was diluted with water, filtered through Celite™, basified with sodium hydroxide then extracted four times with ethyl acetate. The combined organic phases were dried (MgSO$_4$) and concentrated to afford the title compound (600 mg) as a clear oil, MS (ES$^+$) 164 (MH$^+$). δH (CDCl$_3$) 7.85 (1H, s), 6.43 (1H, s), 3.87 (3H, s), 2.65 (4H, m) and 1.75 (4H, m).

3-Methoxy-7,8-dihydro-5(6H)-isoquinolinone oxime

A solution of 3-methoxy-5,6,7,8-tetrahydroisoquinoline (1.40 g, 8.59 mmol) in THF (20 ml) was added to a solution of potassium tert-butoxide (1.92 g, 17.18 mmol) in THF (25 ml) and the resulting mixture was stirred at room temperature for 18 h, then cooled to 0° and tert-butyl nitrite (3.05 ml, 2.65 g, 27.77 mmol) added dropwise. After stirring for 18 h at room temperature brine was added and the mixture extracted three times with ethyl acetate. The combined organic phase was dried (MgSO$_4$) and concentrated to afford the title compound (1.50 g) as a flesh coloured solid m.p. 175–178° MS (ES$^+$) 193 (MH$^+$).

2-Methoxy-5,6-dihydro-8(5H)-quinolinone oxime was prepared by the same method from 2-methoxy-5,6,7,8-tetrahydroquinoline (4.40 g, 26.99 mmol) to afford a pale orange solid (2.20 g) m.p. 186–188° MS (ES$^+$) 193 (MH$^+$).

3-Methoxy-7,8-dihydro-5(6H)-isoquinolinone

A solution of 3-methoxy-7,8-dihydro-5(6H)-isoquinolinone oxime (1.20 g, 6.25 mmol) in a mixture of acetone (40 ml) and 6M hydrochloric acid (27 ml) was refluxed for 4 h then allowed to cool to room temperature. The mixture was concentrated to remove acetone then basified with sodium carbonate and extracted four times with ethyl acetate. The combined organic extracts were dried (MgSO$_4$), concentrated and the residue subjected to column chromatography (silica, ethyl acetate-hexane, 1:4) to afford the title compound (0.81 g) as a white solid m.p. 7981°. MS (ES$^+$) 178 (MH$^+$).

2-Methoxy-5,6-dihydro-8(5H)-quinolinone

Potassium permanganate (2.06 g. 13.00 mmol) was added to a stirred suspension of 2-methoxy-5,6-dihydro-8(5H)-quinolin-one oxime (1.25 g, 6.51 mmol) in a mixture of acetonitrile (20 ml) and water (15 ml). After stirring for 1.5 h the mixture was reduced to about 20 ml then partitioned between water and ethyl acetate. The aqueous phase was further extracted three times with ethyl acetate and then the combined organic phase was dried (MgSO$_4$) and concentrated. The residue was subjected to column chromatography (silica, 1% methanol-CH$_2$Cl$_2$) to afford the title compound (1.10 g) as an impure brown oil which was used crude in the next step. δH (CDCl$_3$) 7.50 (1H, d, $J$ 8.2 Hz), 6.90 (1H, d, $J$ 8.2 Hz), 4.00 (3H, s), 2.91 (2H, t, $J$ 6.8 Hz), 2.71 (2H, t, $J$ 6.8 Hz) and 2.15 (2H, m).

The following compounds were prepared by reaction with N,N-dimethyl-formamide diethyl acetal as described in Example 1.

7-Dimethylaminomethylene-2-methoxy-5,6-dihydro-8(5H)-quinolinone

From 2-methoxy-5,6-dihydro-8(5H)-quinolinone (1.25 g, 7.06 mmol) to afford the title compound (1.20 g) as an orange gum. MS (ES$^+$) 233 (MH$^+$). δH (CDCl$_3$) 7.72 (1H, s), 7.40 (1H, d, $J$ 5.4 Hz), 6.73 (1H, d, $J$ 8.4 Hz), 4.02 (3H, s), 3.11 (6H, s), 2.91 (2H, t, $J$ 6.0 Hz) and 2.72 (2H, t, $J$ 6.0 Hz).

6-Dimethylaminomethylene-3-methoxy-7,8-dihydro-5(6H)-isoquinolinone

From 3-methoxy-7,8-dihydro-5(6H)-isoquinolinone (800 mg, 4.52 mmol) to afford the title compound (840 mg) as a yellow-brown solid m.p. 102–104°. MS (ES$^+$) 233 (MH$^+$).

6-Dimethylaminomethylene-7,8-dihydro-5(6H)-isoquinolinone

From 7,8-dihydro-5-(6H)-isoquinolinone [Lardenois, P. et al Synth. Commun. (1996) 26 (12), 2305]; (3.00 g, 20.40 mmol) to afford the title compound (3.30 g) as an orange solid m.p. 76–79°. MS (ES$^+$) 203 (MH$^+$).

EXAMPLE 109

N-[4-(2-Dimethylaminoethyl)phenyl]-9-methoxypyrido[3,4-h]-5,6-dihydroquinazoline-2-amine From 9-methoxy-N-[4-(2-tosyloxyethyl)phenyl]pyrido[3,4-h]-5,6-dihydro quinazoline-2-amine (450 mg, 0.90 mmol) and dimethylamine (6.2 ml) following the method of Example 86 to afford the title compound (213 mg) as a beige solid m.p. 164–166° MS (ES$^+$) 376 (MH$^+$), δH (CDCl$_3$) 8.33 (1H, s), 8.10 (1H, s), 7.60 (2H, d, $J$ 8.5 Hz), 7.56 (1H, s), 7.21 (2H, d, $J$ 8.5 Hz), 7.19 (1H, br s), 3.98 (3H, s), 2.87–2.78 (6H, m), 2.60 (2H, m) and 2.36 (6H, s).

9-Methoxy-N-[4-(2-tosyloxyethyl)phenyl]pyrido[3,4-h]-5,6-dihydroquinazoline-2 amine was prepared from the compound of Example 106 (340 mg, 1.00 mmol) following the method of Example 82 to afford the title compound (465 mg) as a beige solid m.p. 120–122°. MS (ES$^+$) 503 (MH$^+$).

The following compounds of Examples 110–112 were prepared by the methods detailed in Example 82.

EXAMPLE 110

N-[4-(2-Diethylaminoethoxy)-3,5-dimethoxyphenyl]-9-methoxypyrido-[3,4-h]-5,6-dihydroquinazoline-2-amine From N-[3,5-dimethoxy-4-(2-tosyloxyethoxy)phenyl]-9-methoxypyrido[3,4-h]-5,6-dihydroquinazoline-2-amine (120 mg, 0.21 mmol) and diethylamine (152 mg, 2.10 mmol) to afford the title compound (63 mg) as a pale brown solid m.p. 173–175°. MS (ES$^+$) 480 (MH$^+$) δH (d$^6$DMSO) 9.56 (1H, s), 8.51 (1H, s), 8.19 (1H, s), 7.48 (1H, s), 7.31 (2H, s), 3.94 (2H, m), 3.83 (3H, s), 3.81 (6H, s), 3.31 (4H, m), 2.84 (6H, m) and 1.06 (6H, m).

N-[3,5-Dimethoxy-4-(2-tosyloxyethoxy)phenyl]-9-methoxypyrido[3,4-h]-5,6-dihydroquinazoline-2-amine was prepared from N-[3,5-dimethoxy-4-(2-hydroxyethoxy)phenyl]-9-methoxypyrido[3,4-h]-5,6-dihydroquinazoline-2-amine (125 mg, 0.29 mmol) to afford the compound (124 mg) as a beige solid m.p. 179–182°, MS (ES$^+$) 579 (MH$^+$).

EXAMPLE 111

N-[3,5-Dimethoxy-4-(2-ethilaminoethoxy)phenyl]-9-methoxypyrido-[2,3-h]-5,6-dihydroquinazoline-2-amine From N-[3,5-dimethoxy-4-(2-tosyloxyethoxy)phenyl]-9-methoxypyrido[2,3-h]-5,6-dihydroquinazoline-2-amine (500 mg, 0.86 mmol) and ethylamine (9 ml of a 2M solution in methanol, 18 mmol) to afford the title compound (331 mg) as a yellow solid m.p. 138–140°. MS (ES$^+$) 452 (MH$^+$) δH (CDCl$_3$) 8.34 (1H, s), 7.57 (1H, s), 7.48 (1H, d, $J$ 8.2 Hz), 7.02 (2H, s), 6.80 (1H, d, $J$ 8.2 Hz), 4.07 (5H, m), 3.86 (6H, s), 2.87 (6H, m), 2.69 (2H, q, $J$ 7.0 Hz) and 1.15 (3H, t, $J$ 7.0 Hz).

N-[3,5-Dimethoxy-4-(2-tosyloxyethoxy)phenyl]-9-methoxypyrido[2,3-h]-5,6-dihydroquinazoline-2-amine was prepared from N-[3,5-dimethoxy-4-(2-hydroxyethoxy)phenyl]-9-methoxypyrido[2,3-h]-5,6-dihydroquinazoline-2-amine (1.05 g, 2.48 mmol) to afford the title compound (1.10 g) as a yellow solid m.p. 132–134°. MS (ES$^+$) 579 (MH$^+$).

EXAMPLE 112

N-[4-(2-Diethylaminoethoxy)-3,5-dimethoxyphenyl]-9methoxypyrido[2,3-h]-5,6-dihydroquinazolihe-2-amine From N-[3,5-dimethoxy-4-(2-tosyloxyethoxy)phenyl]-9-methoxypyrido-[2,3-h]-5,6-dihydroquinazoline-2-amine (500 mg, 0.86 mmol) and diethylamine (190 mg, 2.60 mmol) to afford the title compound (330 mg) as a yellow solid m.p. 132–134°. MS (ES$^+$) 480 (MH$^+$) δH (CDCl$_3$) 8.33 (1H, s), 7.48 (1H, d, $J$ 8.3 Hz), 7.26 (1H, s), 7.02 (2H, s), 6.80 (1H, d, $J$ 8.3 Hz), 4.10 (3H, s), 4.03 (2H, t, $J$ 6.9 HZ), 3.86 (6H, s), 2.92–2.80 (6H, m), 2.65 (4H, q, $J$ 7.1 Hz) and 1.06 (6H, t, 7.1 Hz).

EXAMPLE 113

N-3,5-Dimethyl-4-hydroxyphenyl)-6,6-dimethyl-9-methoxybenzo[h]-5,6-dihydroquinazoline-2-amine The title compound was prepared from 2-chloro-6,6-dimethyl-9-methoxybenzo[h]-5,6-dihydroquinazoline (5.3 g, 19.3 mmol) and 4-amino-2,6-dimethylphenol acetate (5.06 g, 25.7 mmol) following the procedure used for Example 48 to give the title compound as a dark yellow solid (5.0 g). δH (CD$_3$OD-CDCl$_3$) 7.87 (1H, s), 7.63 (1H, d, J 2.9 Hz), 7.10 (1H, d, J 8.6 Hz), 7.02 (2H, s), 6.78 (1H, dd, J 8.6, 2.9 Hz), 3.64 (3H, s), 2.44 (2H, s), 2,02 (6H, s) and 1.03 (6H, s). MS (ES$^+$) 376 (MH$^+$, 100%).

EXAMPLE 114

N-[3,5-Dimethyl-4-(2-hydroxyethoxy)phenyl]-6,6-dimethyl-9-methoxybenzo[h]-5,6-dihydroquinazoline-2-amine The title compound was prepared from the compound of Example 113 (5.0 g, 13.3 mmol), ethylene carbonate (2.35 g, 26.7 mmol) and potassium carbonate (7.37 g, 53.3 mmol) following the procedure of Example 81. This gave the title compound after chromatography on silica (40% ethyl acetate in hexane) as a pale lemon glass (4.12 g) δH (d$^6$DMSO) 9.27 (1H, s), 8.33 (1H, s), 7.821 (1H, d, J 2.9 HZ), 7.50 (2H, s), 7.40 (1H, d, J 8.6 Hz), 7.07 (1H, dd, J 8.6, 2.9 Hz), 3.86 (3H, s), 3.73 (4H, m), 2.68 (2H, s), 2.23 (6H, s), 1.23 (6H, s). MS (ES$^+$) 420 (MH$^+$, 100%).

EXAMPLE 115

N-[4-(2-diethylaminoethoxy)-3,5-dimethylphenyl]-6,6-dimethyl-9-benzo[h]-5,6dihydroquinazoline-2-amine The title compound was prepared from N-[3,5-dimethyl-4-(2-ptoluenesulphonyloxyethoxy)phenyl]-6,6-dimethyl-9-methoxybenzo[h]5,6-dihydroquinazoline-2-amine (700 mg, 1.15 mmol) and diethylamine (1.68 g, 23 mmol) following the method of Example 82. After purification by column chromatography (3–6% CH$_3$OH in CH$_2$Cl$_2$) the resultant gum was dissolved in CH$_2$Cl$_2$, treated wieh ethereal HCl (1.4 ml of 1.0M solution) and triturated with diethyl ether to give the title compound as a yellow solid (358 mg) m.p. 74–76°. δH (d$^6$DMSO) 10.40 (1H, br s), 9.52 (1H, br s), 8.37 (1H, s), 7.81 (1H, s), 7.54 (2H, s), 7.43 (1H, d, J 8.7 Hz), 7.10 (1H, br d, J 8.7 Hz), 4.11 (2H, m), 3.87 (3H, s), 3.51 (2H, m), 3.28 (4H, m), 2.71 (2H, s), 2.28 (6H, s), 1.29 (6H, t, J 7.4 Hz) and 1.24 (6H,s).

The tosylate starting material used above was prepared from the compound of Example 114 (4.12 g, 9.83 mmol) and ptoluenesulphonyl chloride (7.50 g, 39.3 mmol) following the method used in Example 82. This gave the desired compound as a yellow solid (4.91 g). δH (CDCl$_3$) 7.95 (1H, br s), 7.84 (4H, m), 7.36 (4H, m), 7.19 (2H, m), 4.36 (2H, m), 3.98 (2H, m), 3.89 (3H, s), 2.74 (2H, s), 2.44 (3H, s), 2.23 (6H, s) and 1.30 (6H, s). MS (ES$^+$) 574 (MH$^+$, 100%).

EXAMPLE 116

6-Aza-5,5-dioxo-6-methyl-5-thia-N-(3,4,5-trimethoxy phenyl)benzo[h]-5,6-dihydroquinazoline-2-amine The title compound was prepared from 3,4,5-trimethoxyphenyl guanidinium nitrate (650 mg, 2.26 mmol), sodium hydroxide (99 mg, 2.49 mmol) and 3,4-dihydro-3-dimethylaminomethylene-1-methyl-2,2,4-trioxobenzo[c]-2,1-thiazine (600 mg, 2.26 mmol) following the procedure described in Example 1. This gave the title compound as green crystals (411 mg) m.p. 202–204°. δH (CDCl$_3$) 8.91 (1H, s), 8.53 (1H, d, J 6.5 Hz), 7.65 (1H, t, J 7.3 Hz), 7.58 (1H, br s), 7.32 (1H, t, J 7.5 Hz), 7.27(1H, d, J 8.9 Hz), 7.01 (2H, s), 3.91 (6H, s), 3.87 (3H, s) and 3.49 (3H, s).

3,4-Dihydro-3-dimethylaminomethylene-1-methyl-2,2,4-trioxobenzo[c]-2,1-thiazine was prepared from 3,4-dihydro-1-methyl-2,2,4-trioxobenzo[c]-2,1-thiazine (1.0 g, 4.73 mmol) and dimethylformamide diethyl acetal (2.0 ml, 11.83 mmol) following the method described in Example 1 to give the compound after column chromatography (Silica, ethyl acetate) as a yellow solid (1.05 g) δH (D$^4$-CH$_3$OH) 8.01 (1H, d, J 7.7 Hz), 7.86 (1H, br s), 7.53 (1H, t, J 7.6 Hz), 7.21 (1H, t, J 7.5 Hz), 7.17 (1H, d, J 8.6 Hz), 3.38 (3H, s), 3.32 (3H, s) and 3.28 (3H, s). MS (ES$^+$) 267 (MH$^+$, 100%).

EXAMPLE 117

9-Methoxy-N-3,4,5-trimethoxyphenyl)benzo[h]-quinazoline-2-amine

To a solution of 9-methoxy-N-(3,4,5-trimethoxyphenyl)benzo[h]-5,6-dihydroquinazoline-2-amine (489 mg, 1.25 mmol) in dry 1,4-dioxane (20 ml) was added 2,3-dichloro-5,6-dicyano-1,4-benzoquinone (316 mg, 1.38 mmol) and the reaction heated to reflux under N$_2$ for 2 h. Solvent was removed in vacuo and the residue partitioned between CH$_2$Cl$_2$ (100 ml) and 2M NaOH aq. (80 ml). The aqueous layer was re-extracted with CH$_2$Cl$_2$ (2×50 ml) and the combined CH$_2$Cl$_2$ layers washed with 2M NaOH (80 ml), dried (MgSO$_4$) and concentrated in vacuo to a light yellow solid. Recrystallisation from ethyl acetate gave the title compound as light yellow crystals (300 mg). δH (CDCl$_3$) 9.04 (1H, s), 8.51 (1H, d, J 2.7 Hz), 7.80 (1H, d, J 8.8 Hz), 7.57 (1H, d, J 8.7 Hz), 7.47 (1H, d, J 8.7 Hz), 7.37 (1H, dd, J 8.7, 2.7 Hz), 7.29 (1H, br s), 7.18 (2H, s), 4.01 (3H, s), 3.96 (6H, s) and 3.87 (3H, s). MS (ES$^+$) 392 (MH$^+$, 100%).

Biological Activity

The following assays were used to demonstrate the activity and selectivity of compounds according to the invention. Enzymes for the assays were either obtained commercially or purified from known natural or recombinant sources using conventional methods.

p56$^{lck}$ Kinase Assay

The tyrosine kinase activity of p56$^{lck}$ was determined using a RR-src peptide (RRLIEDNEYTARG) and [Δ-$^{33}$P] ATP as substrates. Quantitation of the $^{33}$P-phosphorylated peptide formed by the action of p56$^{lck}$ was achieved using an adaption of the method of Geissler et al (J. Biol. Chem. (1990) 265, 22255–22261).

All assays were performed in 20 mM HEPES pH 7.5 containing 10 mM MgCl$_2$, 10 mM MnCl$_2$, 0.05% Brij, 1 μM ATP (0.5 μCi[γ-$^{33}$P]ATP) and 0.8 mg/ml RR-src. Inhibitors in dimethylsulphoxide (DMSO) were added such that the final concentration of DMSO did not exceed 1%, and enzyme such that the consumption of ATP was less than 10%. After incubation at 30° C. for 15 min, the reaction was terminated by the addition of one-third volume of stop reagent (0.25 mM EDTA and 33 mM ATP in dH$_2$O). A 15 μl aliquot was removed, spotted onto a P-30 filtermat (Wallac, Milton Keynes, UK), and washed sequentially with 1% acetic acid and dH$_2$O to remove ATP. The bound $^{33}$P-RR-src was quantitated by scintillation counting of the filtermat in a Betaplate scintillation counter (Wallac, Milton Keynes, UK) after addition of Meltilex scintillant (Wallac, Milton Keynes, UK).

The dpm obtained, being directly proportional to the amount of $^{33}$P-RR-src produced by p56$^{lck}$, were used to determine the IC$_{50}$ for each compound. The IC$_{50}$ was defined as the concentration of compound required to reduce the production of $^{33}$P-RR-src by 50%.

In this test, compounds according to the invention, such as compounds of the Examples, have IC$_{50}$ values of around 1 μM and below.

Zap-70 and Csk Kinase Assays Inhibitor activity against Zap-70 or Csk kinase was determined using a capture assay based on that employed above for p56$^{lck}$ but with the following modifications. The RR-src peptide was replaced with polyGlu-Tyr (Sigma; Poole, UK) at a final concentration of 17 μg/ml. After addition of the stopped reaction to the filtermat, trichloroacetic acid 10% (w/v) was employed as the wash reagent instead of acetic acid and a final wash in absolute ethanol was also performed before scintillation counting. In these assays, compounds of the invention, such as the compounds of the Examples had little or no measurable activity against either Zap-70 or Csk kinases.

Protein Kinase C Assay

Inhibitor activity against protein kinase C (PKC) was determined using PKC obtained from Sigma Chemical Company (Poole, UK) and a commercially available assay system (Amersham International plc, Amersham, UK). Briefly, PKC catalyses the transfer of the γ-phosphate ($^{32}$p) of ATP to the threonine group on a peptide specific for PKC. Phosphonylated peptide is bound to phosphocellulose paper and subsequently quantified by scintillation counting. The inhibitor potency is expressed as either (i) the concentration required to inhibitor 50% of the enzyme activity (IC$_{50}$) or (ii) the percentage inhibition achieved by 10 μM inhibitor. In this assay, compounds of the invention, such as the compounds of the Examples had little or no measurable activity at concentrations at which they inhibit the activity of p56$^{lck}$.

What is claimed is:

1. A compound of formula (2):

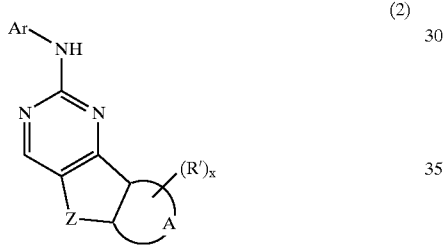

(2)

wherein:

Ar is an optionally substituted phenyl, benzotriazolyl, benzothiazolyl, indolyl, or pyridyl group, wherein said optional substituents are one or more R$^1$ groups;

Z is a C$_{1-2}$alkylene linker group optionally substituted with one or more halogen atoms or C$_{1-3}$alkyl groups;

A, together with the carbons to which it is attached, forms an optionally substituted pyridyl, or thienyl group, wherein said optional substituents are one or more R$^1$ groups;

R$^1$ is a group R$^2$ or -Alk(R$^2$)$_m$;

R$^2$ is a halogen atom or a C$_{1-6}$alkyl, C$_{1-6}$alkylamino, C$_{1-6}$hydroxyalkyl, C$_{1-6}$alkylenethiol, C$_{1-6}$alkoxy, hydroxyC$_{1-6}$alkoxy, C$_{5-7}$cycloalkoxy, haloC$_{1-6}$alkyl, amino (—NH$_2$), aminoC$_{1-6}$alkyl, C$_{1-6}$dialkylamino, C$_{1-6}$alkylaminoC$_{1-6}$alkyl, C$_{1-6}$dialkylaminoC$_{1-6}$alkyl, aminoC$_{1-6}$alkoxy, C$_{1-6}$alkylaminoC$_{1-6}$alkoxy, C$_{1-6}$dialkylaminoC$_{1-6}$alkoxy, phthalimido, naphthalimido, nitro, cyano, amidino, hydroxyl (—OH), formyl, carboxyl (CO$_2$H), —CO$_2$Alk$^1$, C$_{1-6}$alkanoyl, thiol (—SH), thioC$_{1-6}$alkyl, sulfo (—SO$_3$H), C$_{1-6}$alky-Isulphonyl, aminosulphonyl (—SO$_2$NH$_2$), C$_{1-6}$alkylaminosulphonyl, C$_{1-6}$dialkylamino-sulphonyl, phenylaminosulphonyl, carboxamido (—CONH$_2$), C$_{1-6}$alkylaminocarbonyl, C$_{1-6}$dialkylaminocarbonyl, aminoC$_{1-6}$alkyl-aminocarbonyl, C$_{1-6}$dialkylaminoC$_{1-6}$alkylamino-carbonyl, —CONHC(=NH)NH$_2$, sulphonylamino (—NHSO$_2$H), C$_{1-6}$alkylsulphonylamino, C$_{1-6}$dialkylsulphonylamino, phenylsulphonylamino, aminosulphonylamino (—NHSO$_2$NH$_2$), C$_{1-6}$alkylaminosulphonylamino, C$_{1-6}$dialkylaminosulphonylamino, phenylaminosulphonylamino, C$_{1-6}$alkanoylamino, aminoC$_{1-6}$alkanoylamino, C$_{1-6}$dialkylaminoC$_{1-6}$alkanoylamino, C$_{1-6}$alkanoylaminoC$_{1-6}$alkyl, C$_{1-6}$alkanoylamino-C$_{1-6}$alkylamino, C$_{1-6}$alkoxycarbonylamino, benzyloxy, benzyloxycarbonylamino or benzyloxycarbonylaminoC$_{1-6}$alkyl group;

Alk is a straight or branched chain C$_{1-6}$alkylene, C$_{2-6}$alkenylene or C$_{2-6}$alkynylene group optionally interrupted by one, two or three —O— or —S— atoms or —SO—, —S(O)$_2$— or —N(R$^4$)— groups;

R' is a halogen atom or a C$_{1-6}$alkyl, C$_{1-6}$alkylamino, C$_{1-6}$hydroxyalkyl, C$_{1-6}$alkylenethiol, C$_{1-6}$alkoxy, haloC$_{1-6}$alkyl, amino (—NH$_2$), aminoC$_{1-6}$alkyl, C$_{1-6}$dialkylamino, aminoC$_{1-6}$alkoxy, C$_{1-6}$alkylaminoC$_{1-6}$alkoxy, C$_{1-6}$dialkylaminoC$_{1-6}$alkoxy, nitro, cyano, hydroxyl (—OH), formyl, carboxyl (—CO$_2$H), —CO$_2$Alk$^1$, C$_{1-6}$alkanoyl, thiol (—SH), thioC$_{1-6}$alkyl, sulfo (—SO$_3$H), C$_{1-6}$alkylsulphonyl, aminosulphonyl (—SO$_2$NH$_2$), C$_{1-6}$alkylamino-sulphonyl, C$_{1-6}$dialkylamino-sulphonyl, phenylaminosulphonyl, carboxamido (—CONH$_2$), C$_{1-6}$alkylaminocarbonyl, C$_{1-6}$dialkyl-aminocarbonyl, sulphonylamino (—NHSO$_2$H), C$_{1-6}$alkylsulphonylamino, C$_{1-6}$dialkylsulphonyl-amino, phenylsulphonylamino, aminosulphonylamino (—NHSO$_2$NH$_2$), C$_{1-6}$alkylamino-sulphonylamino, C$_{1-6}$dialkylaminosulphonylamino, phenylaminosulphonylamino, C$_{1-6}$alkanoyl-amino, C$_{1-6}$alkanoylaminoC$_{1-6}$alkyl, aminocarbonylamino (—NHCONH$_2$), C$_{1-6}$alkylamino-carbonylamino, C$_{1-6}$dialkylamino-carbonylamino or C$_{1-6}$alkoxycarbonylamino group;

Alk$^1$ is a straight or branched chain C$_{1-8}$alkyl group which is optionally substituted with one or more R$^2$ groups;

m and x are independently zero or an integer 1, 2 or 3;

or a salt, hydrate or N-oxide thereof.

2. A compound according to claim 1 wherein Ar is an optionally substituted phenyl group.

3. A compound according to claim 2 wherein Ar is a phenyl or monosubstituted phenyl group.

4. A compound according to claim 1 wherein the linker group Z is an optionally substituted —(CH$_2$)$_2$— chain.

5. A compound according to claim 4 wherein Z is a —(CH$_2$)$_2$—, —CH$_2$CH(CH$_3$)— or —CH$_2$C(CH$_3$)$_2$— chain.

6. A compound according to claim 1 wherein A forms a thienyl or pyridyl group.

7. A compound according to claim 6 wherein Ar is phenyl monosubstituted with a C$_{1-6}$alkylaminoC$_{1-6}$alkoxy or C$_{1-6}$dialkylaminoC$_{1-6}$alkoxy group.

8. A compound according to claim 7 wherein Z is a C$_1$ alkylene group optionally substituted with one or two C$_{1-3}$alkyl groups.

9. A compound according to claim 8 wherein x is zero or an integer 1.

10. A compound according to claim 9 wherein x is an integer 1 and R' is a C$_{1-6}$alkoxy group.

11. A pharmaceutical composition comprising a compound of formnula (2):

(2)

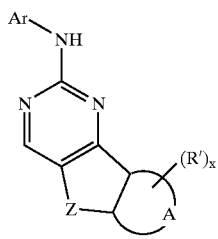

wherein:

Ar is an optionally substituted phenyl, benzotriazolyl, benzothiazolyl, indolyl, or pyridyl group, wherein said optional substituents are one or more $R^1$ groups;

Z is a $C_{1-2}$alkylene group optionally substituted with one or more halogen atoms or $C_{1-3}$ alkyl groups;

A, together with the carbons to which it is attached, forms an optionally substituted pyridyl, or thienyl group, wherein said optional substituents are one or more $R^1$ groups;

$R^1$ is a group $R^2$ or -Alk$(R^2)_m$;

$R^2$ is a halogen atom or a $C_{1-6}$alkyl, $C_{1-6}$alkylamino, $C_{1-6}$hydroxyalkyl, $C_{1-6}$alkylenethiol, $C_{1-6}$alkoxy, hydroxy$C_{1-6}$alkoxy, $C_{5-7}$cycloalkoxy, halo$C_{1-6}$alkyl, amino (—NH$_2$), amino$C_{1-6}$alkyl, $C_{1-6}$dialkylamino, $C_{1-6}$alkylamino$C_{1-6}$alkyl, $C_{1-6}$dialkylamino$C_{1-6}$alkyl, amino$C_{1-6}$alkoxy, $C_{1-6}$alkylamino$C_{1-6}$alkoxy, $C_{1-6}$dialkylamino$C_{1-6}$alkoxy, phthalimido, naphthalimido, nitro, cyano, amidino, hydroxyl (—OH), formyl, carboxyl (—CO$_2$H), —CO$_2$Alk$^1$, $C_{1-6}$alkanoyl, thiol (—SH), thio$C_{1-6}$alkyl, sulfo (—SO$_3$H), $C_{1-6}$alkyl-sulphonyl, aminosulphonyl (—SO$_2$NH$_2$), $C_{1-6}$alkylaminosulphonyl, $C_{1-6}$dialkylamino-sulphonyl, phenylaminosulphonyl, carboxamido (—CONH$_2$), $C_{1-6}$alkylaminocarbonyl, $C_{1-6}$dialkylaminocarbonyl, amino$C_{1-6}$alkyl-aminocarbonyl, $C_{1-6}$dialkylamino$C_{1-6}$alkylamino-carbonyl, —CONHC(=NH)NH$_2$, sulphonylamino (—NHSO$_2$H), $C_{1-6}$alkylsulphonylamino, $C_{1-6}$dialkylsulphonylamino, phenylsulphonylamino, aminosulphonylamino (—NHSO$_2$NH$_2$), $C_{1-6}$alkylaminosulphonylamino, $C_{1-6}$dialkylamino-sulphonylamino, phenylaminosulphonyamino, $C_{1-6}$alkanoylamino, amino$C_{1-6}$alkanoylamino, $C_{1-6}$dialkylamino$C_{1-6}$alkanoylamino, $C_{1-6}$alkanoylamino$C_{1-6}$alkyl, $C_{1-6}$alkanoylamino-$C_{1-6}$alkylamino, $C_{1-6}$alkoxycarbonylamino, benzyloxy, benzyloxycarbonylamino or benzyloxycarbonylamino$C_{1-6}$alkyl group;

Alk is a straight or branched chain $C_{1-6}$alkylene, $C_{2-6}$alkenylene or $C_{2-6}$alkynylene group optionally interrupted by one, two or three —O— or —S— atoms or —SO—, —S(O)$_2$— or —N(R$^4$)— groups;

R' is a halogen atom or a $C_{1-6}$alkyl, $C_{1-6}$alkylamino, $C_{1-6}$hydroxyalkyl, $C_{1-6}$alkylenethiol, $C_{1-6}$alkoxy, halo$C_{1-6}$alkyl, amino (—NH$_2$), amino$C_{1-6}$alkyl, $C_{1-6}$dialkylamino, amino$C_{1-6}$alkoxy, $C_{1-6}$alkylamino$C_{1-6}$alkoxy, $C_{1-6}$dialkylamino$C_{1-6}$alkoxy, nitro, cyano, hydroxyl (—OH), formyl, carboxyl (—CO$_2$H), —CO$_2$Alk$^1$, $C_{1-6}$alkanoyl, thiol (—SH), thio$C_{1-6}$alkyl, sulfo (—SO$_3$H), $C_{1-6}$alkylsulphonyl, aminosulphonyl (—SO$_2$NH$_2$), $C_{1-6}$alkylamino-sulphonyl, $C_{1-6}$dialkylaminosulphonyl, phenylaminosulphonyl, carboxamido (—CONH$_2$), $C_{1-6}$alkylaminocarbonyl, $C_{1-6}$dialkylaminocarbonyl, sulphonylamino (—NHSO$_2$H), $C_{1-6}$alkylsulphonylamino, $C_{1-6}$dialkylsulphonylamino, phenylsulphonylamino, aminosulphonylamino (—NHSO$_2$NH$_2$), $C_{1-6}$alkylaminosulphonylamino, $C_{1-6}$dialkylaminosulphonylamino, phenylaminosulphonylamino, $C_{1-6}$alkanoylamino, $C_{1-6}$alkanoylamino$C_{1-6}$alkyl, aminocarbonylamino (—NHCONH$_2$), $C_{1-6}$alkylaminocarbonylamino, $C_{1-6}$dialkylaminocarbonylamino or $C_{1-6}$alkoxycarbonylamino group;

Alk$^1$ is a straight or branched chain $C_{1-8}$alkyl group which is optionally substituted with one or more $R^2$ groups;

m and x are independently zero or an integer 1, 2 or 3;

or a salt, hydrate or N-oxide thereof;

together with one or more pharmaceutically acceptable carriers, excipients, or diluents.

* * * * *

UNITED STATES PATENT AND TRADEMARK OFFICE
CERTIFICATE OF CORRECTION

PATENT NO.    : 6,599,908 B1
DATED         : July 29, 2003
INVENTOR(S)   : Jeremy Martin Davis et al.

It is certified that error appears in the above-identified patent and that said Letters Patent is hereby corrected as shown below:

Title page,
Item [56], References Cited, OTHER PUBLICATIONS, "Shiori et al." reference, delete "Shiori et al.," and insert -- Shioiri et al., --;
"Porter et al.," reference, delete "Porter et al., "Preparation of 6-phenyl-3-(5-tetrazolyl)pyridin-=(H)-one Derivatives as" and insert -- Porter et al., "Preparation of 6-phenyl-3-(5-tetrazolyl)pyridin-=2(H) -one Derivatives as --;
"Skakibara, K., et al.," "Cartiotonics", " and insert therefore -- Cardiotonics, --;
"Amers, D.E. et al.," delete "Amers, D.E. et al." and insert -- Ames, D.E. et al., --;
"Bortolus et al.," before "Bortolus et al.," insert -- Abstract for --;

Column 3,
Line 66, delete "methylaninosulphonyl" and insert therefore
-- methylaminosulphonyl --;

Column 4,
Line 6, delete "$C_{1-6}$ dialkylaminb" and insert -- $C_{1-6}$ dialkylamino --;

Column 17,
Line 19, delete "-benzo[h]6oxa-" and insert -- -benzo[h]-6-oxa- --;

Column 20,
Line 28, delete "naphthalen one" and insert -- naphthalenone --;

Column 24,
Line 34, delete "-6-thiaguinazoline-" and insert -- 6-thiaquinazoline- --;
Line 47, delete "163-1650." and insert -- 163-165º. --;

Column 26,
Line 33, delete "86-87º0." and insert -- 86-87º. --;

Column 30,
Line 41, delete "200" and insert therefore -- 20º --;

Column 32,
Line 19, delete "(d6DMSO)" and insert -- $d^6$DMSO) --;

Column 37,
Line 23, delete "850" and insert -- 85º --;

UNITED STATES PATENT AND TRADEMARK OFFICE
CERTIFICATE OF CORRECTION

PATENT NO. : 6,599,908 B1
DATED : July 29, 2003
INVENTOR(S) : Jeremy Martin Davis et al.

It is certified that error appears in the above-identified patent and that said Letters Patent is hereby corrected as shown below:

Column 43,
Line 47, delete "111-140º" and insert -- 111-114º --;

Column 54,
Line 37, delete "[Δ-$^{33}$P]" and insert -- [γ-$^{33}$P] --.

Signed and Sealed this

Twenty-seventh Day of July, 2004

JON W. DUDAS
*Acting Director of the United States Patent and Trademark Office*